(12) United States Patent
Zohlnhöfer et al.

(10) Patent No.: US 7,229,760 B2
(45) Date of Patent: Jun. 12, 2007

(54) MRNA AMPLIFICATION

(75) Inventors: Dietlind Zohlnhöfer, München (DE); Christoph Klein, München (DE)

(73) Assignee: Micromet AG, Munich (DE)

( * ) Notice: Subject to any disclaimer, the term of this patent is extended or adjusted under 35 U.S.C. 154(b) by 523 days.

(21) Appl. No.: 10/239,518

(22) PCT Filed: Mar. 23, 2001

(86) PCT No.: PCT/EP01/03311

§ 371 (c)(1),
(2), (4) Date: Feb. 13, 2003

(87) PCT Pub. No.: WO01/71027

PCT Pub. Date: Sep. 27, 2001

(65) Prior Publication Data

US 2004/0029124 A1  Feb. 12, 2004

(30) Foreign Application Priority Data

Mar. 24, 2000  (EP) .................................. 00106450

(51) Int. Cl.
C12Q 1/68 (2006.01)
C12P 19/34 (2006.01)
C07H 21/02 (2006.01)

(52) U.S. Cl. .................. 435/6; 435/91.2; 536/23.1
(58) Field of Classification Search .................. None
See application file for complete search history.

(56) References Cited

U.S. PATENT DOCUMENTS 6,132,997 A * 10/2000 Shannon .................. 435/91.21

FOREIGN PATENT DOCUMENTS

| WO | WO 90/01065 | * | 2/1990 |
| WO | WO 90/01065 A1 | | 2/1990 |
| WO | WO 9001065 A1 | * | 2/1990 |
| WO | WO 90/06044 A1 | | 6/1990 |
| WO | WO 97/08185 A1 | | 3/1997 |
| WO | WO 97/13877 A1 | | 4/1997 |
| WO | WO 97/27317 A1 | | 7/1997 |
| WO | WO 97/48823 A1 | | 12/1997 |
| WO | WO 98/39483 A1 | | 9/1998 |

OTHER PUBLICATIONS

ISR for PCT/EP01/03311, filed Oct. 2002, International, Zohlnhofer, et al.*
Blais et al. Constructing transcriptional regulatory networks. Genes Dev. Jul. 1, 2005;19(13):1499-511.*
Boehringer Mannheim Catalog. 1997. pp. 12, 13, 122.*
Dixon et al. Gene-expression analysis at the single-cell level. Trends Pharmacol Sci. Feb. 2000;21(2):65-70.*
Fleischmann et al. Whole-genome random sequencing and assembly of Haemophilus influenzae Rd. Science. Jul. 28, 1995;269(5223):496-512.*
Gray et al. Exploiting chemical libraries, structure, and genomics in the search for kinase inhibitors. Science. Jul. 24, 1998;281(5376):533-8.*
Gubler et al. A simple and very efficient method for generating cDNA libraries. Gene. Nov. 1983;25(2-3):263-9.*
Klein et al. Comparative genomic hybridization, loss of heterozygosity, and DNA sequence analysis of single cells. Proc Natl Acad Sci U S A. Apr. 13, 1999;96(8):4494-9.*
Lennon G. High-throughput gene expression analysis for drug discovery. Drug Discov Today. Feb. 2000;5(2):59-66.*
Little P. Structure and function of the human genome. Genome Res. Dec. 2005;15(12):1759-66.*
Nelson et al. Addition of homopolymers to the 3'-ends of duplex DNA with terminal transferase. Methods Enzymol. 1979;68:41-50.*
Wang et al. Monitoring gene expression profile changes in ovarian carcinomas using cDNA microarray. Gene. Mar. 18, 1999;229(1-2):101-8.*
Toellner et al., "The use of reverse transcription polymerase chain reaction to analyse large numbers of mRNA species from a single cell," Journal of Immunological Methods, 191:71-75 (1996) © Elsevier Science B.V.
Brady et al., "Analysis of gene expression in a complex differentiation hierarchy by global amplification of cDNA from single cells," Current Biology 5(8): 909-922 (1995).
Zohlnhöfer et al., "Transcriptome Analysis Reveals a Role of Interferon-γ in Human Neointina Formation," *Molecular Cell*, vol. 7, pp. 1059-1069, May 2001.

* cited by examiner

*Primary Examiner*—Jeffrey Fredman
*Assistant Examiner*—Samuel Woolwine
(74) *Attorney, Agent, or Firm*—Foley & Lardner LLP

(57) ABSTRACT

The present invention relates to a method for the amplification of mRNA of a sample, comprising the steps of i.) generating cDNA from polyadenylated RNA employing at least one primer hybridizing to said polyadenylated RNA and comprising a 5' poly(C) or a 5' poly(G) flank; ii.)(aa) if present, removing non-hybridized, surplus primer(s) and/or surplus dNTPs; ii.)(ab) 3' tailing of said generated cDNA with a poly(G) tail when in step i.(a) primer(s) comprising a 5' poly(C) flank was employed or a poly(C) tail when in step i.(a) primer(s) comprising a 5' poly(G) flank was employed; or ii.)(b) 3' tailing of said generated cDNA with a poly(G) tail when in step i.(a) primer(s) comprising a 5' poly(C) flank was employed or a poly(C) tail when in step i.(a) primer(s) comprising a 5' poly(G) flank was employed using an RNA-ligase, irrespective of the presence or absence of surplus primer(s) and/or surplus dNTPs; and iii.) amplifying the tailed cDNA with a primer hybridizing to the tail(s) generated in step ii(ab) or ii(b). Furthermore, the present invention relates to methods for the preparation of in vitro surrogate(s), for identifying expressed genes in a test sample, for identifying a drug candidate for therapy of a pathological condition and for in vitro detection of a pathological condition employing said method for amplification of mRNA. In addition, the present invention relates to the use of amplified cDNA(s) as obtained by the method of the invention in hybridization, interaction and/or enzymatic arrays.

40 Claims, 39 Drawing Sheets

Fig. 6 cont.

| | | | | | | | | | | | |
|---|---|---|---|---|---|---|---|---|---|---|---|
| GFP | BSG | MMP1 | MMP3 | ADAM8 | | | CDKN2B / PTK2 | CCND1 / MYC (I) | MAGE A1 / THBS1 | FCGR3A / TGFA | pBS / ERBB2 |
| KRT7 | MT1MMP | PLAU | MMP11 | ADAM9 | ITGA4 | ITGB1 | CDKN2A / SLA | GAS1 / MYC (II) | MAGEA3 / ABCC1 | CD33 / TGFB1 | TCRA / TGFBR1 |
| KRT8 | MT2MMP | PLAUR | MMP2 | ADAM10 | ITGA5 | ITGB2 | CDKN1A / P68 | MKI67 / RB1 | MAGEA4 / ABCB1 | CD34 / VEGF | IGKC / TGFBR2 |
| KRT10 | MT3MMP | PAI1 | MMP9 | ADAM11 | ITGA6 | ITGB3 | CDKN1B / EPHA2 | ACTB / TK1 | MAGEA6 / PTPRJ | CD37 / IGF1 | IGLC1 / IGFR1 |
| KRT13 | MT4MMP | PAI2 | MMP7 | ADAM15 | ITGAV | ITGB4 | ING1 / EFNA1 | EEF1A1 / RAD51 | MAGEA12 / PTPRM | CD38 / RAMP1 | VIM / IGFR2 |
| KRT18 | TIMP1 | CTSB | CSTA | ADAM20 | GFP | ITGB5 | TP53 (I) / CDH1 | TNFAIP3 / NCK1 | MAGEA1s / CKM | TNFRSF5 / RAMP2 | M4S1 / MCAM |
| KRT19 | TIMP2 | CTSD | CSTB | ADAM21 | | ITGB7 | TP53 (II) / CDH3 | BCL2 / pBS | MAGEA2s / MAGEA4s | PTPRC / BSG (I) | DSP / PHLDA1 |
| KRT20 | TIMP4 | CTSL | CST3 | ADAM17 | ACTB | | CDKN1C / CDH2 | GHPDH / TERT | MAGEA3s / MAGEA12s | CD83 / GFP | CEA / EEF1A1 |

Fig. 7
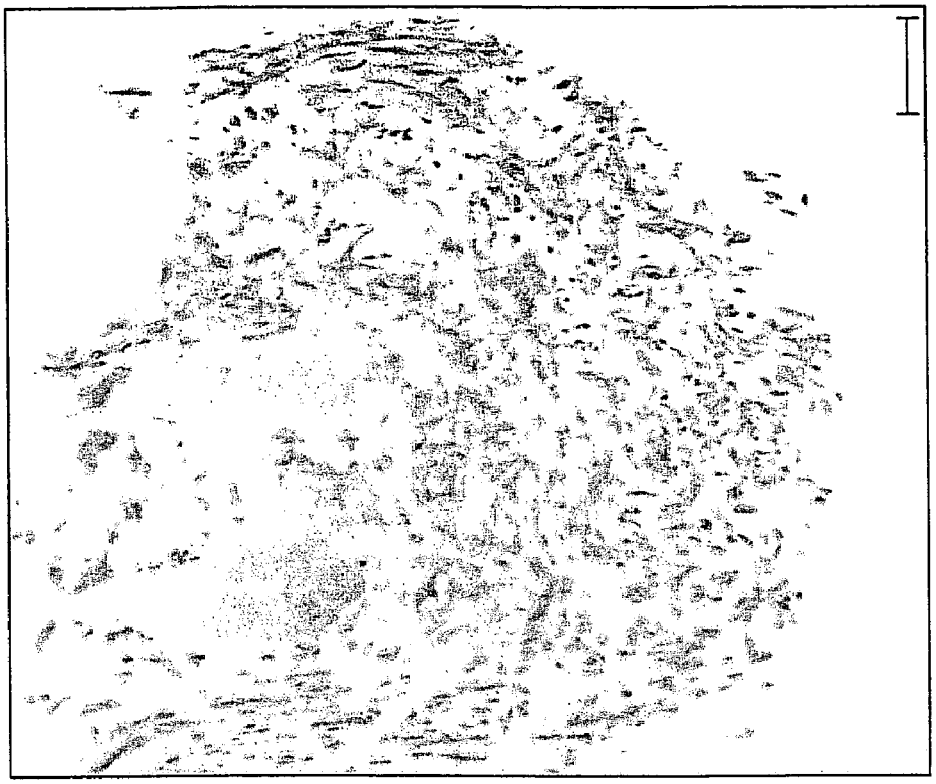
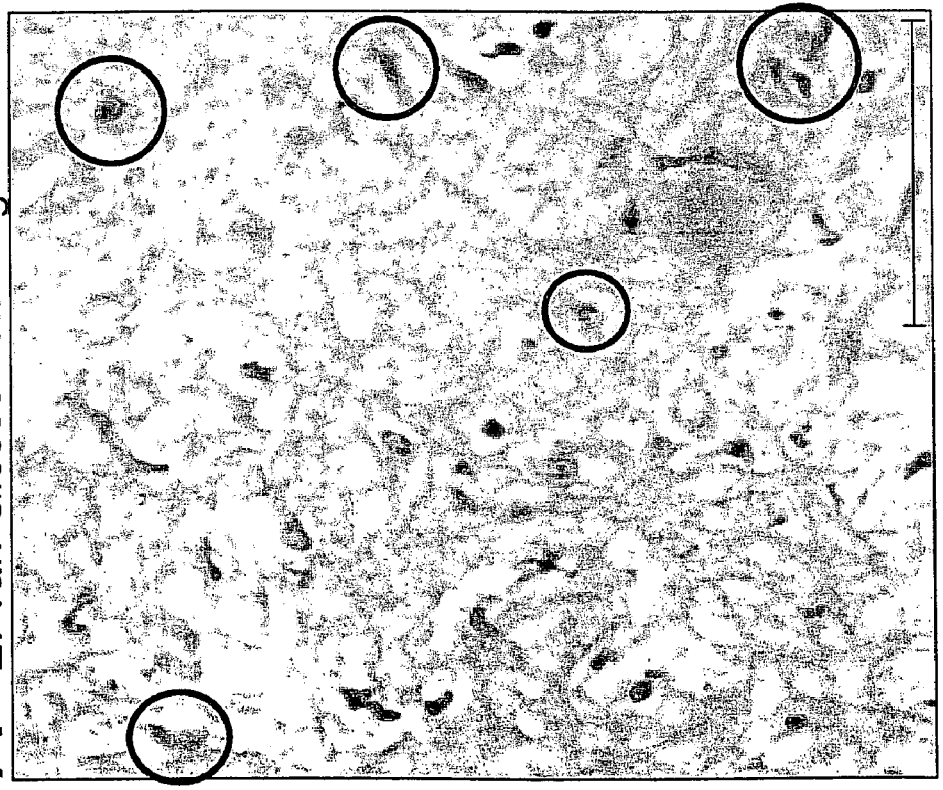

Fig. 9
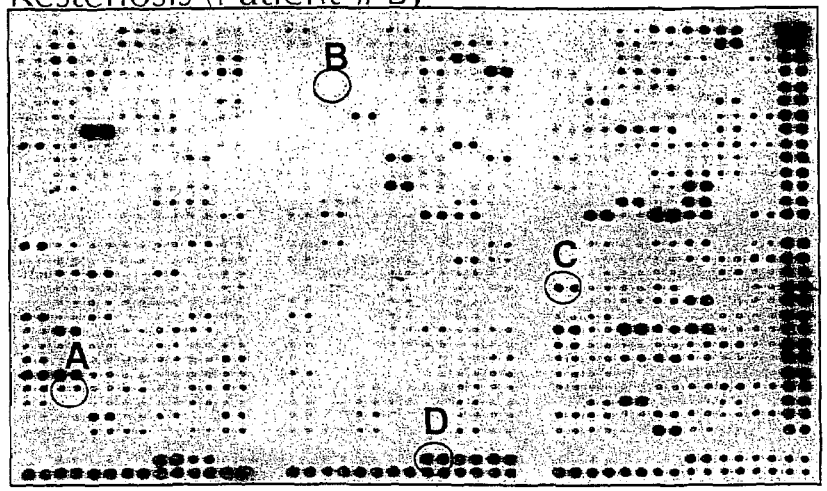
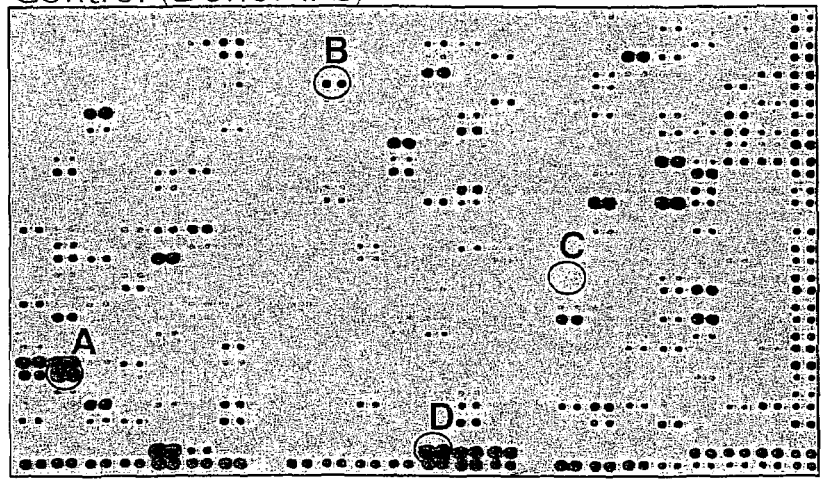
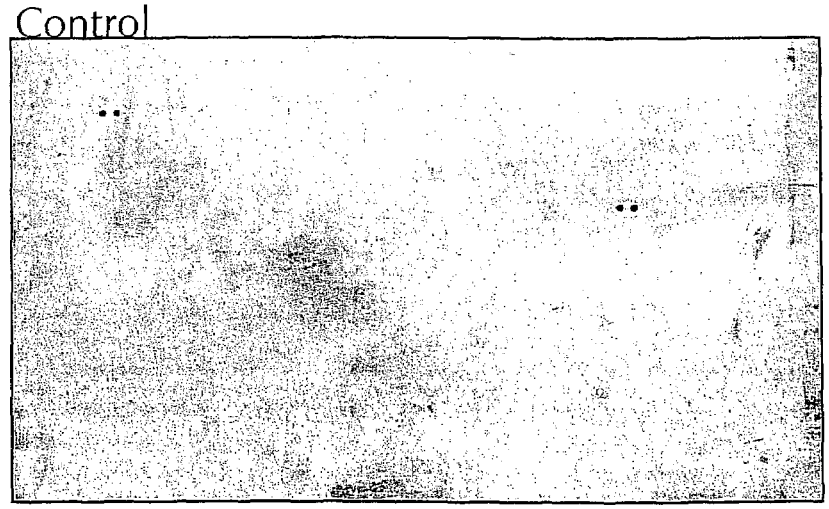

Fig. 10 cont.

| Gene/Protein | Restenosis | | | | | | | | | | | Control | | | | | | | | | | |
|---|---|---|---|---|---|---|---|---|---|---|---|---|---|---|---|---|---|---|---|---|---|---|
| Patient/Donor | A | B | C | D | E | F | G | H | I | K | | a | b | c | d | e | f | g | h | i | k |
| vascular endothelial growth factor receptor 2 | | | | | | | | | | | | | | | | | | | | | |
| prostaglandin G/H synthase 1 | | | | | | | | | | | | | | | | | | | | | |
| atrial natriuretic peptide receptor A | | | | | | | | | | | | | | | | | | | | | |
| atrial natriuretic peptide receptor B | | | | | | | | | | | | | | | | | | | | | |
| atrial natriuretic peptide receptor C | | | | | | | | | | | | | | | | | | | | | |
| desmin | | | | | | | | | | | | | | | | | | | | | |
| neuropeptide Y receptor type 1 | | | | | | | | | | | | | | | | | | | | | |
| activin receptor type I | | | | | | | | | | | | | | | | | | | | | |
| CD44 antigen epithelial form precursor | | | | | | | | | | | | | | | | | | | | | |
| mammary-derived growth inhibitor | | | | | | | | | | | | | | | | | | | | | |
| CC chemokine receptor type 2 | | | | | | | | | | | | | | | | | | | | | |
| interleukin-13 receptor alpha-1 subunit | | | | | | | | | | | | | | | | | | | | | |
| advanced glycosylation end product-specific receptor | | | | | | | | | | | | | | | | | | | | | |
| endothelial cell protein C/APC receptor | | | | | | | | | | | | | | | | | | | | | |
| vascular endothelial cell growth factor 165 receptor 2 | | | | | | | | | | | | | | | | | | | | | |
| vascular endothelial cell growth factor 165 receptor | | | | | | | | | | | | | | | | | | | | | |
| vascular endothelial growth factor receptor 1 | | | | | | | | | | | | | | | | | | | | | |
| P2Y purinoceptor 7 | | | | | | | | | | | | | | | | | | | | | |

  

Fig. 14

A Group I p Wilcoxon | Neointima Control CASMC Blood (mean)

| Adhesion, Cytoskeleton and ECM | |
|---|---|
| platelet membrane glycoprotein IIB | 0,000 |
| collagen 6 alpha 2 | 0,000 |
| CD100 | 0,001 |
| P-selectin | 0,001 |
| P2X purinoceptor 5 | 0,001 |
| neurogranin: RC3 | 0.001 |
| endothelin 2 | 0,003 |
| cadherin 16 | 0,005 |
| bikunin | 0,010 |
| lipocalin 2 | 0,012 |
| MT4-MMP | 0,013 |
| rab geranylgeranyl transferase beta subunit | 0.016 |
| SEC7 homolog B2-1 | 0,017 |
| ICAM2 | 0,018 |
| IL8-related receptor DRY12 | 0,018 |
| rab geranylgeranyl transferase alpha subunit | 0.022 |

| Proliferation and Apoptosis | |
|---|---|
| platelet- derived endothelial cell growth factor | 0,000 |
| replication protein A 70-kDa subunit | 0,000 |
| platelet-derived growth factor A | 0,001 |
| Bruton's tyrosine kinase | 0,001 |
| endothelial differentiation gene 1 | 0,001 |
| interferon-induced 56-kDa protein | 0.002 |
| ribonuclease 6 | 0,002 |
| death-associated protein 1 (DAP-1) | 0,003 |
| manic fringe | 0,003 |
| estrogen-related receptor alpha | 0,004 |
| farnesyltransferase beta | 0,004 |
| transcription factor Spi-B | 0,004 |
| caspase-1 | 0,005 |
| angiotensinogen | 0,005 |
| nuclear receptor-related 1 | 0,006 |
| interferon-inducible protein 9-27 | 0.007 |
| v-erbA related protein | 0,008 |
| histone H4 | 0,012 |
| RFC4 | 0,012 |
| G protein-coupled receptor EDG4 | 0,012 |
| SH3-binding protein 2 | 0,012 |
| sonic hedgenog | 0,013 |
| ISGF3-G | 0,014 |
| phosphoribosyl pyrophosphate synthetase subunit I | 0,014 |
| insulin receptor | 0,017 |
| atrial natriuretic peptide receptor B | 0,028 |
| interferon gamma receptor beta | 0.030 |

Fig. 14 cont.

A Group I

| | p Wilcoxon | Neointima Control CASMC Blood mean |
|---|---|---|
| Inflammation | | |
| vitamin K-dependent protein S | 0,000 | |
| alpha-2-antiplasmin | 0,001 | |
| coagulation factor XII | 0,001 | |
| prothrombin | 0,001 | |
| MHC class II HLA-DR-beta | 0,002 | |
| CD40 | 0,011 | |
| interleukin-6 receptor alpha | 0,027 | |

| | | |
|---|---|---|
| Others | | |
| specific 116-kDa vacuolar proton pump | 0,000 | |
| alpha-galactosidase A | 0,000 | |
| peroxisomal bifunctonal enzyme | 0,000 | |
| glycerol kinase | 0,000 | |
| carboxypeptidase N | 0,000 | |
| phenol sulfating sulfotransferase 1 | 0.001 | |
| apolipoprotein E | 0,017 | |
| low-density lipoprotein receptor LR11 | 0,021 | |
| lysosomal pro-X carboxypeptidase | 0,021 | |
| glutathion-S-transferase (GST) homolog | 0.026 | |

Fig. 14 cont.

B Group II p Wilcoxon | Neointima | Control | CASMC | Blood (mean)

| Adhesion, Cytoskeleton and ECM | |
|---|---|
| platelet membrane glycoprotein IIIA | 0,000 |
| migration inhibitory factor-related protein 14 | 0,000 |
| amiloride-sensitive epithelial sodium channel ß | 0,000 |
| rho GDP dissociation inihibitor 2 | 0,000 |
| paxillin | 0,001 |
| CD13 | 0,001 |
| macrosialin | 0,001 |
| p21-rac2 | 0,003 |
| CDC42 | 0.004 |
| thrombospondin 1 | 0,007 |
| versican core protein | 0,009 |
| caveolin 3 | 0,014 |
| ICAM1 | 0,014 |
| ras-related protein RAB5A | 0,014 |
| calcium & integrin-binding protein | 0,018 |
| cytokeratin 18 | 0,030 |
| CDC42 homolog | 0,004 |
| rho-related GTP-binding protein | 0,030 |
| GAP junction alpha-1 protein / connexin43 | 0,030 |

| Proliferation and Apoptosis | |
|---|---|
| osteoclast stimulating factor | 0,000 |
| FKBP12 | 0,000 |
| ets domain protein elk-3 | 0,004 |
| CDC42 | 0.004 |
| SCGF-beta | 0,004 |
| PIG7 | 0,007 |
| interferon gamma receptor | 0.009 |
| high mobility group protein (HMG-I) | 0,018 |
| E2F1 | 0,010 |
| growth factor receptor-bound protein 2 | 0,018 |
| RalB GTP-binding protein | 0,018 |
| fli-1 oncogene | 0,022 |

Fig. 14 cont.

B Group II

|  | p Wilcoxon | Neointima | Control | CASMC | Blood |
|---|---|---|---|---|---|
| Inflammation | | | | | |
| prostaglandin GH synthetase 1 | 0.001 | | | | |
| superoxide dismutase 2 | 0,001 | | | | |
| C5a anaphylatoxin receptor | 0,001 | | | | |
| lipoprotein-associated coagulation inhibitor | 0,003 | | | | |
| heat shock cognate 71-kDa protein | 0,008 | | | | |
| heme oxygenase 1 | 0,009 | | | | |
| RELB | 0,019 | | | | |
| PH-20 homolog | 0,027 | | | | |

|  | p Wilcoxon | Neointima | Control | CASMC | Blood |
|---|---|---|---|---|---|
| Others | | | | | |
| estradiol 17 beta-dehydrogenase 1 | 0,006 | | | | |
| hydroxyacyl-CoA dehydrogenase | 0,004 | | | | |
| steroid 5-alpha reductase 1 | 0,021 | | | | |
| cholesteryl ester hydrolase | 0,025 | | | | |

Fig. 14 cont.

C Group III

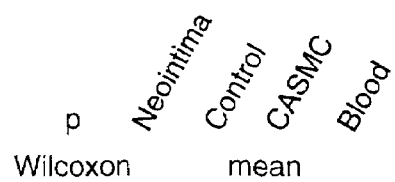

p Wilcoxon    mean

| Adhesion, Cytoskeleton and ECM | |
|---|---|
| platelet basic protein | 0,000 |
| migration inhibitory factor-related protein 8 | 0,000 |
| L-selectin | 0,000 |
| high-affinity interleukin 8 receptor A | 0.000 |
| alpha-1-antitrypsin | 0,000 |
| proline-rich tyrosine kinase 2 (PYK2) | 0,001 |
| CD18 antigen | 0,001 |
| G-protein-coupled receptor HM74 | 0,001 |
| selectin P ligand | 0,001 |
| CD11B antigen | 0,001 |
| ICAM3 | 0,001 |
| coronin-like protein P57 | 0,002 |
| platelet endothelial cell adhesion molecule | 0,009 |
| matrix metalloproteinase 9 | 0,012 |
| CXCR4 | 0,012 |
| ninjurin 1 | 0.032 |
| integrin beta 7 | 0,015 |

| Proliferation and Apoptosis | |
|---|---|
| c-src kinase | 0,000 |
| DNAX activation protein 12 | 0,000 |
| ephrin A receptor 4 | 0,000 |
| TRAIL receptor 3 | 0,001 |
| ribosomal protein S6 kinase II alpha 1 (RSK1) | 0,004 |
| phospholipase C beta 2 | 0,006 |
| BCL-2 binding athanogene-1 (BAG-1) | 0,007 |
| vav oncogene | 0,012 |
| APO-2 ligand | 0.012 |
| BCL-2-related protein A1 | 0,012 |
| 80-kDa nuclear cap-binding protein | 0,015 |
| interferon regulatory factor 7 | 0,015 |
| gamma interferon inducible protein IP30 | 0.015 |
| signaling inositol polyphosphate 5 phosphatase | 0.033 |
| activator 1 140-kDa subunit | 0.035 |
| pim-1 proto-oncogene | 0,016 |

Fig. 14 cont.

C Group III

| Inflammation | p Wilcoxon | Neointima / Control / CASMC / Blood mean |
|---|---|---|
| GM-CSF receptor alpha | 0,000 | |
| HLA class II histocompatibility antigen alpha | 0,000 | |
| lymphotoxin-beta | 0,000 | |
| interleukin-2 receptor gamma | 0,000 | |
| leukocyte IgG receptor | 0,000 | |
| low affinity immunoglobulin gamma FC receptor II-A | 0,000 | |
| myeloid cell nuclear differentiation antigen | 0,000 | |
| heat shock 70-kDa protein 6 | 0,001 | |
| allograft inflammatory factor 1 | 0,001 | |
| granulocyte colony stimulating factor receptor | 0,001 | |
| protein-tyrosine phosphatase 1C | 0,001 | |
| C-fgr proto-oncogene | 0,001 | |
| lymphocyte antigen | 0,001 | |
| rho-GAP hematopoietic protein C1 | 0,001 | |
| FC-epsilon-receptor gamma | 0,001 | |
| CD3 | 0,001 | |
| lymphokine LAG2 | 0,001 | |
| p47-PHOX | 0,002 | |
| cytidine deaminase | 0,002 | |
| proto-oncogene tyrosine-protein kinase lck | 0,004 | |
| platelet activating factor receptor | 0,004 | |
| macrophage colony stimulating factor 1 receptor | 0.004 | |
| tyrosine-protein kinase lyn | 0,012 | |
| FMLP-related receptor I | 0,012 | |
| interleukin-16 | 0,012 | |
| interleukin-1 receptor type II | 0,012 | |
| lymphoid restricted homolog of SP100 protein | 0.005 | |
| IgG receptor FC large subunit P51 | 0,019 | |

| Others | | |
|---|---|---|
| clone 23815 | 0,001 | |
| brain glucose transporter 3 | 0,004 | |
| hormone-sensitive lipase | 0,016 | |
| IMP-dehydrogenase 1 | 0.027 | |

Fig. 14 cont.

D Group IV

| | p Wilcoxon | Neointima Control CASMC Blood mean |
|---|---|---|
| Adhesion, Cytoskeleton and ECM | | |
| MUC18 | 0,000 | |
| integrin alpha 7B | 0,000 | |
| collagen 16 alpha 1 | 0,000 | |
| tenascin | 0,002 | |
| collagen 6 alpha 1 | 0,004 | |
| desmin | 0,000 | |
| peripheral myelin protein 22 | 0,001 | |
| cytokeratin 6A | 0,002 | |
| dual-specificity A-kinase anchoring protein 1 | 0,003 | |
| homeobox protein HOXB7 | 0,003 | |
| myotonin-protein kinase | 0,008 | |
| microtubule-associated protein 1B | 0,014 | |
| collagen 18 alpha 1 | 0,005 | |
| S100 calcium-binding protein A1 | 0,001 | |
| integrin alpha 8 (ITGA8) | 0,005 | |
| P2X purinoceptor 1 | 0,007 | |
| cell adhesion kinase | 0,005 | |
| integrin alpha 3 | 0,021 | |

| Inflammation | | |
|---|---|---|
| alpha-2-macroglobulin | 0,001 | |
| extracellular superoxide dismutase | 0,001 | |
| inter-alpha-trypsin inhibitor heavy chain H4 | 0,007 | |

| Others | | |
|---|---|---|
| adenylate kinase isoenzyme 1 | 0,025 | |
| carboxypeptidase H | 0,018 | |
| autosomal dominant polycystic kidney disease II | 0,000 | |
| PC8 convertase | 0,000 | |
| adipocyte fatty acid-binding protein 4 | 0,001 | |
| brain-specific polypeptide PEP-19 | 0,004 | |

Fig. 14 cont.

D Group IV

| Proliferation and Apoptosis | p Wilcoxon |
|---|---|
| neurotrophic tyrosine kinase receptor-related 3 | 0,000 |
| insulin-like growth factor binding protein 6 | 0,001 |
| early growth response protein 1 | 0,001 |
| tuberin | 0,001 |
| metallothionein-III | 0,001 |
| GADD45 beta | 0,002 |
| collagen 18 alpha 1 subunit (COL18A1) | 0.021 |
| NT-3 growth factor receptor | 0,003 |
| RAD1 | 0,003 |
| frizzled-related FrzB FRITZ | 0,003 |
| insulin-like growth factor 1 receptor (IGF1R) | 0.021 |
| G1/S-specific cyclin D1 | 0,003 |
| c-fos proto-oncogene | 0,003 |
| early response protein NAK1 | 0,004 |
| neurogenic locus notch protein | 0,005 |
| RYK | 0,005 |
| mammary-derived growth inhibitor | 0,007 |
| CBL-B | 0,007 |
| cyclin-dependent kinase inhibitor 1 | 0,009 |
| high-affinity nerve growth factor receptor | 0,011 |
| purine-rich single-stranded DNA-binding prot. alpha | 0,011 |
| p16-INK4 | 0,011 |
| serum response factor | 0,013 |
| NuMA | 0,014 |
| guanine nucleotide-binding protein G(Y) alpha 11 | 0,015 |
| BIGH3 | 0,015 |
| VEGF B + VRF186 | 0,016 |
| insulin-like growth factor I receptor | 0,017 |
| P126 | 0,023 |
| GADD45 gamma | 0,023 |

Fig. 17
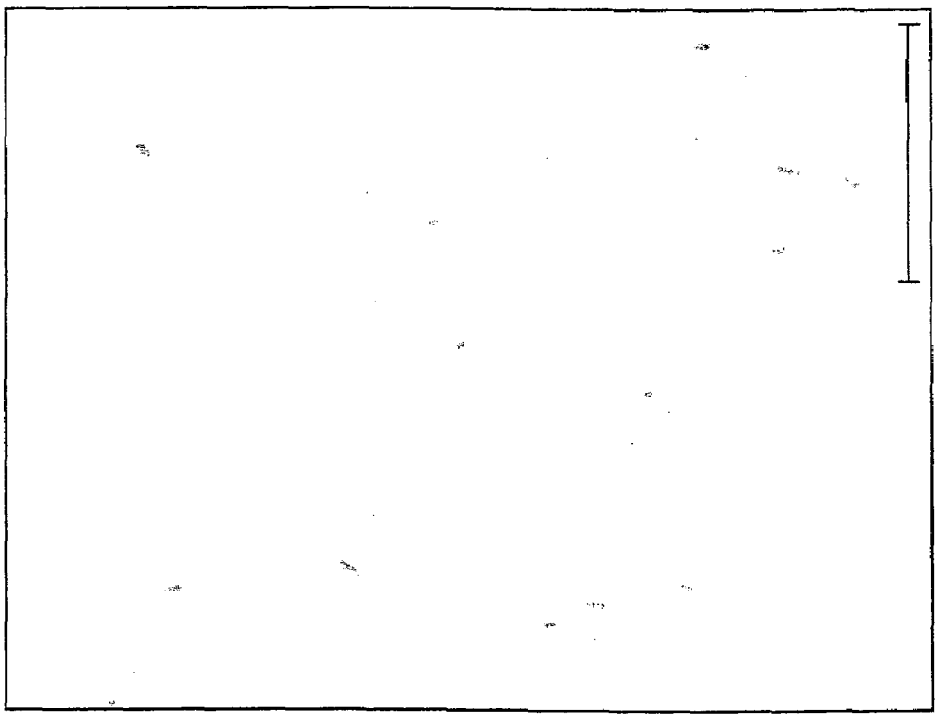

Screening of colonies by southern blot using driver and tester as probe
1 2 3 4 5 6 7 8 9 M
Driver
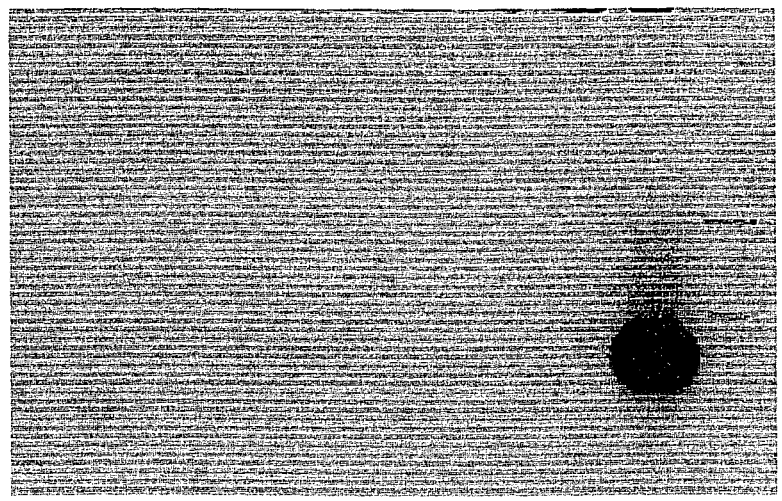
Tester
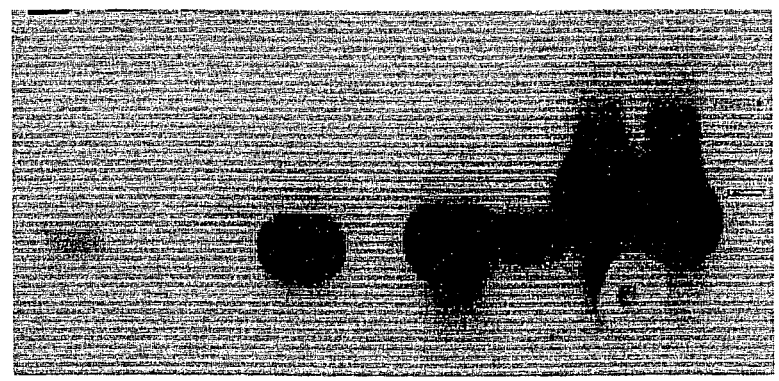
Fig. 25

Differential expression of ESE1

1 - 4: single breast cancer cells
5-7: bone marrow of healthy donors

SEQUENCE LISTING

```
<160> NUMBER OF SEQ ID NOS: 40

<210> SEQ ID NO 1
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(17)
<223> OTHER INFORMATION: N can be a, c, g or t

<400> SEQUENCE: 1 ccccccccc cnnnnnn                                                    17

<210> SEQ ID NO 2
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(21)
<223> OTHER INFORMATION: N can be a, c, g or t

<400> SEQUENCE: 2
cttatacgga tatccnnnnn n                                              21

<210> SEQ ID NO 3
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (25)..(30)
<223> OTHER INFORMATION: N can be a, c, g or t

<400> SEQUENCE: 3
cgatgatcta gataggtaca agtcnnnnnn                                     30

<210> SEQ ID NO 4
<211> LENGTH: 28
<212> TYPE: DNA
<213> ORGANISM: Artificial Sequence
```

```
<220> FEATURE:
<223> OTHER INFORMATION: Primer
<220> FEATURE:
<221> NAME/KEY: misc_feature
<222> LOCATION: (23)..(28)
<220> FEATURE:
<221> NAME/KEY: misc_feature
<222> LOCATION: (23)..(28)
<223> OTHER INFORMATION: n is a, c, g, or t

<400> SEQUENCE: 4
ctgtagcagc cgtctagacg tcnnnnnn                                28

<210> SEQ ID NO 5
<211> LENGTH: 40
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (35)..(40)
<220> FEATURE:
<221> NAME/KEY: misc_feature
<222> LOCATION: (35)..(40)
<223> OTHER INFORMATION: n is a, c, g, or t

<400> SEQUENCE: 5
tttttttttt ttctgtagca gccgtctaga cgtcnnnnnn                   40

<210> SEQ ID NO 6
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (34)..(39)
<223> OTHER INFORMATION: N can be a, c, g or t

<400> SEQUENCE: 6
tttctcctta atgtcacaga tctcgaggat ttcnnnnnn                    39

<210> SEQ ID NO 7
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(28)
<223> OTHER INFORMATION: N can be a, c, g or t

<400> SEQUENCE: 7
cccccccccc ccccggtcta gannnnnn                                28

<210> SEQ ID NO 8
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(28)
<223> OTHER INFORMATION: N can be a, c, g or t

<400> SEQUENCE: 8
```

```
cccccccccc ccccgtctca gannnnnn                                    28
```

<210> SEQ ID NO 9
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(30)
<223> OTHER INFORMATION: N can be a, c, g or t

<400> SEQUENCE: 9

```
cccccccccc ccccgtctca gannnnnnnn                                  30
```

<210> SEQ ID NO 10
<211> LENGTH: 39
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (39)..(39)
<223> OTHER INFORMATION: N can be a, c, g or t

<400> SEQUENCE: 10

```
cccccccccc ccccgtctca gatttttttt tttttttvn                        39
```

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11

```
acgttatgga tccccccccc cc                                          22
```

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12

```
tcagaattca tgcccccccc cccc                                        24
```

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13

```
tcagaattca tgcccccccc cccccc                                      26
```

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14

```
tcagaattca tgcccccccc cccccc                                        27

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
gctgaagtgg cgaattccga tgcccccccc cccccc                             36

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
ctccttaatg tcacagatct cgaggatttc                                    30

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
acgattccct gatgaggcag                                               20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
ccatcttcac gttgagcagg                                               20

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
ctgagacgcc atctgtaggc ggtg                                          24

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
gtctttggct accagtccag cagc                                          24

<210> SEQ ID NO 21
<211> LENGTH: 20
<212> TYPE: DNA
```

<213> ORGANISM: Artificial Sequence
<220> FEATURE:
<223> OTHER INFORMATION: Primer

<400> SEQUENCE: 21
aagagaccac acttgtgcgg                                             20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
aatgtggtgc tgagtcgagg                                             20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
cggtgtccag ttccaatacc                                             20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
ccccatagtc caccaacatg                                             20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
atgccactct cgtcttcgat                                             20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ggaacatcag gaaaagctcc                                             20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tacaaggctg aggatgaggc                                             20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
cttcccgaca cttgtcttgc                                                   20

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
ctacgtcgcc ctggacttcg agc                                               23

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
gatggagccg ccgatccaca cgg                                               23

<210> SEQ ID NO 31
<211> LENGTH: 44
<212> TYPE: DNA
<213> ORGANISM: Artificial Sequence
<220> FEATURE:
<223> OTHER INFORMATION: Primer

<400> SEQUENCE: 31
gtaatacgac tcactatagg gctcgagcgg ctcgcccggg cagg                        44

<210> SEQ ID NO 32
<211> LENGTH: 12
<212> TYPE: DNA
<213> ORGANISM: Artificial Sequence
<220> FEATURE:
<223> OTHER INFORMATION: Primer

<400> SEQUENCE: 32
aattcctgcc cg                                                           12

<210> SEQ ID NO 33
<211> LENGTH: 43
<212> TYPE: DNA
<213> ORGANISM: Artificial Sequence
<220> FEATURE:
<223> OTHER INFORMATION: Primer

<400> SEQUENCE: 33
tgtagcgtga agacgacaga aaggtcgcgt ggtgcggagg gcg                         43

<210> SEQ ID NO 34
<211> LENGTH: 12
<212> TYPE: DNA
<213> ORGANISM: Artificial Sequence
<220> FEATURE:

<223> OTHER INFORMATION: Primer

<400> SEQUENCE: 34
aattcgccct cc    12

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
gtaatacgac tcactatagg gctcgagcgg    30

<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36
tgtagcgtga agacgacaga aggtcgcgt    30

<210> SEQ ID NO 37
<211> LENGTH: 33
<212> TYPE: DNA
<213> ORGANISM: Artificial Sequence
<220> FEATURE:
<223> OTHER INFORMATION: Primer

<400> SEQUENCE: 37
gtaatacgac tcactatagg gctcgagcgg ctc    33

<210> SEQ ID NO 38
<211> LENGTH: 33
<212> TYPE: DNA
<213> ORGANISM: Artificial Sequence
<220> FEATURE:
<223> OTHER INFORMATION: Primer

<400> SEQUENCE: 38
tgtagcgtga agacgacaga aggtcgcgt ggt    33

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39
cgactcacta tagggctcga gcggctcgcc    30

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
gtgaagacga cagaaaggtc gcgtggtgcg    30

MRNA AMPLIFICATION

CROSS REFERENCE TO RELATED APPLICATIONS

This application is a national phase application of PCT/EP01/03311 filed Mar. 23, 2001, which claims priority to EP 00 10 6450.0 filed Mar. 24, 2000, which are incorporated in their entirety by reference.

BACKGROUND OF THE INVENTION

1. Field of the Invention

The present invention relates to a method for the amplification of mRNA of a sample, comprising the steps of i.) generating cDNA from polyadenylated RNA employing at least one primer hybridizing to said polyadenylated RNA and comprising a 5' poly(C) or a 5' poly(G) flank; ii.)(aa) if present, removing non-hybridized, surplus primer(s) and/or surplus dNTPs; ii.)(ab) 3' tailing of said generated cDNA with a poly(G) tail when in step i. (a) primer(s) comprising a 5' poly(C) flank was employed or a poly(C) tail when in step i. (a) primer(s) comprising a 5' poly(G) flank was employed; or ii.)(b) 3' tailing of said generated cDNA with a poly(G) tail when in step i. (a) primer(s) comprising a 5' poly(C) flank was employed or a poly(C) tail when in step i. (a) primer(s) comprising a 5' poly(G) flank was employed using an RNA-ligase, irrespective of the presence or absence of surplus primer(s) and/or surplus dNTPs; and iii.) amplifying the tailed cDNA with a primer hybridizing to the tail(s) generated in step ii(ab) or ii(b). Furthermore, the present invention relates to methods for the preparation of in vitro surrogate(s), for identifying expressed genes in a test sample, for identifying a drug candidate for therapy of a pathological condition and for in vitro detection of a pathological condition employing said method for amplification of mRNA. In addition, the present invention relates to the use of amplified cDNA(s) as obtained by the method of the invention in hybridization, interaction and/or enzymatic arrays.

2. Description of the Related Art

Several documents are cited throughout the text of this specification. The disclosure content of each of the documents (including any manufacturer's specifications, instructions, etc.) is herewith incorporated by reference.

The study of gene expression and gene expression patterns have lately been revolutionized by global analysis of mRNA expression on cDNA filter assays or cDNA micro arrays (see, inter alia, Southern, Trends Genet. 12 (1996), 110–115; Debouck, Nat. Genet. 21:48–50 (1999); Hacia, Nat. Genet., 21, 42–7 (1999); Cole, Nat. Genet. 21, 38–41 (1999); Bowtell D D., Nat. Genet., 21, 25–32 (1999); Cheung, Nat. Genet., 21, 15–19 (1999); Duggan, Nat. Genet., 21, 10–14 (1999); Southern, Nat. Genet., 21, 5–9 (1999)). For example, Lockhart (Nature Biotechnology 14 (1996), 1675–1680) describes an approach that is based on hybridization of a large number of mRNAs to small, high-density arrays containing tens of thousands of synthetic oligonucleotides, allowing for the simultaneous monitoring of tens of thousands of (expressed) genes. Further micro arrays for gene expression have been described in Shalon (Pathol. Biol. 46 (1998), 107–109), Lockhardt (Nuc. Acids Symp. Ser. 38 (1998), 11–12) or in Schena (Trends Biotech. 16 (1998), 301–306). However, one of the major draw-backs of the above described cDNA-array technology is the fact that these technologies require an amount of 2.5 to 10 μg of nucleic acid probes to be tested either in the form of mRNA, reverse transcribed RNA or amplified cDNA (see, inter alia, Schena (Science 270 (1995), 467–470 and PNAS U.S.A. 93 (1996), 10614–10619) or Lockhardt (1996) loc. cit.). This amount of material is normally only derived from a large of number of cells such as about $10^9$. Bryant, PNAS U.S.A. 96 (1999), 5559–5564 or Mahadevappa, Nat. Biotech. 17 (1999), 1134–1136 reported such an approach using at least from 50000 cells. The smallest number of cells yet used for ex-vivo tissue analysis and corresponding gene expression has been 1,000 cells (Luo, Nat. Medicine 5 (1999), 117–122). However, a plethora of physiological and/or pathological conditions would require to study the gene expression pattern or "transcriptome", defined as the entirety of mRNA molecules in a given biological sample (Velculescu, Cell, 88, 243–251 (1997) of a lower number of cells or even a single cell. For instance, the investigation of spatially and temporally regulated gene expression in embryogenesis would clearly profit from a method were a low number of cells, in particular a single cell, can be deduced. Similarly, it would be of high interest to investigate the gene expression pattern/transcriptome of individual cells or a low number of cells derived from adult tissue, like, inter alia, blood or neuronal (stem) cells. Furthermore, multiple pathological conditions could be clarified, e.g., the delineation of deregulated gene expression in a typical proliferation, mutaplasia, preneoplastic lesians and/or carcinomata in situ. Other examples of locally restricted pathological processes which could be investigated comprise, but are not limited to, restenosis, Alzheimer's disease, Parkinson's disease, graft-versus-host disease or inflammations in autoimmunity. Furthermore, occult micrometastasis derived from a small cancer has dire consequences if the disseminated tumor cells survive in distant organs and grow into manifest metastases. Tumor cells left after resection of primary tumors are currently detected in bone marrow aspirates by immunocytochemical staining with antibodies directed against cytokeratins (reviewed in Pantel, J. Natl. Canc. Inst. 91, 1113–1124 (1999)). While several studies have established the prognostic significance of cytokeratin-positive micrometastatic cells in bone marrow (Braun, N. Engl. J. Med. 342, 525–533 (2000); Pantel, J. Natl. Canc. Inst. 91, 1113–1124 (1999)), the biology of these cells has largely remained enigmatic because of their extremely low frequency in the range of $10^{-5}$–$10^{-6}$.

The systemic spread of cancer cells requires that cells evade from the solid tumor, distribute via blood or lymphatic vessels, cross endothelial and tissue barriers and survive ectopically as single cells. The phenotypic changes accompanying these steps are considered a developmental process, the so-called epithelial-mesenchymal transformation (EMT) (Hay, Acta Anatomica, 154, 8–20, (1995); Birchmeier, Acta Anatomica, 156, 217–226 (1996)). Only a small fraction of cells disseminated from a tumor may acquire EMT-associated features (Boyer, Acta Anatomica, 156, 227–239 (1996)). The epigenetic changes leading to EMT are not known so far but may have important implications for the development of future therapies.

Major technical hurdles in studying epigenetic changes of, e.g., disseminated tumor cells or pathological modified tissue are limited accessibility, low frequency, unambiguous identification, and subsequent transcriptome analysis at a single cell level or of a low number of cells. A variety of protocols has been developed for the generation of "single cell cDNA libraries" and the global amplification of mRNA from individual cells (see Belyavsky, Nucl. Acid. Res., 17, 2919–2932 (1989); Brady, Methods in Enzymology, 225, 611–623 (1993); and Karrer, Proc. Natl. Acad. Sci. USA, 92, 3814–3818 (1995)). However, these procedures have obvious drawbacks, such as the restriction to 3'-ends and an insufficient sensitivity when PCR amplificates are hybridized to cDNA arrays.

In these procedures, variation introduced during amplification of cDNA fragments was reduced by limiting the length of the cDNAs during reverse-transcription. This was accomplished through low substrate conditions for the reverse-transcriptase; i.e. the use of low concentrations of an oligo d(T) primer and low dNTP concentrations. However, there is a risk of compromising reverse-transcription and subsequent PCR-efficiency which may lead to arbitrary results when transcriptome/gene expression patterns of cells/single cells are to be investigated. Furthermore, the use of an oligo(dT) primer for PCR amplification limits the use of high annealing temperatures and thus stringent annealing conditions. Typically, annealing is performed at 42° C. (Brail, Mut. Res. Genomics 406 (1999), 45–54). As pointed out hereinabove, such an approach may be suitable for a 3' restricted cDNA synthesis. However, higher annealing temperatures reduce the presence of secondary structures in the cDNA and the likelihood of unspecific annealing to internal sequences of the cDNA, which would result in shortening of the amplificates compared to the cDNA molecules. Annealing temperatures of the method of the invention are preferably above 45° C., more preferably above 55° C., even more preferably above 65° C.

As mentioned hereinabove, the amount of mRNA in a low number of cells or even a single cell is insufficient for use in direct global analysis. Therefore, global analysis of expressed mRNA (of a "transcriptome") from a low number of cells or even an individual, single cell requires amplification of extracted and/or reverse transcribed polyadenylated mRNA. To date, PCR amplification of small amounts of mRNA has not resulted in reliable representation of the relative expression of mRNA present in a certain cell/low number of cells at a specific timepoint, a specific developmental state and/or a specific physiological state (Brail, Mut. Res. Genomics 406 (1999), 45–54), Brail (1999), (loc. cit.) conclude that the method as described by Brady (Brady (1993) (loc. cit.) is likely to introduce variation(s) in the tailing reaction or the PCR amplification steps. In particular, Brail's analysis (Brail (1999), loc. cit) showed a five-fold variation even for highly-abundant house-keeping genes (direct comparison of GAPDH and ribosomal gene L32).

Thus, the technical problem of the present invention consists in providing means and methods which comply with the need of a global and uniform amplification of mRNA, in particular of the transcriptome of a low number of cells or a single cell. The solution to this technical problem is achieved by providing the embodiments characterized in the claims.

BRIEF SUMMARY OF INVENTION

Accordingly, present invention relates to a method for amplification of mRNA of a sample, comprising the steps of
(i) generating cDNA from polyadenylated RNA employing at least one primer hybridizing to said polyadenylated RNA and comprising a 5' poly(C) or a 5' poly(G) flank;
(ii)(aa) if present, removing non-hybridized, surplus primer(s) and/or surplus dNTPs;
   (ab) 3' tailing of said generated cDNA with a poly(G) tail when in step i. (a) primer(s) comprising a 5' poly(C) flank was/were employed or a poly(C) tail when in step i. (a) primer(s) comprising a 5' poly(G) flank was/were employed; or (b) 3' tailing of said generated cDNA with a poly(G) tail when in step i. (a) primer(s) comprising a 5' poly(C) flank was/were employed or a poly(C) tail when in step i. (a) primer(s) comprising a 5' poly(G) flank was/were employed using an RNA-ligase, irrespective of the presence or absence of surplus primer(s) and/or surplus dNTPs; and
(iii) amplifying the tailed cDNA with a primer hybridizing to the tail(s) generated in step (ii)(ab) or (ii)(b).

Polyadenylated RNA can be obtained from a sample by methods known in the art. These methods comprise oligo (dT) selection steps. The sample may be of animal or plant origin and may be a tissue or a cell sample. Said sample may also comprise cultured tissue(s) or cultured cell(s). Particularly preferred is a sample of human origin. Samples may be obtained by methods known in the art, which comprise, but are not limited to atherectomy, debulking, biopsy, laser dissection or macroscopic surgical procedures.

The here described technique and method for amplification of mRNA from said sample comprises steps, wherein said polyadenylated RNA obtained from a sample is employed for the generation of (a) first cDNA product(s) employing (a) primer(s) comprising 5'-oligo (dC)/poly (C) (-or 5'-oligo (dG)/poly (G)) flanking regions. Said 5'-oligo (dC) or 5'-oligo (dG) primer preferably comprises between 8 and 20 cytosine (or guanine) nucleotides, more preferably 10 cytosine (or guanine) nucleotides, more preferably said primer(s) comprise(s) 11, even more preferably said primer(s) comprise(s) 13, most preferably said primer(s) comprise(s) 15 cytosine (or guanine) nucleotides. It is preferred that the first cDNA synthesis is carried out after potentially contaminating tRNAs or rRNAs have been removed. Such a removal can be carried out by methods known to the skilled artisan, for example, by binding the polyadenylated mRNA to oligo (dT)/poly(T)-coated solid supports as defined herein and subsequent washing steps.

Furthermore, this first cDNA synthesis step comprises preferably random primers which are present in a concentration which is 2,000 to 8,000 times higher than primer concentrations used in previous studies (for example, of 10 nM as employed in Trumper, Blood 81 (1993), 3097–3115). It is furthermore preferred that said first cDNA synthesis, i.e. the generation of cDNA from polyadenylated RNA, is carried out in a correspondingly high concentration of dNTPs, preferably in a concentration of 0.5 mM dNTPs. This first cDNA preparation step (step "i") may also comprise means for labeling the resulting cDNA. Labels may be introduced by methods known to the skilled artisan (see, inter alia, "Current Protocols in Molecular Biology", edited by Ausubel et al., John Wiley & Sons, USA (1988)), and may comprise the employment of labeled dNTPs (like biotin-labeled, radio-labeled or fluorescein-labeled dNTPs). This first cDNA synthesis step (reverse transcription), employing preferably randomized primers, may comprise the use of standard enzymes, preferably RNAse H deficient reverse transcriptase, like Superscript II Reverse Transcriptase (GIBCO).

Since high dNTP concentrations improve said first cDNA synthesis but may interfere with any subsequent reactions (like tailing reactions) it is preferred that (before carrying out any further reactions and/or steps of the method of the invention) free surplus dNTPs are removed. Surplus, non-hybridized primer(s) are preferably also removed before additional steps are carried out. Said removal can be obtained, inter alia, by washing steps, like buffer exchanges (as shown in the appended examples), or by filtration methods (i.e. over size-selective membranes). However, said removal step can also be omitted should no surplus of dNTPs and/or primers be present. Furthermore, the removal step can be avoided, should the subsequent "tailing-step" be carried out by an RNA-ligase step.

The 3'-tailing reaction of the method of the present invention (see step (ii)(ab) or (ii)(b) of the method of the invention) comprises the tailing with poly(G) when in step "i" (a) primer(s) comprising a 5' poly(C) flank was/were employed or a poly(C) when in step "i" (a) primer(s) comprising a 5' poly(G) flank was/were employed. As demonstrated in the appended examples, it has surprisingly been found that, inter alia, poly(C) primers binding to poly(G)-tails are at least 100-times more sensitive than poly (T) primers binding on poly(A) tails, as proposed in the prior art (Brady (1993), loc. cit.; Trumper, Blood, 81, 3097–3115 (1993)).

The tailing reaction may be carried out by employing an enzyme with 3' terminal deoxynucleotide transferase activity, preferably in a non-cacodylate containing storage buffer, like terminal deoxynucleotide transferase (MBI Fermentas; Pharmacia) However, it should be mentioned that said "tailing"-step can also be carried out by RNA-ligase (see: Edwards, Nucl. Acids Res., 19, 5227–5232 (1991)). In this case, oligo(dC) or oligo(dG) flanking regions may be ligated to the 3-end of the single-stranded cDNA molecules by said RNA ligase. Sequences of the flanking regions are capable of hybridizing to the flanking region of the cDNA synthesis primer(s), (Edwards, Nucl. Acid Res. 19 (1991), 5227–5232).

Finally, the polyG/polyC-tailed cDNA can be further amplified since these cDNA(s) comprise(s) a 5' primer-introduced oligo(C) (or -G) stretch and a 3' oligo(G) (or —C) stretch introduced by, e.g., terminal deoxynucleotide transferase. This second PCR reaction may be carried out in the presence of labeled nucleotides. Preferred are biotin-labeled, fluorescein-labeled, dioxygenin-labeled or radio-labeled nucleotides which are known in the art. Furthermore, it is within the scope of this invention that "tagged" oligonucleotide primers (like biotin-, fluorescein-, dioxygenin-, or radio-labeled oligonucleotide primers.) are employed in order to obtain a single tag/label per cDNA species.

In a preferred embodiment of the method of the invention, said at least one primer in step "i" is a random primer, a oligo(dT) primer or a combination thereof. Said random primer may comprise a stretch of 4 to 10 random nucleotides, preferably a stretch of 5 to 9 random nucleotides. Most preferably said random primer comprises a random hexamer or a random octamer oligonucleotide. It is particularly preferred that said random primer has a sequence as shown in SEQ ID NOs: 1–8. Even more particularly preferred is the random primer CFI5CN6, as employed in the appended examples comprising the nucleotides 5'-(CCC)$_5$GTCTAG-A(N)$_6$ (SEQ ID NO: 8).

As shown in the appended examples, said random primer(s) can also be employed in combination with other random primers or (an) oligo(dT) primer(s). For example, in step "i" of the present invention a primer pair (CFI5c8, corresponding to SEQ ID NO: 9) and (CFI5cT, corresponding to SEQ ID NO: 10) may be employed, comprising the sequences 5'-(CCC)$_5$GTCTAGA(N)$_8$ and 5'-(CCC)$_5$GTCTAGATT(TTT)$_4$TVN, wherein "V" represents G, C or A and N represents G, T, C or A. Therefore, it is particularly preferred that a combination of a poly d(C)/ (G) primer comprising an octamer (see, e.g. SEQ ID NO: 9) is employed in combination with an oligo (dT) primer (see, SEQ ID NO: 10).

Accordingly, in a further preferred embodiment of the method of the present invention, the oligo(dT) primer to be employed in step "i" has the sequence as shown in SEQ ID NO: 10, comprising the sequence 5'-(CCC)$_5$GTCTAGATT (TTT)$_4$TVN. As mentioned, hereinabove, said oligo (dT) primer(s) to be employed in step "i" of the method of the present invention can be used alone or in combination with (a) random primer(s) as described hereinabove. Said oligo (dT) primer(s) is/are preferably a primer comprising an oligo (dT) stretch.

In another preferred embodiment of the method of the present invention, the concentration of said at least one primer in step "i" is in the range of 0.01 µM to 500 µM, preferably in the range of 0.1 µM to 200 µM, more preferably in the range of 1 µM to 100 µM, even more preferably in the range of 10 µM to 60 µM. As shown in the appended example, the most preferred concentration is about 50 µM.

In yet another preferred embodiment of the method of the present invention, said primer in step "iii" comprises a stretch of at least 10, preferably at least 12, most preferably at least 15 nucleotides capable of hybridizing with the tail(s) generated in step "ii(ab)" or "ii(b)". It is preferred that said primer does not comprise more than 20 nucleotide capable of hybridizing with the tail(s) generated in step "ii(ab)" or "ii(b)" of the method of the present invention. In a preferred embodiment said primer in step "iii" has the sequence as depicted in SEQ ID NO: 11, 12, 13, 14 or 15. As shown in the appended examples a particular preferred primer in step "iii" is the primer "CP2" comprising the nucleotide sequence 5'TCAGAATTCATG(CCC)$_5$ (see SEQ ID NO: 14), with which particularly good results have been obtained in this "global amplification" step. Therefore, should a single primer be employed in this step, the above described "CP2"-primer is particularly preferred when in step "ii(ab)" or "ii(b)" a poly(G)-tailing was carried out. An advantage of employing only a single primer in step "iv" of the invention is that potential "primer-primer" interactions can be avoided and relatively high primer concentrations preferably above 0.2 µM, more preferably above 0.8 µM, even more preferably above 1,0 µM can be used. Higher primer concentrations above 1,0 µM or 1,2 µM may also be employed.

In another preferred embodiment of the method of the present invention, said polyadenylated RNA (and/or mRNA to be amplified) is bound to a solid support. Said solid support may be, inter alia, a bead, a membrane, a filter, a well, a chip or a tube. Particularly preferred is a magnetic bead, a latex bead or a colloid metal bead. However, said polyadenylated RNA may also be bound on solid supports like polystyrene beads. Solid phases known in the art also comprise glass and/or silicon surfaces, nitrocellulose strips or membranes and plastic (test) tubes. Suitable methods of immobilizing nucleic acids, in particular polyadenylated RNA on solid phases include but are not limited to ionic, hydrophobic, covalent interactions and the like. The solid phase can retain one or more additional receptor(s) like, for example, a poly (T) stretch, which has/have the ability to attract and immobilize the polyadenylated RNA. This receptor can also comprise a changed substance that is oppositely charged with respect to the nucleic acid. In a most preferred embodiment of the method of the present invention, the solid support, (like said magnetic bead) comprises therefore an oligo(dT) stretch.

As shown in the appended examples, the mRNA/poly-adenylated RNA to be amplified by the method of the present invention can easily be isolated on an oligo (dT) coated solid support, like oligo (dT) coated magnetic beads.

In yet another embodiment of the present invention the mRNA to be amplified is derived from a tissue, a low number of cells or a single cell. Said low number of cells may be in the range of $10^6$ to 2 cells. Said tissue, cells or single cell may be of plant or animal origin. It is particularly preferred that said tissue, cells or single cell is/are of human origin. Said tissue, cells or single cell may be, furthermore, a pathological sample and/or a sample which is suspected to be pathological. Whether pathological, suspected to be pathological or normal/healthy, said tissue, (low number of) cells or single cell may be derived from a body fluid or from solid tissue. Body fluids may comprise blood, lymphatic fluid, peritonal fluid, spinal/cerebrospinal fluid, amnionic fluid, urine or stool. Said solid tissue may be derived from all animal/human organs or glands. Furthermore, said tissue may comprise malignant transformations, like tumors or restenotic tissue. Therefore, said tissue, (low number of) cells, or single cells may also be from carcinomas, sarcomas, lymphomas, leukemias or gliomas. However, it should be pointed out that the method of the present invention can also be employed on samples derived from benign tissue, normal tissue as well as from cultured samples, like tissue and/or cell cultures. Tissues, low number of cells and/or single cells can be obtained by methods known in the art, which comprise, but are not limited to biopsis, aspirations or dilutions. Samples can also be separated and obtained by FACS sorting or isolation by immunological methods or "receptor/ligand" binding methods. As shown in the appended examples, samples can also be obtained by artherectomy, e.g. helical device for artherectomy (X-sizer, Endicor)

In another preferred embodiment of the method of the present invention, said tissue, low number of cells or single cell is a chemically fixed tissue, chemically fixed low number of cells or chemically fixed cell. Said fixation may be carried out in (para)formaldehyde. Preferred concentrations are in the range of 0.1 to 1%, most preferred is, however, a concentration of 0.1%. Said fixation is preferably carried out for less than 30 minutes (when concentrations below 1% are employed). Most preferably said fixation is carried out at a (para)formaldehyde concentration of 0.1% for 5 minutes.

In another preferred embodiment, the method of the present invention further comprises a step "iv" wherein the generated amplified cDNA is further modified. Said modification may comprise the introduction of means for detection, for example, the introduction of nucleotide analogues coupled to (a) chromophore(s), (a) fluorescent dye(s), (a) radio-nucleotide(s), biotin or DIG. Labeling of amplificated cDNA can be performed as described in the appended examples or as described, inter alia, in Spirin (1999), Invest. Opthalmol. Vis. Sci. 40, 3108–3115.

Furthermore, it is preferred that the obtained amplified cDNA is bound to a solid support, as defined hereinabove.

Since standard cacodylate containing buffers (like some cDNA synthesis buffers) may interfere with individual steps of the method of the invention (like the "tailing reaction") it is preferred that all or individual steps are carried out in a non-cacodylate buffer. Particularly preferred is a phosphate buffer and most preferred is a $KH_2PO_4$ buffer as employed in the appended examples. Preferably said buffer is a buffer of low ionic strength (see Nelson, Methods in Enzymology, 68, 41–50 (1979)). Furthermore, the use of dGTP or dCTP in "tailing" reactions leads to short extension of 15–30 nucleotides, while the use of dATP or dTTP leads to long extensions ranging from 70 to several hundred nucleotides (Nelson (1979), loc. cit.; MBI Fermentas 1998/1999 catalog, p. 125); Deng, Methods Enzymology, 100, 96–116, (1983)). Long poly(dA)/(dT) tails, however, result in non-homogeneous populations of cDNAs during amplification due to various hybridization/annealing sites. In contrast, the method of the invention with its short (10–30 bases) 5' primer and 3'tailing introduced oligo(dC) or oligo(dG) flanking regions generate homogenous populations of amplified cDNAs, amplifying preferentially the coding regions of the original cDNA molecules.

In yet a more preferred embodiment of the method of the present invention, the sample comprising mRNA/polyadenylated RNA to be amplified is derived from a cell and/or a tissue (or is a cell and/or a tissue), the genetic identity of which had been defined by comparative genomic hybridization (CGH). As shown in the appended examples, a method comprising CGH of a single cell (SCOMP; see Klein (1999), PNAS USA 96, 4494–4499)) has recently been described which allows for unambiguous identification of a single cell. With this method it is possible to identify, inter alia, a tumor cell and/or a cell of tumerous origin by its chromosomal aberrations. Employing the here described method for mRNA amplification and combining said method with SCOMP, it is therefore possible to isolate genomic DNA and mRNA from the same single cell.

The present invention also relates to a method for the preparation of an in vitro surrogate for (a) pathologically modified cell(s) or tissue(s) comprising the steps of:
(a) amplifying mRNA of said pathologically modified cell(s) or tissue(s) according to the steps of the method described herein above;
(b) assessing the quantity and, optionally, biophysical characteristics of the obtained cDNA and/or transcripts thereof, thereby determining the gene expression pattern of said pathologically modified cell(s) or tissue(s);
(c) selecting an in vitro cell, the gene expression pattern of which resembles the gene expression pattern of said pathologically modified cell(s) or tissue(s); and
(d) adapting the gene expression pattern of said in vitro cell to the gene expression pattern of the pathologically modified cell or tissue.

The term "in vitro surrogate" as used herein means (a) cell(s) or (a) cell line(s) which is capable of mimicking a pathological situation or a pathological condition. Said surrogate may be useful, inter alia, in medical, pharmacological or scientific experiments and may be employed for drug screening purposes. In particular, such a surrogate cell/cell line may be employed to identify potential drugs and/or medicaments. Such identification may be carried out by screening libraries of chemicals and/or biologics, and, preferably, said surrogate(s) is/are used in high throughput-screenings.

The assessment of the quantity and, optionally the biophysical characteristics of the obtained cDNA and/or transcripts thereof can be carried out by methods known to the person skilled in the art and/or as described herein.

The term "in vitro cell" as employed in accordance with this invention preferably relates to a cell which may be maintained in culture. Said cell is preferably maintained in culture for at least 1 hour, more preferably for at least 6 hours, more preferably for at least 12 hours, more preferably for at least one day, more preferably for at least two days, more preferably for at least 3 days, more preferably for at least one week, most preferably for several weeks.

It is particularly preferred that said surrogate/in vitro surrogate faithfully reflects the transcriptome/gene expression pattern of the pathologically-modified cell or tissue. Said surrogate should closely resemble the pathologically modified tissue or pathologically modified cell. It is therefore preferred that the "in vitro cell" as mentioned in step c. herein above is similar to the pathologically modified tissue/cell. For example, the "in vitro cell" may be derived from a similar tissue or organ as the pathologically modified/diseased tissue. Inter alia, coronary artery smooth muscle cells can be employed as "in vitro cells", the gene expression pattern of which resembles the gene expression pattern of restenotic tissue. Similar, liver cells (like, e.g, HepG2) may be employed to obtain a surrogate for pathologically modified liver tissue, cultured renal cells (like, e.g. ATCC 45505) for kidney diseased tissue, cardiomyoblasts (like, e.g., rat cardiomyocyte) for heart muscle diseased tissue, or NCI cell lines as described in Ross, Nat. Genetics 24 (2000), 227–235 for tumerous diseases, neoplastic diseases or cancer.

Said "adaption" of step (d) as mentioned herein above is carried out in order to adapt the gene expression pattern of the selected "in vitro cell" to a gene expression pattern which reflects more closely the gene expression pattern of the pathologically modified tissue/cell. In particular, when it was found (in steps (a) and (b) of the method as described herein above), that a particular transcript/expressed gene (or a group of particular transcripts/expressed genes) was down-regulated in comparison to said "in vitro cell" (or a control cell), it should be attempted to upregulate the expression said transcript/expressed gene (or group of said transcripts/expressed genes) in said "in vitro cell". Accordingly, should a specific transcript/expressed gene (or a group of specific transcripts/expressed genes) be upregulated in comparison to said "in vitro cell" (or a control cell), it should be attempted to downregulate said transcript/expressed gene (or a group thereof) in said "in vitro cell". Particular methods, factors, compounds and/or substances which may be useful to adapt the gene expression pattern of said in vitro cell are described herein below.

In one embodiment, it is preferred that said adaption step comprises contacting said in vitro cell with at least one compound, factor, substance, a plurality of compounds, factors, susbtances or a combination thereof and assessing whether said contacting leads to a modified gene expression pattern/transcriptome in said in vitro cell. The assessment of the gene expression pattern may be carried out by the method of the invention but may also comprise other analysis methods known in the art, like biochemical or biophysical methods. Particularly preferred are hereby methods like proteome analysis, comprising one- or two dimensional (gel) electrophoresis, high-performance liquid chromatography, mass spectrography or antibody-based detection methods (blotting or array systems).

The above mentioned pathologically modified cell(s) or tissue(s) an/or in vitro cell is preferably of animal origin. Particularly preferred are hereby cell(s) or tissue(s) derived and/or obtained from primates, rodents or artiodactyles. Even more preferred are cell(s) and/or tissue(s) from humans, monkeys, pigs, cows, rats or mice.

In yet another embodiment, the method for the preparation of an in vitro surrogate for
(a) pathologically modified cell(s) or tissue(s) comprises the further steps of
b(1). determining the gene expression pattern of (a) control cell(s) or (a) control tissue(s); and
b(2). determing the gene(s) which is/are differentially expressed in said for pathologically modified cell(s) or tissue(s) and said control cell(s) or tissue(s).

The here mentioned control cell(s) or control tissue(s) can be easily determined by the person skilled in the art. For example, similar tissue from a healthy donor may be employed. As shown, e.g., in the appended examples a control tissue for restenotic tissue may be media or media/intima of healthy coronary arteries. Furthermore, control cell(s) or control tissue(s) may be obtained during biopsis of hepatic tissue, renal tissue, prostate, cervical tissue etc.

It is particularly preferred that the gene expression pattern, i.e. the "transcriptome" of said control cell or control tissue is also determined by employing the method for the amplification of mRNA of a sample as described herein. Preferably, said transcriptome analysis of samples like the pathologically modified cell(s) or tissue(s), the control cell(s) or control tissue(s) comprises the steps of i. generating cDNA from polyadenylated RNA of said pathologically modified cell or tissue, said control cell or tissue and/or said in vitro cell employing at least one primer hybridizing to said polyadenylated RNA and comprising a 5' poly(C) or a 5' poly(G) flank;

ii.(aa) if present, removing non-hybridized, surplus primer(s) and/or surplus dNTPs;
   (ab) 3' tailing of said generated cDNA with a poly(G) tail when in step i. (a) primer(s) comprising a 5' poly(C) flank was/were employed or a poly(C) tail when in step i. (a) primer(s) comprising a 5' poly(G) flank was/were employed; or
   (b) 3' tailing of said generated cDNA with a poly(G) tail when in step i. (a) primer(s) comprising a 5' poly(C) flank was/were employed or a poly(C) tail when in step i. (a) primer(s) comprising a 5' poly(G) flank was/were employed using an RNA-ligase, irrespective of the presence or absence of surplus primer(s) and/or surplus dNTPs;

iii. amplifying the tailed cDNA with a primer hybridizing to the tail(s) generated in step ii(ab) or ii(b);

iv. employing the amplified cDNA in (a) hybridization assays; and v. detecting differences and/or similarities in the gene expression pattern of said pathologically modified cell or tissue, said control cell or tissue and/or said in vitro cell The embodiments as described herein above for the method of the invention may be applied for said transcriptome analysis of said pathologically modified cell(s) or tissue(s), control cell(s) or control tissue(s) and/or said in vitro cell.

The above described method for the preparation of an in vitro surrogate can be, inter alia employed for restenotic tissue or for an restenotic cell. Said control cell or said control tissue(s) may be selected from the group consisting of smooth muscle cells, media/intima of (healthy) coronary arteries and media/intima of (healthy) peripheral arteries.

The "in vitro cell" to be accepted to the gene expression pattern of a pathologically modified cell(s) or tissue(s) may be derived from primary cell culture, a secondary cell culture, a tissue culture or a cell line. Preferably, these cells and/or cell cultures are, but are not limited to, cultured muscle cells, cultured smooth muscle cells, cultured coronary artery smooth muscle cells, HepG2 cells, Jurkat cells, THP-1 cells, Monomac-6 cells or U937-cells. Such cells are easily obtainable from sources known in the art, like DSMZ, Braunschweig or the ATCC, USA. Furthermore, cardiomyoblasts may be employed as "in vitro cell" for adaption to a "surrogate".

Said adaption step (step d. of the above described method for the preparation of an in vitro surrogate) may comprise the exposure of said in vitro cell to physical and/or chemical change(s), wherein said physical change(s) may comprise temperature shifts, light changes, pressure, pH-changes, changes in ionic strength or changes in the composition of gas phase(s) (like $O_2$, $N_2$, CO, $CO_2$) and said chemical changes may comprise medium exchanges, medium substitutions, medium depletions and/or medium additions. It is particularly preferred that said chemical changes comprise the exposure to compounds like growth factors, hormones, vitamines, antibodies or fragments and/or derivatives thereof, small molecule ligands, cytokines, transcription factors, kinases, antibiotics, natural and/or non-natural receptor ligands, or components of signal transduction pathways. Said adaptation step may also comprise co-culturing with other cells/cell lines, for example co-culturing with blood cells, glial cells, dendritic cells or osteoclasts. Said blood cell may comprise monocytes and T-lymphocytes.

In an even more preferred embodiment of the method for the preparation of an in vitro surrogate, said cytokine is IFN-γ (or a functional derivative therof), said natural and/or non-natural receptor ligand is a ligand for IFN-γ receptor (a and/or b chain), said transcription factor is IRF-1 or ISGF3-γ-(p48), said kinase is tyrosine kinase Pyk2, said components of signal transduction pathways is Dap-1, BAG-1, Pim-1 or IFN-γ-inducible protein 9–27, said growth factor is platelet growth factor AA, angiotensin or fibroblast growth factor or said antibiotic is rapamycin.

In this context, the term "functional derivative" of IFN-γ relates to derivatives that retain or essentially retain the biological properties of natural IFN-γ. Examples of such derivatives are muteins. The same applies, mutatis mutandis, for other components mentioned herein.

In vitro surrogate(s) as obtained by the above described methods are particulary useful in drug screening methods and/or in toxicological analysis. Such methods comprise, but are not limited to the detection of modified gene expression pattern after contacting said in vitro surrogate with a test substance and/or a potential drug candidate. Such screening methods are well known in the art and are, inter alia, described in Scherf, Nat. Genetics 24 (2000), 236–244; Ross, Nat. Genetics 24 (2000), 227–235. High-throughput screenings are described and/or reviewed in Sundberg, Curr. Opin. Biotechnol. 11 (2000), 47–53; Hopfinger, Curr. Opin. Biotechnol. 11 (2000), 97–103; Vidal, Trends Biotechnol. 17 (1999), 374–381; Gonzales, Curr. Opin. Biotechnol. 9 (1989), 624–631; Fernandes, Curr. Opin. Chem. Biol. 2 (1998), 597–603.

Additionally, the present invention relates to a method for identifying differentially expressed genes in a test sample, wherein said method comprises the steps of (a) providing a test sample and a control sample each comprising polyadenylated RNA; (b) employing the steps of the method for the amplification of mRNA of the present invention on said test and control sample; and (c) comparing the obtained amplified cDNA of said test sample with the obtained amplified cDNA of said control sample. The test and control sample may be derived from the same organism but may also be derived from different organisms/individuals. Furthermore, said test sample may comprise tissue cultures or cell cultures. Furthermore, said test and/or control sample comprises preferably the same kind of cell(s) and/or tissue(s). The comparison of step (c) can be carried out as, for example, shown in the appended examples and may involve hybridization of obtained amplified cDNA to cDNA arrays. The method for identifying differentially expressed genes may therefore comprise the comparison of tissue, (a low number of) cells or a single cell of distinct origin. For example, pathological and non-pathological tissue, (low number of) cells or single cells may be compared on the transcriptome level.

The present invention also relates to a method for identifying a drug candidate for prevention or therapy of a pathological condition or a pathological disorder comprising the steps of (a) contacting a sample comprising polyadenylated RNA with said drug candidate; (b) employing the steps of the method for the amplification of mRNA of the present invention on said sample; and (c) detecting the presence, the absence, the increase or the decrease of particular expressed genes in said sample.

The sample to be contacted with said drug candidate may be an isolated organ, tissue, (low number of) cells or a single cell. Said sample may also be a tissue or a cell culture sample. Furthermore, it is also envisaged that a laboratory animal and/or a subject may be contacted with said drug candidate and that after (or during) said contact a corresponding sample is obtained, for example, by biopsy.

Furthermore, the present invention provides for a method for in vitro detection of a pathological condition or a susceptibility to a pathological condition in a subject comprising the steps of (a) providing a sample comprising polyadenylated RNA from said subject; (b) employing the method for the amplification of mRNA of the present invention on said sample; and (c) detecting a pathological condition or a susceptibility to a pathological condition based on the presence, the absence, the increase, the decrease or the amount of (a) expressed gene(s) in said sample.

The presence, absence, increase or decrease or amount can be detected, inter alia, by comparing the obtained cDNA(s) with obtained cDNA(s) from a healthy control sample. The sample(s) may be of human origin.

In addition, the present invention relates to the use of the amplified cDNA as obtained by the method of the invention for in vitro and/or in vivo expression. Methods for in vitro and/or in vivo expression are well known in the art and are described, inter alia, ("Current Protocols in Molecular Biology", edited by Ausubel et al., John Wiley & Sons, USA (1988); Schoelke, Nature Biotech., 18, 233–234 (2000)) or in "Biotechnology"; edited by Rehn and Reed, VCM Verlagsgesellschaft mbH, Weinheim, FRG, (1993). Furthermore, in vitro expression in plant cells is described in Weissbach "Methods for Plant Molecular Biology", Academic Press, San Diego, U.S.A. (1988). Particular preferred systems for in vitro expression are translation systems known in the art, like E. coli lysates for coupled transcription/translation (Basset, J. Bacteriol.,(1983) 156, 1359–1362), wheat germ translations systems or reticulocyte lysates (Walter, Methods Enzymol., 93, 682–691 (1983); Dasnahapatra, Methods Enzymol., 217, 143–151 (1993); Hancock, Methods Enzymol, 255, 60–65 (1995); Wilson, Methods Enzymol., 250, 79–91 (1995)). Said in vitro and/or in vivo expression of said amplified cDNA comprises transcription as well as translation events and, therefore, comprises the generation of mRNA as well as, if desired, of protein(s) and/or peptide(s). Therefore, the present invention also relates to the use of amplified cDNA as obtained by the method of the present invention for the in vitro and/or in vivo preparation of mRNA transcripts.

The present invention also relates to the use of the amplified cDNA as obtained by the method of the present invention or of mRNA transcripts as defined hereinabove and obtained by in vitro and/or in vivo expression of the cDNA as obtained by the method of the present invention, in hybridization assays, and/or in interaction assays.

Preferably, said hybridizing assays are carried out under defined conditions. Most preferably, said hybridizing conditions are stringent conditions. However, the term "hybridizing" as used in accordance with the present invention relates to stringent or non-stringent hybridization conditions. Said hybridization conditions may be established according to conventional protocols described, for example, in Sambrook, "Molecular Cloning, A Laboratory Manual", Cold Spring Harbor Laboratory (1989) N.Y., Ausubel, "Current Protocols in Molecular Biology", Green Publishing Associates and Wiley Interscience, N.Y. (1989), or Higgins and Hames (eds) "Nucleic acid hybridization, a practical approach" IRL Press Oxford, Washington D.C., (1985).

In a preferred embodiment, said hybridization assay comprises the hybridization to oligonucleotide arrays, cDNA arrays, and/or PNA arrays, said interaction assay comprises the interaction with carbohydrate(s), lectin(s), ribozyme(s), protein(s), peptide(s), antibody(ies) or (a) fragment(s) thereof, and/or aptamer(s).

The above mentioned arrays are well known in the art (see, inter alia, Debouck, Nat. Genet. 21:48–50 (1999); Hacia, Nat. Genet., 21, 42–7 (1999); Cole, Nat. Genet. 21, 38–41 (1999); Bowtell D D., Nat. Genet., 21, 25–32 (1999); Cheung, Nat. Genet., 21, 15–19 (1999); Duggan, Nat. Genet., 21, 10–14 (1999); Southern, Nat. Genet., 21, 5–9 (1999)). In particular, cDNA arrays may be obtained from Clontech, Palo Alto; Research Genetics, Huntsville and comprise cDNA microarrays, and oligonucleotide arrays may be obtained from Affymetrix, Santa Clara. cDNA arrays may be prepared, inter alia, according to the methods described in DeRisi, Nat. Genet. (1996), 14, 457–460; Lashkari, Proc. Natl. Acad. Sci. USA, 94, 13057–13062 (1997); Winzeler, Methods Enzymol. 306, 3–18 (1999); or Schena (1995), loc. cit., oligonucleotide arrays, inter alia, according to Southern (1999), loc. cit.; Chee, Science, 274, 610–614 (1996). The above mentioned arrays may comprise macroarrays as well as microarrays.

As shown in the appended examples, the cDNA as obtained by the method of the present invention (or mRNA transcripts of said cDNA) can be employed on cDNA arrays/cDNA microarrays in order to deduce the gene expression pattern/transcriptome of a (test) sample comprising polyadenylated RNA.

Hybridization assays as described herein above are useful, inter alia, in medical, diagnostic, pharmacological as well as in scientific settings. As shown in the appended examples, it is possible to employ DNA as obtained by the method of the present invention in order to deduce the (gene) expression pattern of pathologically modified cells and/or tissues, e.g., tumerous (cells) tissues, restenotic tissue.

The appended examples document, inter alia, that the method of the present invention can be employed to deduce differentially expressed genes in restenotic tissue. In this way 224 genes were identified that are differentially expressed in restenosis, wherein 167 genes were overexpressed and 56 genes were underexpressed in comparison to controls. The detection of specific, differentially expressed genes or gene expression pattern(s) can, therefore, also be employed in diagnostic methods in order to define, inter alia, restenotic tissue. Furthermore, as described in the appended examples, the method of the present invention may be useful in the diagnosis of neoplastic diseases, cancer.

The amplified cDNA as obtained by the method of the present invention is, therefore, particularly useful in establishing gene expression profiles of tissues and/or cells. Such gene expression profiles/gene expression patterns may be particularly useful and important in drug discovery screens. It is particularly preferred that data obtained by such gene expression profiling be used in combination with drug activity patterns (see, inter alia, Weinstein, Science 275 (1997), 343–349; Weinstein, Science 258 (1992), 447–451, van Osdol, J. Natl. Cancer Inst. 86 (1994), 1853–1859 or Pauli, J. Natl. Cancer Inst. 81 (1989), 1088–1092). Furthermore, it is envisaged that cDNA as obtained by the method of the present invention and/or mRNA transcripts thereof be used in assays wherein gene expression patterns and drug activity profiles are correlated as described in Scherf, Nat. Genetics 24 (2000), 236–244 and in Ross, Nat. Genetics 24 (2000), 227–235. Further, the "transcriptome"-data obtained by the methods of the invention, as described herein above, may also be correlated on the protein level, as demonstrated in the appended examples.

The present invention also relates to the use of amplified cDNA obtained by the method of the invention for sequence specific PCR, cDNA cloning, substructive hybridization cloning, and/or expression cloning. Specific PCR can be used, e.g., to determine the relative amounts of transcripts within a given sample and between samples. The cDNA generated by the present invention could also be applied to subtractive hybridization cloning to select for cDNAs specific for or absent from the sample which is demonstrated in the appended examples (Rothstein, Methods Enzymol. 225, 587–610 (1993); Diatchenko, Methods Enzymol., 303, 349–380 (1999)).

In a preferred embodiment, the adapter-primers Eco 44 I: 5'-GTA ATA CGA CTC ACT ATA GGG CTC GAG CGG CTC GCC CGG GCA GG-3' (SEQ ID NO: 31), Eco 12 I:5'-AAT TCC TGC CCG-3' (SEQ ID NO: 32), Eco 43 II: 5'-TGT AGC GTG AAG ACG ACA GAA AGG TCG CGT GGT GCG GAG GGC G-3' (SEQ ID NO: 33) or Eco 12 II: 5'-AAT TCG CCC TCC-3' (SEQ ID NO: 34) may be employed with the above mentioned method i.e. substructive hybridization analysis. In a further preferred embodiment, the primers P1–30: 5'-GTA ATA CGA CTC ACT ATA GGG CTC GAG CGG-3' (SEQ ID NO: 35), P2–30: 5'-TGT AGC GTG AAG ACG ACA GAA AGG TCG CGT-3' (SEQ ID NO: 36), P1–33: 5'-GTA ATA CGA CTC ACT ATA GGG CTC GAG CGG CTC-3' (SEQ ID NO: 37), P2–33: 5'-TGT AGC GTG AAG ACG ACA GAA AGG TCG CGT GGT-3' (SEQ ID NO: 38), PN1–30: 5'-CGA CTC ACT ATA GGG CTC GAG CGG CTC GCC-3' (SEQ ID NO: 39) or PN2–30: 5'-GTG AAG ACG ACA GAA AGG TCG CGT GGT GCG-3' (SEQ ID NO: 40) may be employed when amplifying the resulting cDNA populations which may be obtained by the above mentioned substructive hybridization analysis.

In a more preferred embodiment primers primers P1–30: 5'-GTA ATA CGA CTC ACT ATA GGG CTC GAG CGG-3' (SEQ ID NO: 35), P2–30: 5'-TGT AGC GTG AAG ACG ACA GAA AGG TCG CGT-3' (SEQ ID NO: 36) are employed for the aforementioned method as shown in the appended examples.

The present invention also provides for a kit comprising at least one primer as defined herein above.

Advantageously, the kit if the present invention further comprises, besides said primer/primers, optionally, solid supports (such as magnetic beads), enzymes, such as reverse transcriptase(s), RNA-ligase or terminal deoxynucleotidyl-transferase as well as (a) reaction buffer(s) (like cDNA "wash buffer" or "tailing buffer") and/or storage solution(s). Furthermore, parts of the kit of the invention can be packaged individually in vials or in combination in containers or multicontainer units. The kit of the present invention may be advantageously used for carrying out the method(s) of the invention and could be, inter alia, employed in a variety of applications referred to above, e.g., in diagnostic kits or as research tools. Additionally, the kit of the invention may contain means for detection suitable for scientific and/or diagnostic purposes. The manufacture of the kits follows preferably standard procedures which are known to the person skilled in the art.

BRIEF DESCRIPTION OF THE DRAWINGS

The Figures show.

FIG. 7: Immunohistochemical stains of neointima from human coronary artery in-stent restenosis for v. Giesson (left panel) and smooth muscle alpha-actin (right panel). The shown experiment is a representative of 3 independent specimen. Bars indicate 100 µm.

FIG. 9: cDNA array analysis. The same array is shown with three independent hybridization experiments comparing mRNA isolated from neointima (panel A) or from control vessel (panel B), and in the absence of a biological sample (panel C). The cDNA array contained 588 genes including nine housekeeping genes and three negative controls [M13 mp 18 (+) strand DNA; lambda DNA; pUC18 DNA]. The experiment shown here is a representative of hybridization experiments with 10 neointima and 10 control specimen. Circles indicate four hybridization signals (A-D) differentially expressed between restenosis and control.

FIG. 14: Cluster image showing the different classes of gene expression profiles of the two hundred twenty four genes whose mRNA levels were different between neointima and control. This subset of genes was clustered into four groups on the basis of their expression in different cell types. The expression pattern of each gene in this set is displayed here as a horizontal strip. Each column represents the average mRNA expression level of the examined group. For each gene, the average of the mRNA level of neointima (n=10), of control (n=11), of proliferating CASMCs (n=2) and of blood samples (n=10) normalized to the mRNA expression level of the housekeeping genes is represented by a color, according to the color scale at the bottom. Group I contained genes only expressed in neointima specimen (FIG. 14A). Group II contained genes expressed simultaneously in neointima and proliferating CASMCs (FIG. 14B). Group III consisted of genes, whose mRNA were expressed in neointima as well as in blood (FIG. 14C).

Group IV contained genes, whose mRNA was overexpressed in control specimen (FIG. 14D).

Figure 15:
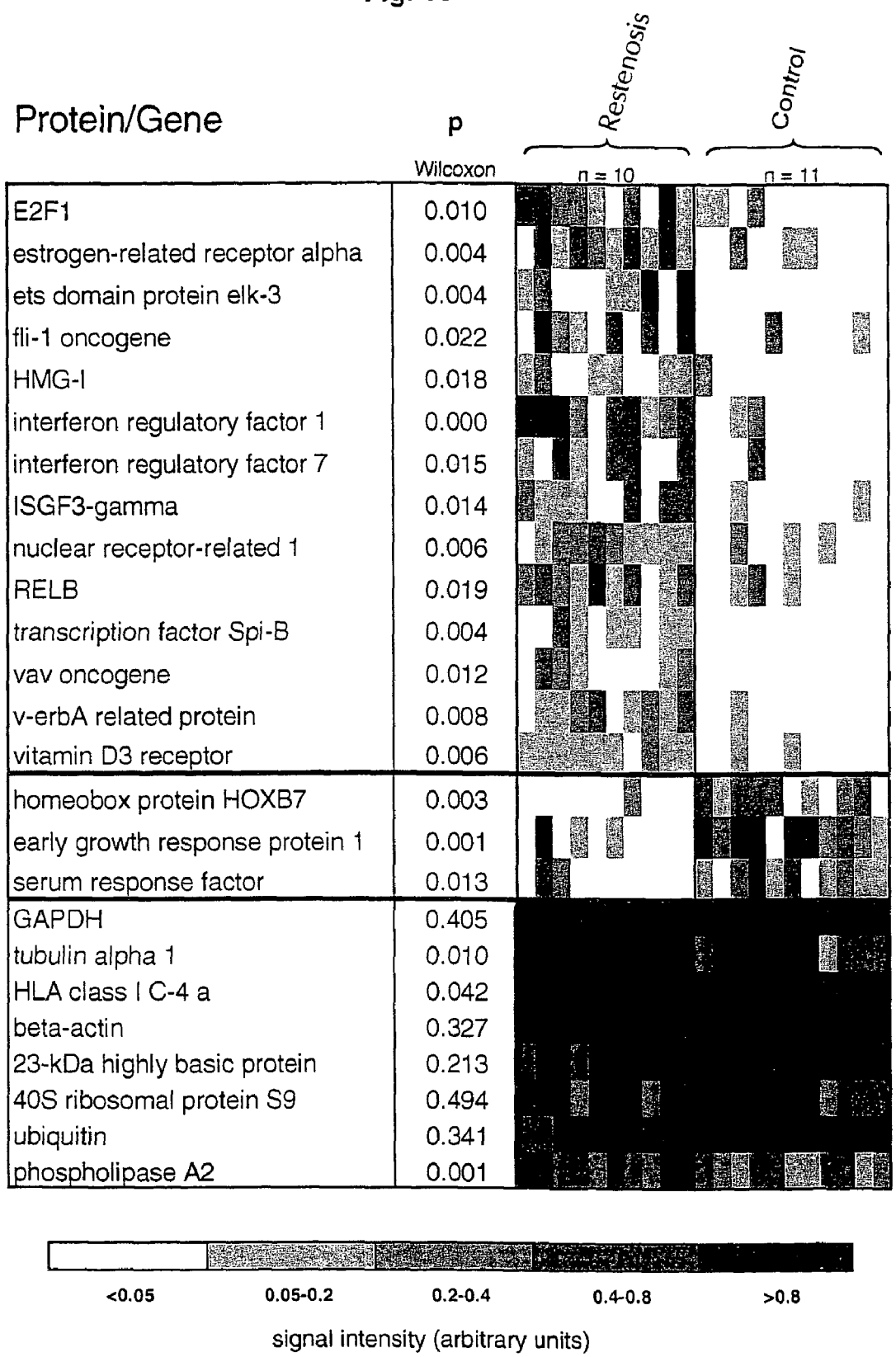

FIG. 15: Expanded view of the transcription factorcluster containing 14 genes that were upregulated in neointima versus control and three transcription factors that were downregulated in neointima. In this case, each column represents a single specimen, and each row represents a single gene FIG. 16: Expanded view of the IFN-γ-associated cluster containing 32 genes that were upregulated in neointima versus control. In this case, each column represents a single specimen, and each row represents a single gene.

FIG. 17 Immunohistochemical stains of neointima from a carotid restenosis and healthy control media for the IRF-1 protein (left panel: control media; right panel: neointima). The experiment shown is a representative of 6 independent experiments.

Figure 18:
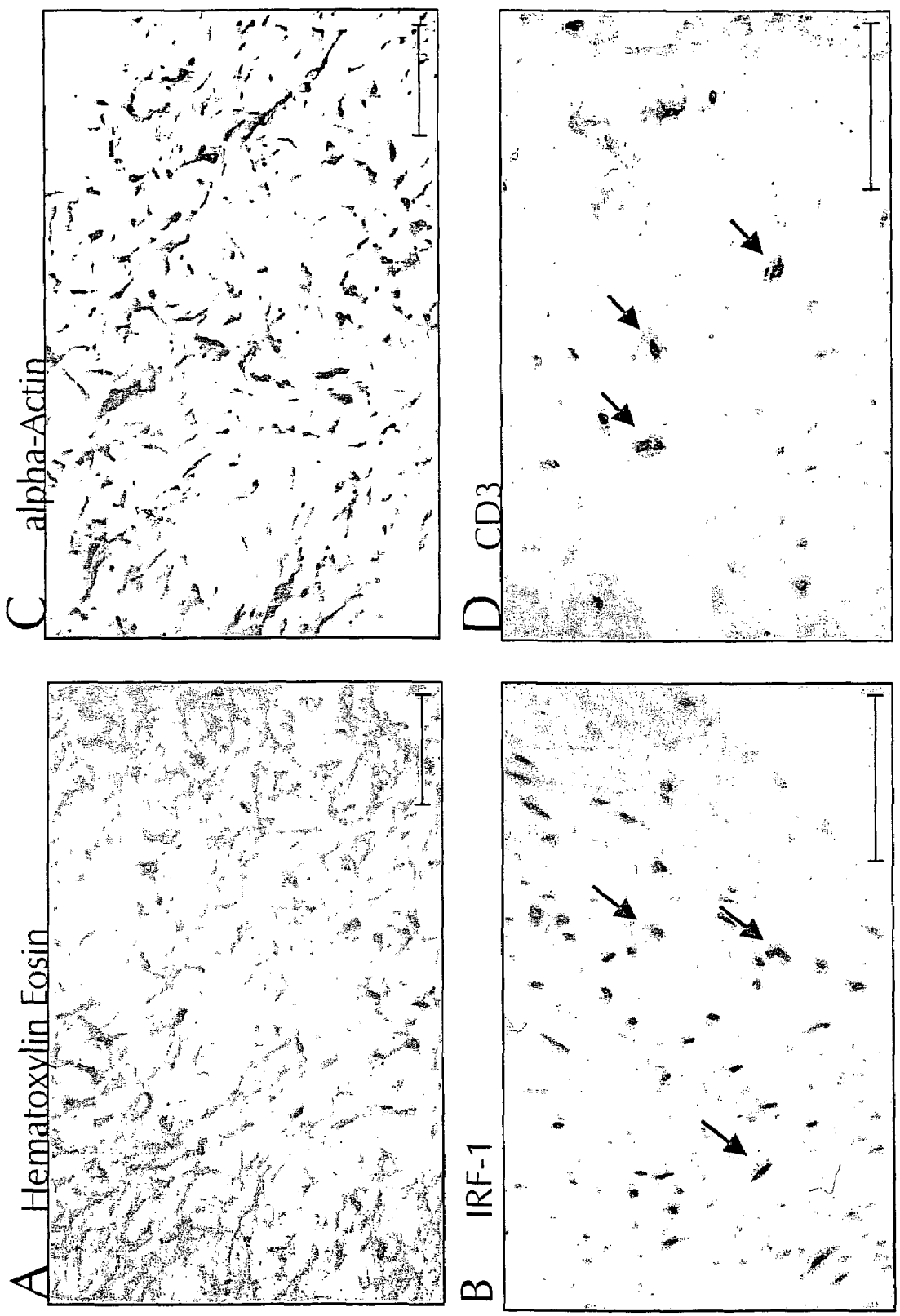

FIG. 18: Immunohistochemical stain of neointima from a coronary in-stent for the IRF-1 protein. Panel A shows a hematoxylin eosin staining of the neointimal specimen from in-stent restenosis, panel B shows a staining for the smooth muscle cell marker α-actin, panel C shows the immunohistochemical stain for the transcription factor IRF-1 in neointima from in-stent restenosis and panel D shows immunohistochemical stain for CD3. The experiment shown here is a representative of three independent experiments.

Figure 19:
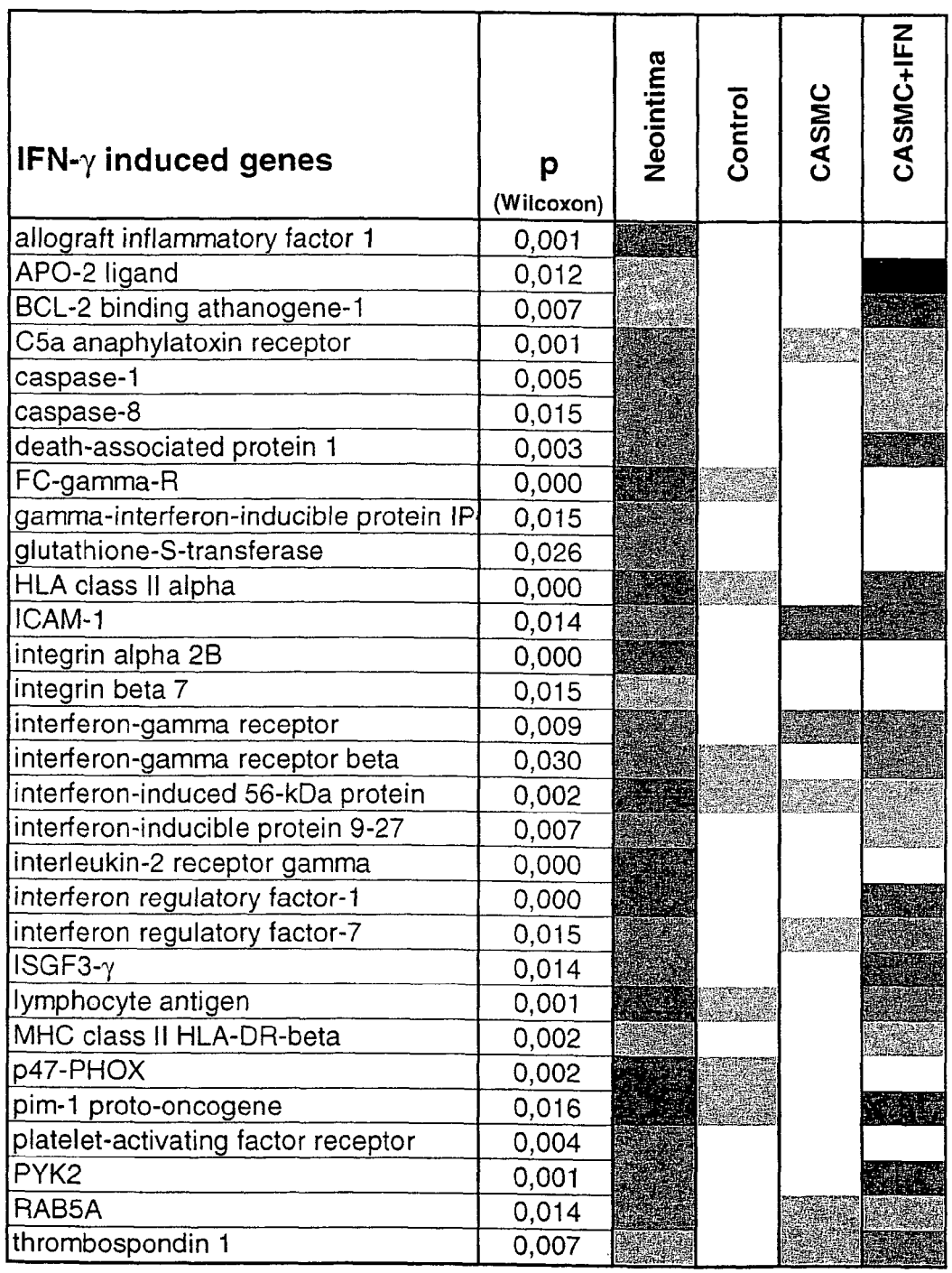

FIG. 19: View of the IFN-γ-associated cluster containing the 32 genes that were upregulated in neointima versus control compared to expression in cultured CASMCs and to cultured CASMCs stimulated for 16 h with 1000 U/mL IFN-γ. In this case, each column represents a single specimen, and each row represents a single gene. One grey value corresponds to a signal intensity as shown at the bottom of the figure.

Figure 20:
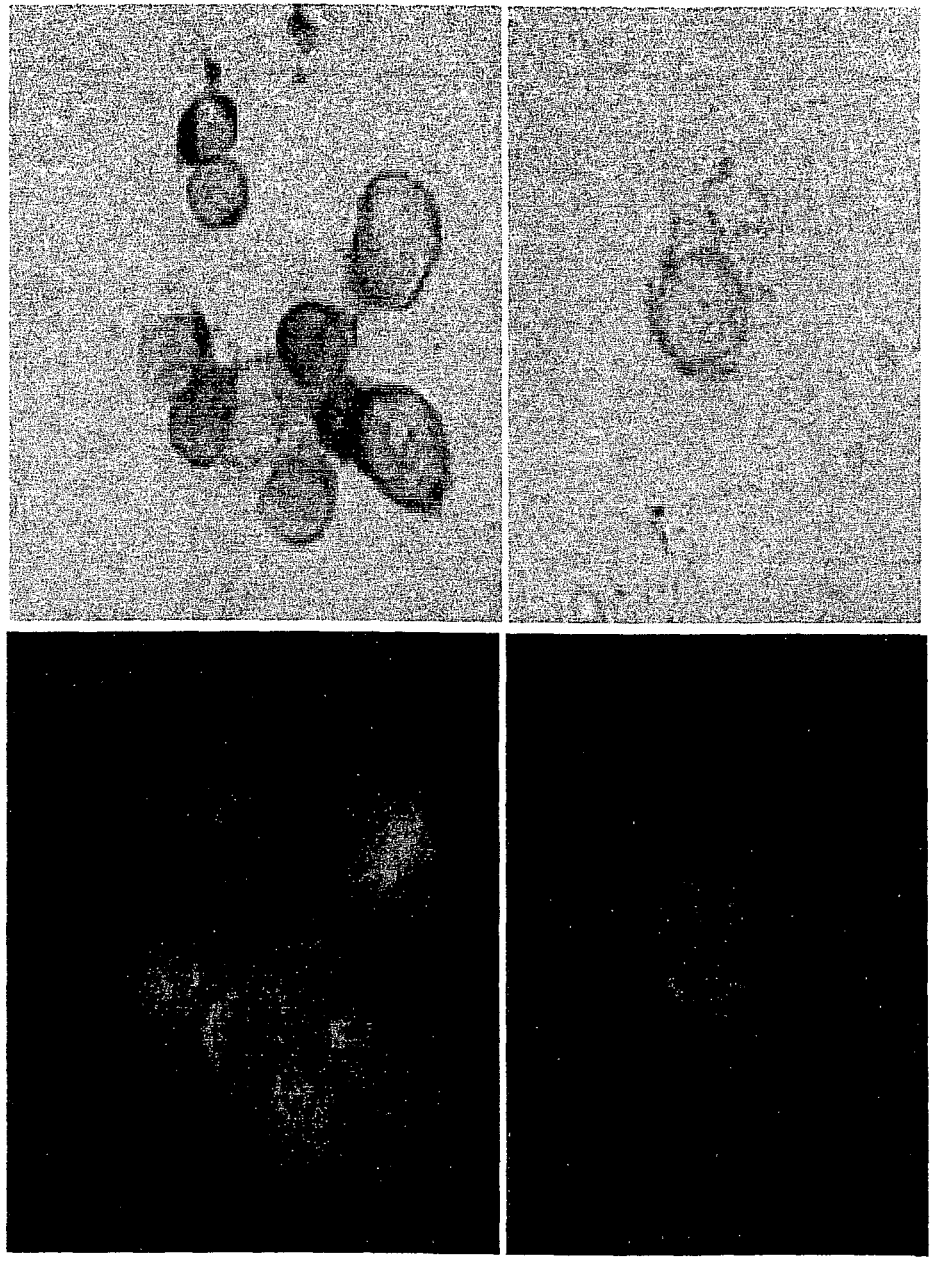

FIG. 20: Double staining of disseminated tumor cells in bone marrow. Cells in small aggregates (of seven and of two cells) in the upper panel and one single cell detected in bone marrow of two different patients were stained for cytokeratin (red fluorescence) and Emmprin (blue).

Figure 21:
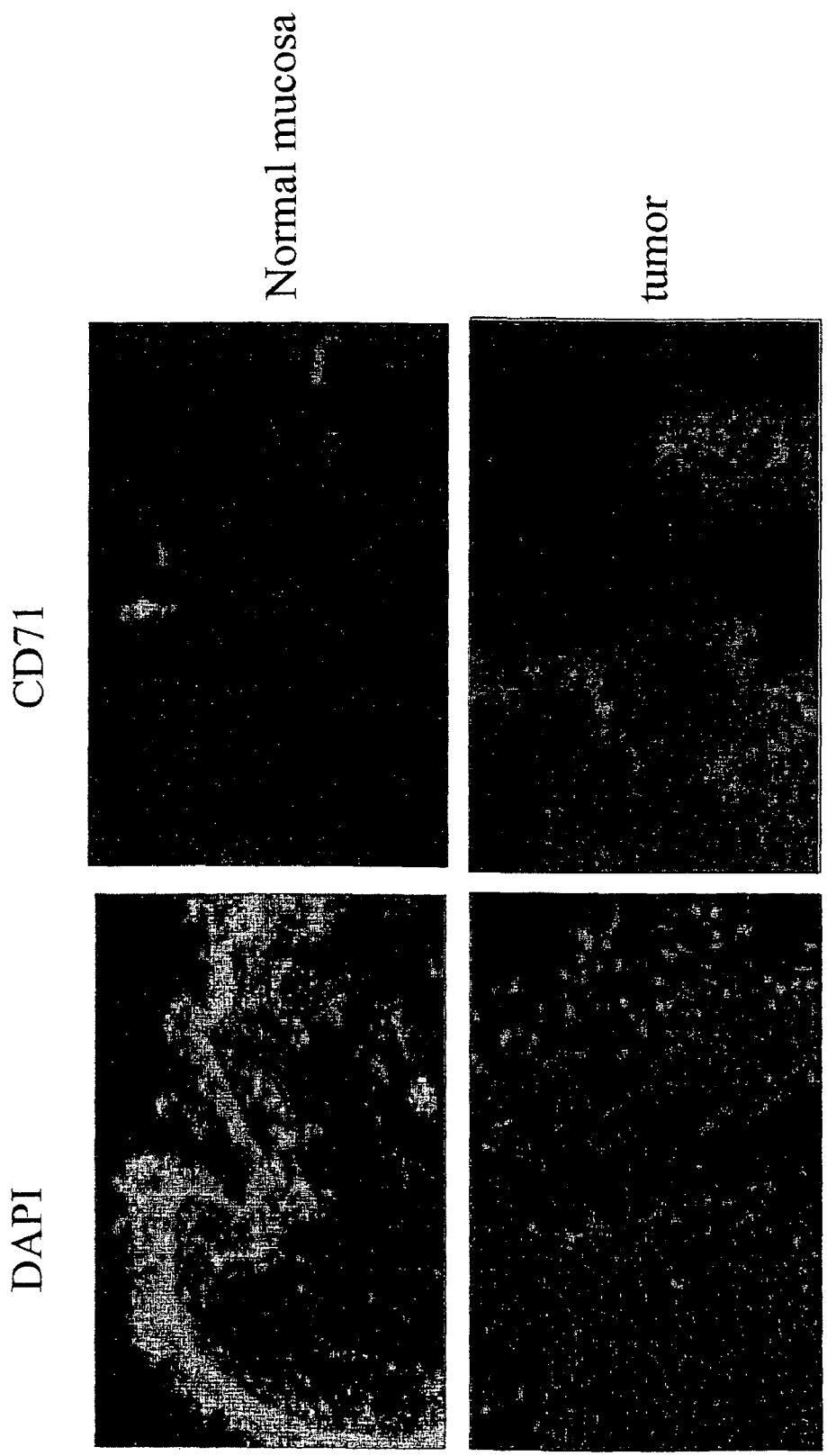

FIG. 21: Differential expression of the transferrin receptor (CD71) on tumor cells. DAPI staining of cellular nuclei (left panel), upregulated CD71 expression is found in tumor tissue (right panel).

Figure 22:
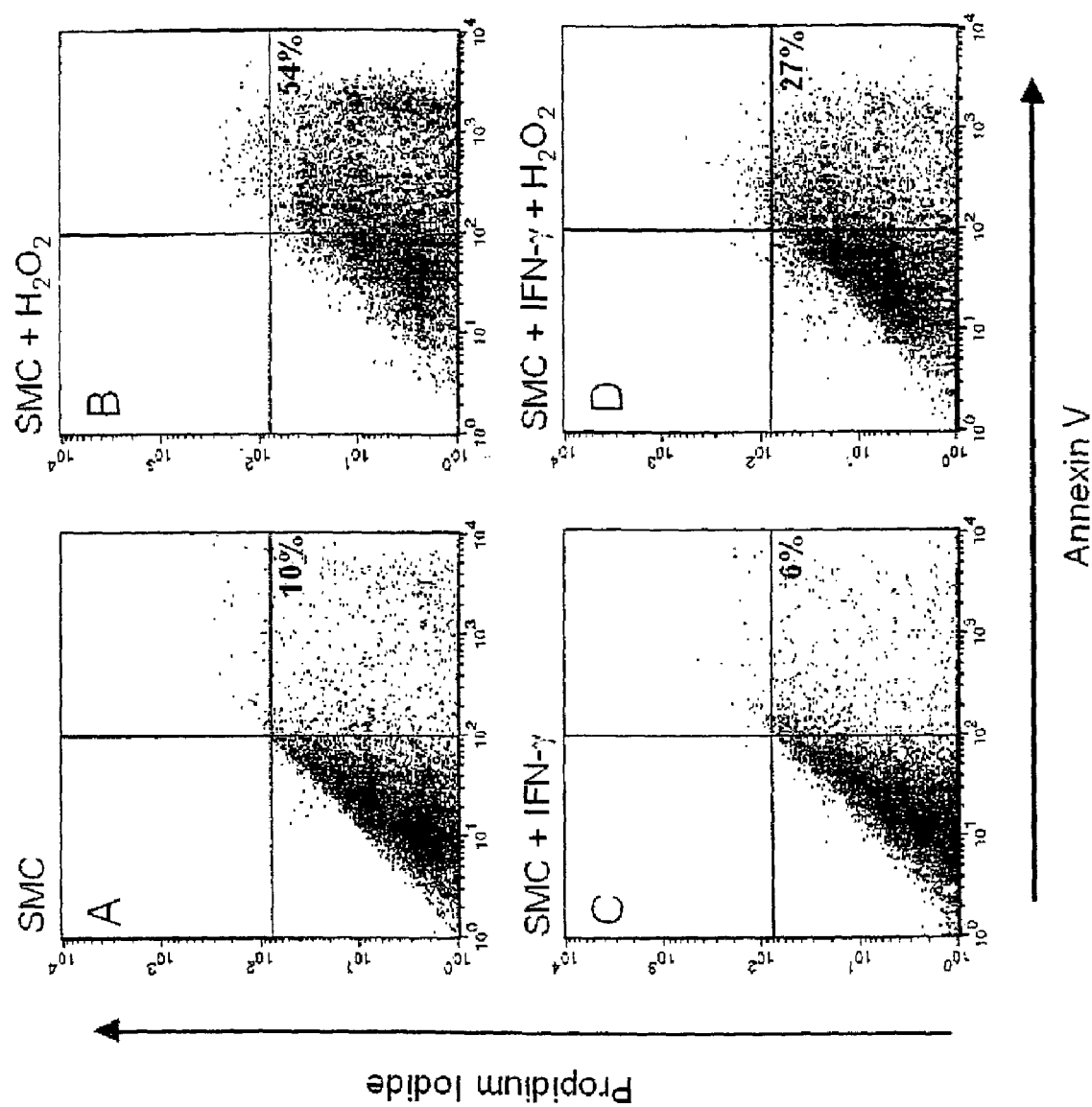

FIG. 22: Effect of IFNγ on survival of cultured SMCs. Flow cytometry analysis of spontaneous (panel A and C) and $H_2O_2$-induced apoptosis (panel B and D). Cells were double-stained by FITC-labelled Annexin V and Pi at 6 h after treatment with 100 μmol/l $H_2O_2$. A representative analysis of 5 independent experiments is shown.

Figure 23:
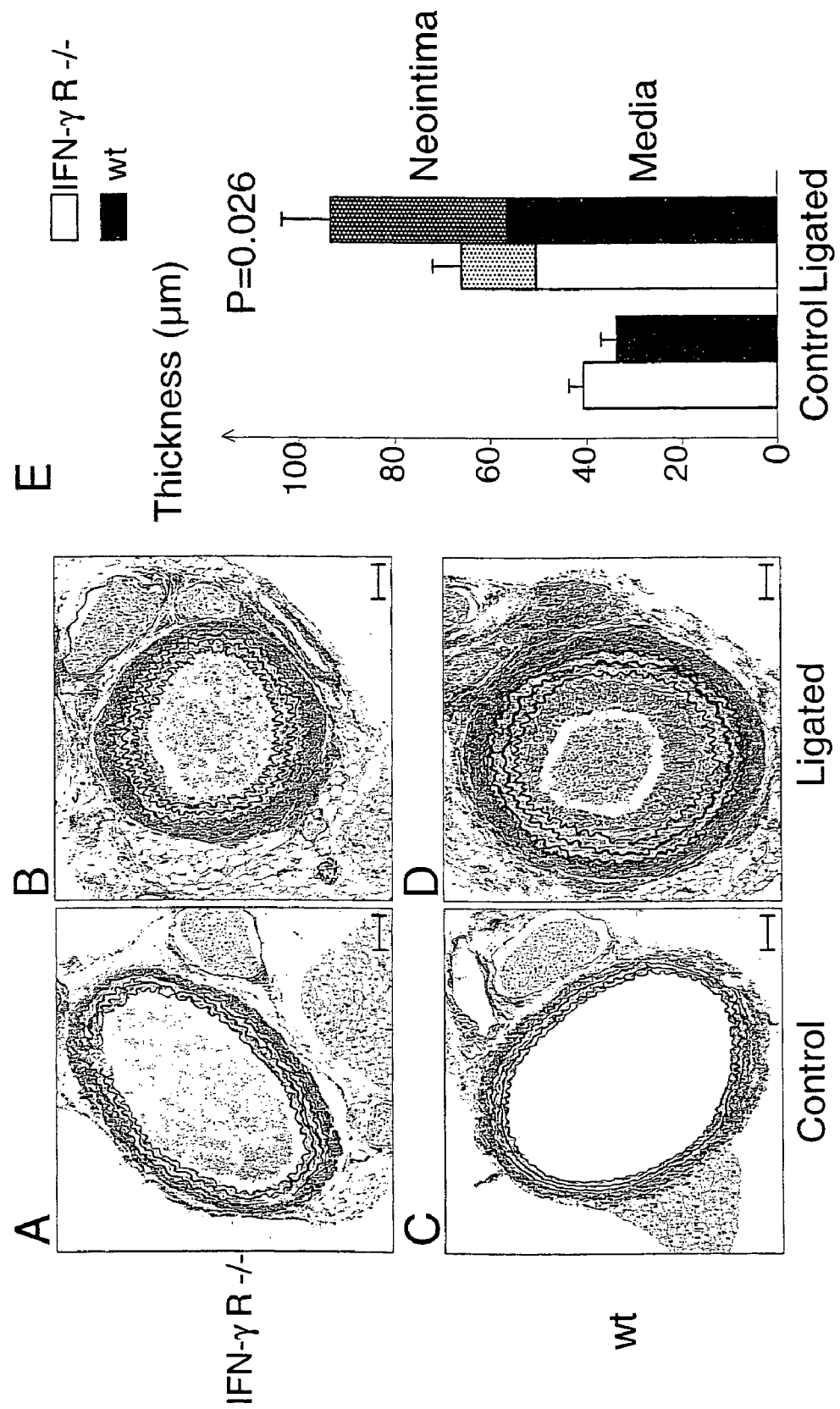

FIG. 23. The effect of an IFNγ receptor null mutation on the development of neointima in a mouse model of restenosis. (A–D) Representative microphotographs of cross-sectioned mouse carotid arteries from wildtype (wt) and IFN-γR$^{-/-}$ knockout (ko) mice are shown for the untreated artery (control) and the contralateral ligated artery (ligated) at 4 weeks after ligation. The van-Giesson staining procedure was used. The bars represent a lenght of 100 μm. (E) Data from 16 wildtype and 11 FN-γR$^{-/-}$ mice are shown as mean±SEM (bars) and analyzed by the t-test for unpaired samples. The scale gives the thickness of media and neointima in μm. Open columns: control animals before and after carotis ligation; filled columns: knockout animals before and after carotis ligation. The shaded area indicates the thickness of neointima.

Figure 24:
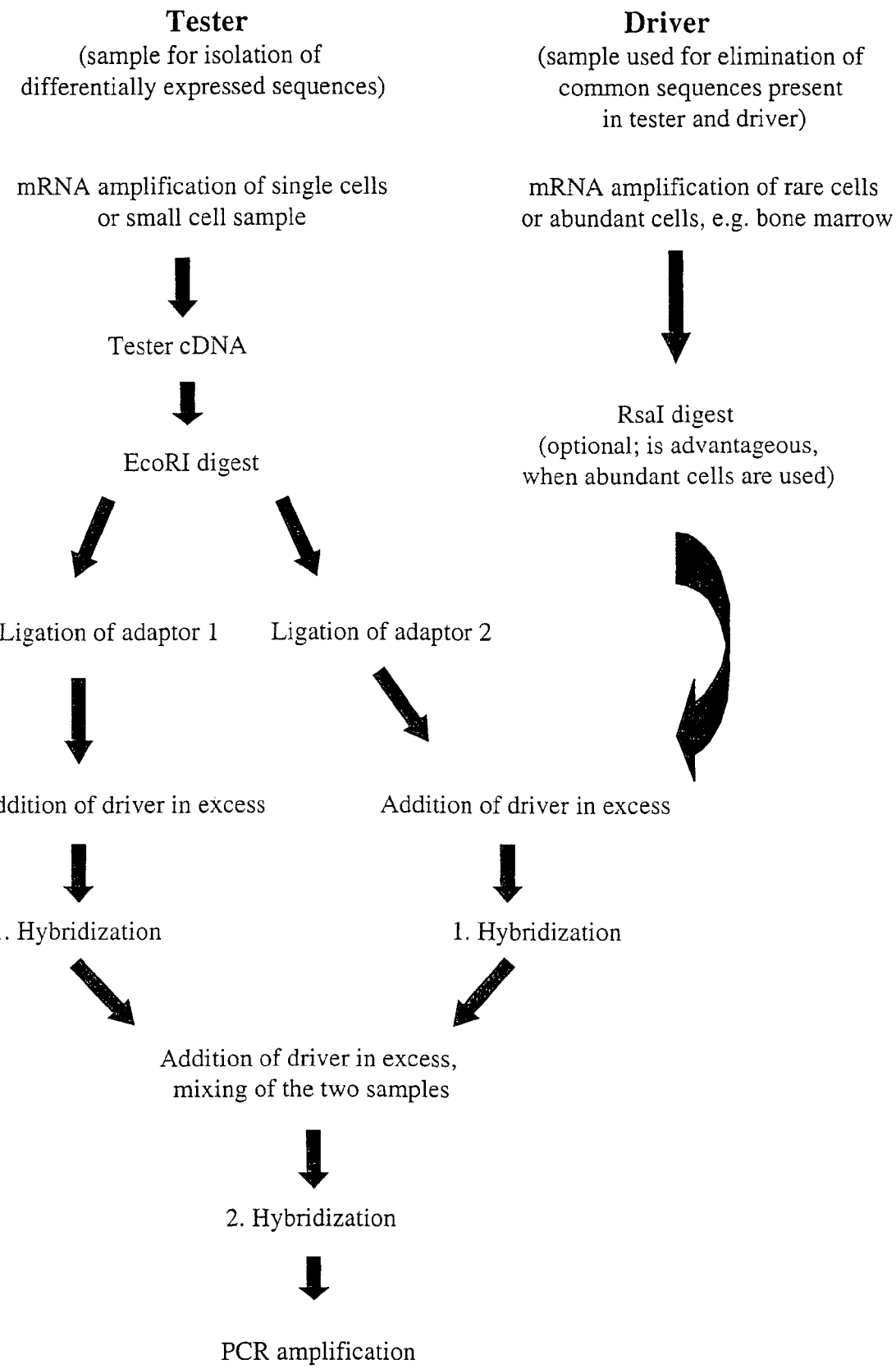

FIG. 24: Flow chart of SSH analysis performed with single cells or small cell samples.

FIG. 25: Screening of colonies by southern blot using labeled driver and tester as probes. Lane 1–9 colonies obtained after subtraction. Colony #4 was identified as ESE1, an epithelium-specific transcription factor. M=molecular weight marker.

Figure 26:
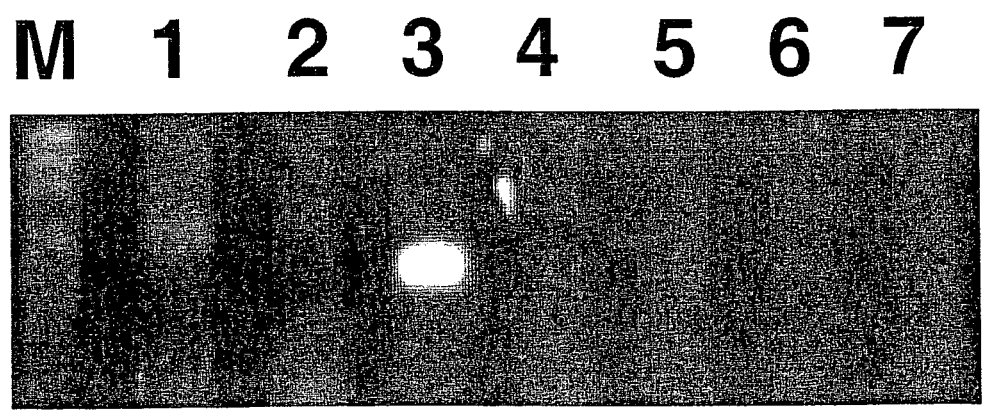

FIG. 26: Differential expression of ESE1 in tumor cells analyzed by PCR and gelectrophoresis. Lane 1–4 single breast cancer cells, 5–7 bone marrow of healthy donors. M=molecular weight marker.

DETAILED DESCRIPTION OF THE INVENTION

The invention will now be described by reference to the following biological examples which are merely illustrative and are not to be construed as a limitation of scope of the present invention.

EXAMPLE I

Generation and Global Amplification of Single Cell cDNA

The amount of mRNA from single cells is too low for direct use in array-based transcriptome analysis. Total RNA from 50,000 cells (10 μg) was reported to be the detection limit for direct-labelling approaches (Mahadevappa, Nat. Biotechnol., 17, 1134–1136 (1999)). Using a linear amplification step, this number could be reduced to 1000 cells (Luo, Nat. Med., 5, 117–122 (1999)), which is still far beyond applicability for the study of micrometastatic cells. Thus reverse transcription of mRNA and amplification of the cDNA is necessary. Key is the development of an unbiased global amplification procedure. In a simplified manner, this approach consists of four basic steps: (1) isolation of the mRNA on oligo-dT-coated solid support, (2) cDNA synthesis using random primers containing a 5'-oligo-dC (or dG) flanking region, (3) 3'tailing reaction with dGTP (or dCTP) generating a 3'-oligo-dG flanking region, followed by (4) single primer-based amplification using a primer hybridizing to oligo-dG (or -dC) flanking regions of the cDNA molecules. In order to fulfil these four basic steps and to obtain high sensitivity and reliability for cDNA synthesis, 3'-tailing and pCR amplification, tRNA and rRNA had to be removed.

Figure 1:
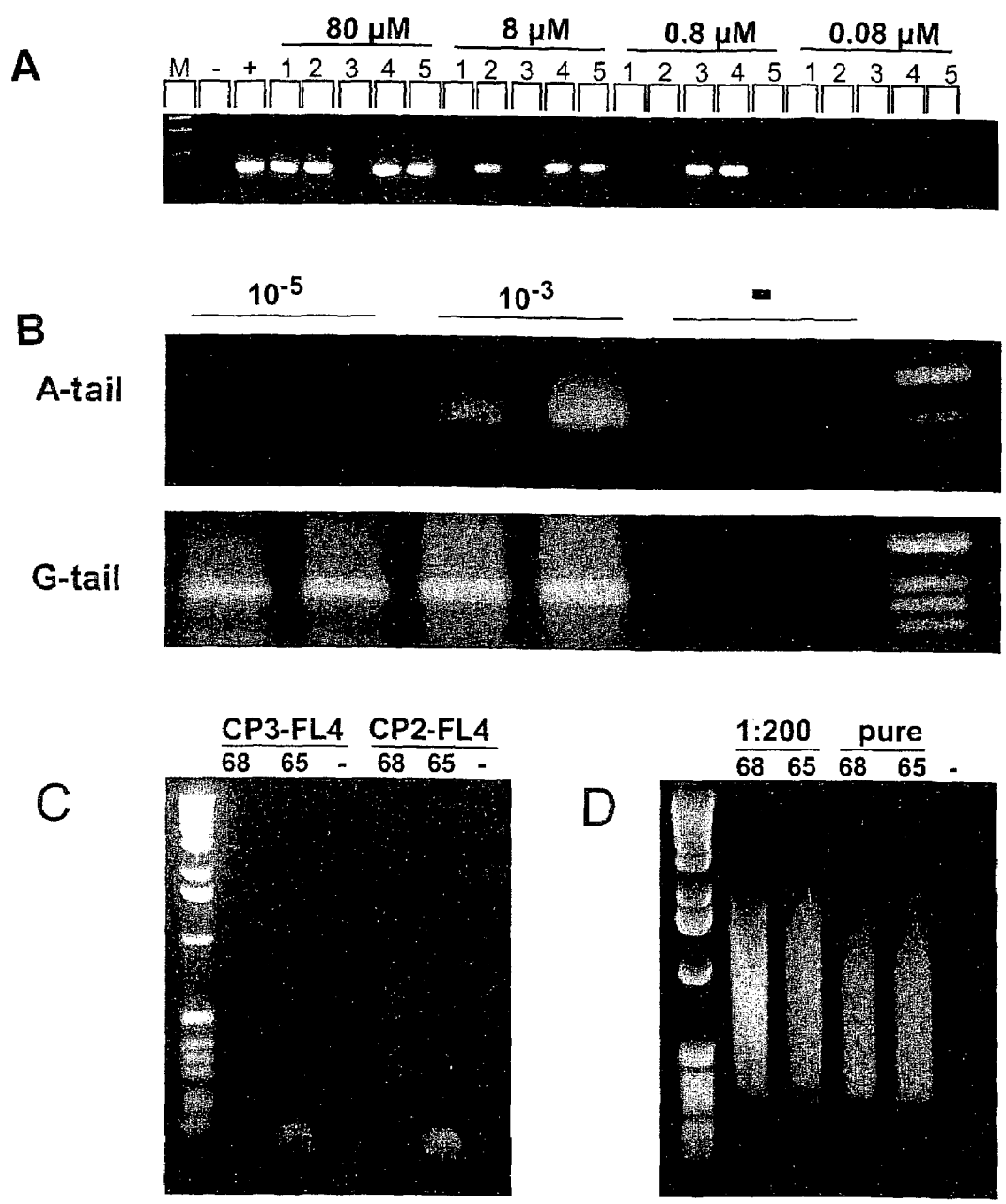
FIG. 1. Parameters determining amplification success. a) Twenty HT29 colon carcinoma cells ((ATCC: HTB-38) lanes 1–20) were individually isolated and mRNA reverse transcribed in the presence of different concentrations of random hexamer primers (lanes 1–5, 80 µM; lanes 6–10, 8 µM; lanes 11–15, 0.8 µM; lanes 16–20, 0.08 µM). 1/10 of the cDNA was subsequently tested for the detection of the ki-ras transcript by gene-specific PCR. b) Influence of the homopolymer tail on sensitivity. A 350 bp TGF-α fragment was isolated, diluted and either dA or dG tailed. Serial dilutions were tested by PCR using poly-dT or poly-dC containing primers, respectively, and a primer within the TGF-α sequence. The informative dilutions are shown in duplicates. (lanes 1+2, negative control; lanes 3+4, $10^{-3}$ dilution; lanes 5+6, $10^{-5}$ dilution). c) FL4-N6 primed and revers transcribed mRNA was dG-tailed and amplified using the CP3+FL4 primers (lanes 1–3) or CP2+FL4 primers at different annealing temperatures (lane 1+4, 68° C., lane 2+5 65° C., lane 3+6, negative control). d) An identical amount of mRNA as in c) was reverse transcribed using the CFL5cN6 primer, and amplified with the CP2 primer. An equal amount of cDNA as in c) (lane 3+4) resulted in amplification of a wide range of cDNA fragments as did a 1:200 dilution (lane 1+2) at different annealing temperatures (lane 1+3, 68° C.; lane 2+4, 65° C.; lane 5, negative control).

Furthermore, concentrations of random primers were 2000–8000-times higher for cDNA synthesis compared to previously desribed oligo-dT-based approaches (Brady, Methods. Enzymol., 225, 611–623 (1993); Trumper, Blood, 81, 3097–3115 (1993)), who employed 10 nM cDNA synthesis primers. Twenty HT29 colon carcinoma cells (ATCC: HTB-38) were individually isolated and processed. After cell lysis in cDNA synthesis buffer containing the detergent Igepal, groups of five cells were formed and reverse transcribed with four different concentrations of random cDNA synthesis primers. By gene-specific RT-PCR cDNA synthesis was tested for each concentration. FIG. 1a shows that higher concentrations of random primers for cDNA synthesis lead to increased detection rates of specific transcripts (e.g. ki-ras). Surplus primer, being an effective competitor of the subsequent tailing and amplification reaction, was, therefore, preferably removed prior to both steps. Equally, high dNTP concentrations improved cDNA synthesis but interfered with the subsequent tailing reaction and needed to be removed. Standard cacodylate-containing tailing buffer interfered with the following PCR and was replaced with a KH2PO4 buffer of low ionic strength (Nelson, Methods Enzymol., 68, 41–50 (1979). Capturing of mRNA on oligo-dT coated magnetic beads provided for simple handling during mRNA isolation and buffer exchange steps. In the following, the isolation of single cells, mRNA isolation, cDNA synthesis and 3'-tailing is briefly described and exemplified.

Tumor cells were isolated from bone marrow as described (Klein, Proc. Natl. Acad. Sci. USA, 96, 4494–4499 (1999)). Briefly, viable bone marrow samples were stained for 10 min. with 10 µg/ml monoclonal antibody 3B10-C9 in the presence of 5% AB-serum to prevent unspecific binding. 3B10-positive cells were detected with B-phycoerythrin-conjugated goat antibody to mouse IgG (The Jackson Laboratory) and transferred to PCR-tubes on ice. Oligo-dT beads were added, the cells lysed in 10 µl lysis buffer (Dynal), tubes rotated for 30 min. to capture mRNA. 10 µl cDNA wash buffer-1 (Dynal) containing 0.5% Igepal (Sigma) was added and mRNA bound to the beads washed in cDNA wash buffer-2 (50 mM Tris-HCl, pH 8,3, 75 mM KCl, 3 mM $MgCl_2$, 10 mM DTT, supplemented with 0.5% Tween-20 (Sigma)), transferred to a fresh tube and washed again in cDNA wash buffer-1 to remove any traces of LiDS and genomic DNA. mRNA was reverse transcribed with Superscript II Reverse Transcriptase (Gibco BRL) using the buffers supplied by the manufacturer supplemented with 500 µM dNTP, 0.25% Igepal, 30 µM Cfl5c8 primer (5'-$(CCC)_5$ GTC TAG $ANN(N)_6$-3') and 15 µM CFL5cT (5'-$(CCC)_5$ GTC TAG ATT $(TTT)_4$ TVN, at 44° C. for 45 min. Samples were rotated during the reaction to avoid sedimentation of the beads. cDNA remained linked to the paramagnetic beads via the mRNA and washed once in the tailing wash buffer (50 mM $KH_2PO_4$, pH 7.0, 1 mM DTT, 0.25% Igepal). Beads were resuspended in tailing buffer (10 mM $KH_2PO_4$, pH 7.0, 4 mM $MgCl_2$, 0.1. mM DTT, 200 µM GTP) and cDNA-mRNA hybrids were denatured at 94° C. for 4 min, chilled on ice, 10 U TdT (MBI-Fermentas) added and incubated at 37° C. for 60 min or 37° C., 60 min and 22° C. over night. After inactivation of the tailing enzyme (70° C., 5 min), PCR-Mix I was added consisting of 4 µl of buffer 1 (Roche, Taq long template), 3% deionized formamide (Sigma) in a volume of 35 µl. The probes were heated at 78° C. in the PCR cycler (Perkin Elmer 2400), PCR Mix II, containing dNTPs at a final concentration of 350 µM, CP2 primer (5'-TCA-GAA-TTC-ATG-CC-CCC-CCC-CCC-CCC-3', final concentration 1.2 µM) and 5 Units of the DNA Poly-Mix was added, (Roche, Taq Long Template) in a volume of 5 µl for a hot start procedure. Forty cycles were run at 94° C., 15 sec, 65° C., 30° C., 68° C., 2 min for the first 20 cycles and a 10 sec-elongation of the extension time each cycle for the remaining 20 cycles, and a final extension step at 68° C., 7 min. These PCR amplification conditions differ substantially from Brail, Mut. Res. Genomics, 406, 45–54 (1999). Annealing temperature in Brail is only 42° C. for 2 min in contrast to the 65° C. applied in this example of method of invention.

Tailing efficiency as well as the sensitivity of the subsequent PCR of poly-dA- and poly-dG-tailed sequences was assessed using a defined cDNA fragment with a homopolymer tail of either poly-dA or poly-dT. The poly-(dA) and poly-(dG)-tailed fragments were diluted and then amplified by PCR using equal amounts of poly(dT) and poly(dC) primers, respectively. In these experiments poly-C primers binding to poly-G tails were found to be at least 100-times more sensitivity than poly-T primers on poly-dA tails (FIG. 1b compare lanes 1,2 to 3,4)

Various cDNA synthesis primers sharing the same poly-dC flanking region in combination with random hexamers (N6), octamers (N8), oligo-dT $(dT)_{15}$ alone or in combination were compared. All worked well and reliably. The best results were obtained with a combination of poly-dC-N8 and poly-dC-$(dT)_{15}$ primers (data not shown).

The most dramatic improvement was obtained when only one primer (FIG. 1c) was used for global PCR instead of two (FIG. 1d). The cDNA synthesis primer consisted of a 3' random hexamer and flanking region either a poly-dC stretch (CFl5c) or a flanking sequence of all four bases (Fl4N6). Two poly-dC binding primers were tested in combination with an additional primer binding to Fl4 complementary sequence (FIG. 1c). Use of an additional primer (FL4) to the poly-dC binding primers (CP2, CP3) prevented amplification (FIG. 1c, lanes 1,2 and 4,5). This is likely due to the high primer concentrations required for optimal sensitivity. The use of the CP2 primer alone resulted in amplification of a wide range of cDNA molecules (0.2–3 kB). Even highly diluted cDNA (1:200) was still sufficient for global amplification (FIG. 1d).

EXAMPLE II

Transcriptome Analysis of Singi Cells: Specificity, Reproducibility, Sensitivity, and Suitability for cDNA Array Analysis Isolated single cells from cultured cell lines were analyzed by the optimized protocol for cDNA synthesis, tailing and amplification. A total of 100 single cells have so far been successfully tested for β-actin and EF-1α expression by gene-specific PCR (data not shown). cDNAs for housekeeping genes were found in a sufficient copy number per cell to be relatively independent of the region used for specific amplification in the secondary PCR. For less abundant transcripts, it was noted that the size of the chosen coding sequence determined detection rates. Highest sensitivity was obtained with the two primers being separated by less than 200 bp (data not shown).

The PCR amplificates from single cells were tested for suitability of cDNA array analysis. For this purpose, the obtained cDNA was Dig(Digoxigenin)-labeled. Dig-UTP was incorporated by PCR. For expression profiling 0.1–1 µl of the original PCR amplified cDNA fragments were used for reamplification in the presence of digoxigenin-labeled dUTP (Boehringer Mannheim), 50 µM dig-dUTP, 300 µM dTTP, and other dNTPs at a final concentration of 350 µM. Reamplification conditions were essentially as described above, modifications were the use of 2.5 Units of the DNA Poly Mix. Initial denaturation at 94° C. for 2 min. followed by 12 cycles at 94° C., 15 sec, 68° C., 3 min and a final extension time of 7 min. Specific transcripts were detected using 1 µl of a 1/10 dilution of the original PCR to a final volume of 10 µl.

The specificity of the hybridization of digoxigenin-labeled probes is depicted in Table 1, where the expression pattern of genes from single cells of different histogenetic origin are shown. Cells were MCF-7 (ATCC Number HTB-22), A431 (ATCC Number CRL-1555), K-562 (ATCC Number CCL-243), JY (International Histocompatibility Workshop: IHW9287). Only the MCF-7 and A431 cell expressed the cytokeratin genes, markers for their epithelial origin, whereas the erythroleukemia K562 cell and EBV-transformed B cell JY expressed genes of a haematopoetic origin, including CD33, CD37, CD38, and kappa light chain in the B cell. In addition, the testis- and tumor-specific MAGE genes were highly expressed in all cancer cells but not the virally transformed B cell. These data show that single cell PCR amplificates are useful for cDNA array analysis and produce cell type-specific gene expression patterns of single cells.

TABLE 1

Expression of histogenetically informative genes by single cells derived from different tissues.

|  | MCF-7 | A431 | K562 | JY |
|---|---|---|---|---|
| Aktin | + | + | + | + |
| EF-1a | + | + | + | + |
| CK7 | + | + | − | − |
| CK10 | − | + | − | − |
| CK13 | − | + | − | − |
| CK18 | + | + | − | − |
| CK19 | + | + | − | − |
| EGP | + | + | − | − |
| CD33 | − | − | + | + |
| CD37 | − | − | + | + |
| CD38 | − | − | + | − |
| Kappa | − | − | − | + |
| Vimentin | − | + | + | − |
| α-6 Integrin | + | − | − | − |
| β-1 Integrin | + | − | − | − |
| β-2 Integrin | − | − | − | + |
| β-4 Integrin | − | − | + | − |
| β-7 Integrin | − | − | − | + |
| FAK | + | − | − | − |
| Mage1 | + | − | + | − |
| Mage2 | + | + | + | − |
| Mage3 | + | − | + | − |
| Mage6 | + | − | + | − |
| Mage12 | + | + | + | − |

Individual cells grown in culture were isolated, cDNA synthesized, amplified and hybridized to an array of histogenetically informative genes. Cells were from the following cell lines MCF-7 (breast cancer); A431 (epidermoid carcinoma); K562 (chronic myeloid leukemia); JY (Epstein-Barr virus transformed B cell line).

In order to assess reproducibility, the expression pattern of four MCF-7 cells were compared using a cDNA array Generation 4 with 110 different genes (Table 2). Custom made cDNA arrays were prepared as follows. cDNAs were PCR-amplified with gene-specific primers from human cDNA, PCR amplificates were gel-purified and 15 ng DNA per amplificate was spotted onto nylon membranes (Boehringer) using a BioGrid spotting robotic device (Biorobotics). DNA Macroarrays were termed Generation 4 and Generation 5 (see herein below).

Filter Generation 4: Spotted Genes were:

| Protein Name | HUGO Name | Protein Name | HUGO Name |
|---|---|---|---|
| Cytokeratin 7 | KRT7 | slap | SLA |
| Cytokeratin 8 | KRT8 | p21 | CDKN1A |
| Cytokeratin 10 | KRT10 | p68 | |
| Cytokeratin 13 | KRT13 | p27 | CDKN1B |
| Cytokeratin 18 | KRT18 | Eck | EPHA2 |
| Cytokeratin 19 | KRT19 | P33 | ING1 |
| Cytokeratin 20 | KRT20 | B61 | EFNA1 |
| Emmprin II | BSG | p53 III | TP53 |
| MT1-MMP | MT1-MMP | E-Cad | CDH1 |
| MT2-MMP | MT2-MMP | p53 IV | TP53 |
| MT3-MMP | MT3-MMP | P-Cad | CDH3 |
| MT4-MMP | MT4-MMP | p57 | CDKN1C |
| TIMP1 | TIMP1 | N-Cad | CDH2 |
| TIMP2 | TIMP2 | Cyclin D | CCND1 |
| TIMP4 | TIMP4 | c-myc I | MYC |
| MMP1 | MMP1 | Gas1 | GAS1 |
| uPA | PLAU | c-myc II | MYC |

-continued

| Protein Name | HUGO Name | Protein Name | HUGO Name |
|---|---|---|---|
| uPA-Rezeptor | PLAUR | Ki-67 | MKI67 |
| PAI1 | PAI1 | RB | RB1 |
| PAI2 | PAI2 | b-Aktin | ACTB |
| CathepsinB | CTSB | HTK | TK1 |
| CathepsinD | CTSD | EF-1a | EEF1A1 |
| CathepsinL | CTSL | RAD 51 | RAD51 |
| Stromelysin1 | MMP3 | A20 | TNFAIP3 |
| Stromelysin3 | MMP11 | Nck | NCK1 |
| Gelatinase A | MMP2 | BCL-2 | BCL2 |
| Gelatinase B | MMP9 | pBS | |
| Matrilysin | MMP7 | GAPDH | GHPDH |
| Cystatin 1 | CSTA | hEST | TERT |
| Cystatin 2 | CSTB | Mage 1 | MAGEA1 |
| Cystatin 3 | CST3 | TSP-1 | THBS1 |
| ADAM 8 | ADAM8 | Mage 3 | MAGEA3 |
| ADAM 9 | ADAM9 | mrp-1 | ABCC1 |
| ADAM 10 | ADAM10 | Mage 4 | MAGEA4 |
| ADAM 11 | ADAM11 | mdr-1 | ABCB1 |
| ADAM 15 | ADAM15 | Mage 6 | MAGEA6 |
| ADAM 20 | ADAM20 | DEP-1 | PTPRJ |
| ADAM 21 | ADAM21 | Mage 12 | MAGEA12 |
| TACE | ADAM17 | PTP-μ | PTPRM |
| a4-Integrin | ITGA4 | Mage1F | MAGEA1 |
| a5-Integrin | ITGA5 | Creatin Kinase | CKM |
| a6-Integrin | ITGA6 | Mage2F | MAGEA2 |
| av-Integrin | ITGAV | Mage 4F | MAGEA4 |
| GFP | | Mage3F | MAGEA3 |
| beta-Actin | ACTB | Mage 12F | MAGEA12 |
| b1-Integrin | ITGB1 | CD16 | FCGR3A |
| b2-Integrin | ITGB2 | TGF-a | TGFA |
| b3-Integrin | ITGB3 | CD33 | CD33 |
| b4-Integrin | ITGB4 | TGF-b | TGFB1 |
| b5-Integrin | ITGB5 | CD34 | CD34 |
| b7-Integrin | ITGB7 | VEGF | VEGF |
| p15 | CDKN2B | CD37 | CD37 |
| Fak | PTK2 | IGF-I | IGF1 |
| p16 | CDKN2A | CD38 | CD38 |
| Ramp-1 | | kappa | IGKC |
| CD40 | CD40 | TGF-b R.II | TGFBR1 |
| Ramp-2 | | lambda | IGLC1 |
| CD45 II | PTPRL | IGF-RI | IGFR1 |
| EMM I | BSG | Vimentin | VIM |
| CD83 | CD83 | IGF-RII | IGFR2 |
| GFP | | EGP-1 | M4S1 |
| pBS | | MUC 18 | MCAM |
| erb B2 | ERBB2 | DP-I | DSP |
| TCR | TCRA | PHRIP | PHLDA1 |
| TGF-b Rez.I | TGFBR1 | CEA | CEA |
| | | EF-1a | EEF1A1 |

TABLE 2

Commonly and differentially expressed genes of four single MCF-7 cells.

| 4/4 | 3/4 | 2/4 | 1/4 |
|---|---|---|---|
| EF-1a | CK19 | Beta-4-Integrin | CK10 |
| GAPDH | TIMP-1 | Beta-5-Integrin | CK13 |
| b-Actin | Cathepsin B | P53 | ADAM 9 |
| CK7 | Cathepsin D | Creatin Kinase | ADAM 15 |
| CK8 | Cathepsin L | | ADAM17 (TACE) |
| CK18 | ADAM 10 | | p16 |
| CK20 | c-myc | | p21 |
| Alpha 6-Integrin | | | p27 |
| Beta1-Integrin | | | p33 |
| Fak | | | ki-67 |
| EMMPRIN | | | hTK |
| u-PAR | | | E-cadherin |
| Matrilysin | | | IGF-R I |
| Cyclin D1 | | | IGF-R II |

TABLE 2-continued

Commonly and differentially expressed genes of four single MCF-7 cells.

| 4/4 | 3/4 | 2/4 | 1/4 |
|---|---|---|---|
| Eck | | | TGF-beta |
| EpCAM | | | VEGF |
| Mrp-1 | | | DP-I |
| PHRIP | | | |

Heterogeneity of gene expression of individual cells derived from the same cell clone. Four MCF-7 cells isolated from cell culture were analyzed by single cell analysis of gene expression. Listed are the transcripts that were detected in all four single cells (4/4), three of four (3/4), two of four (2/4), and one of four (1/4). 18/46 (39%) expressed genes were detected in all cells. 61% genes could only found in a portion of the four cells. 63 genes were negative for all cells tested.

Figure 2:
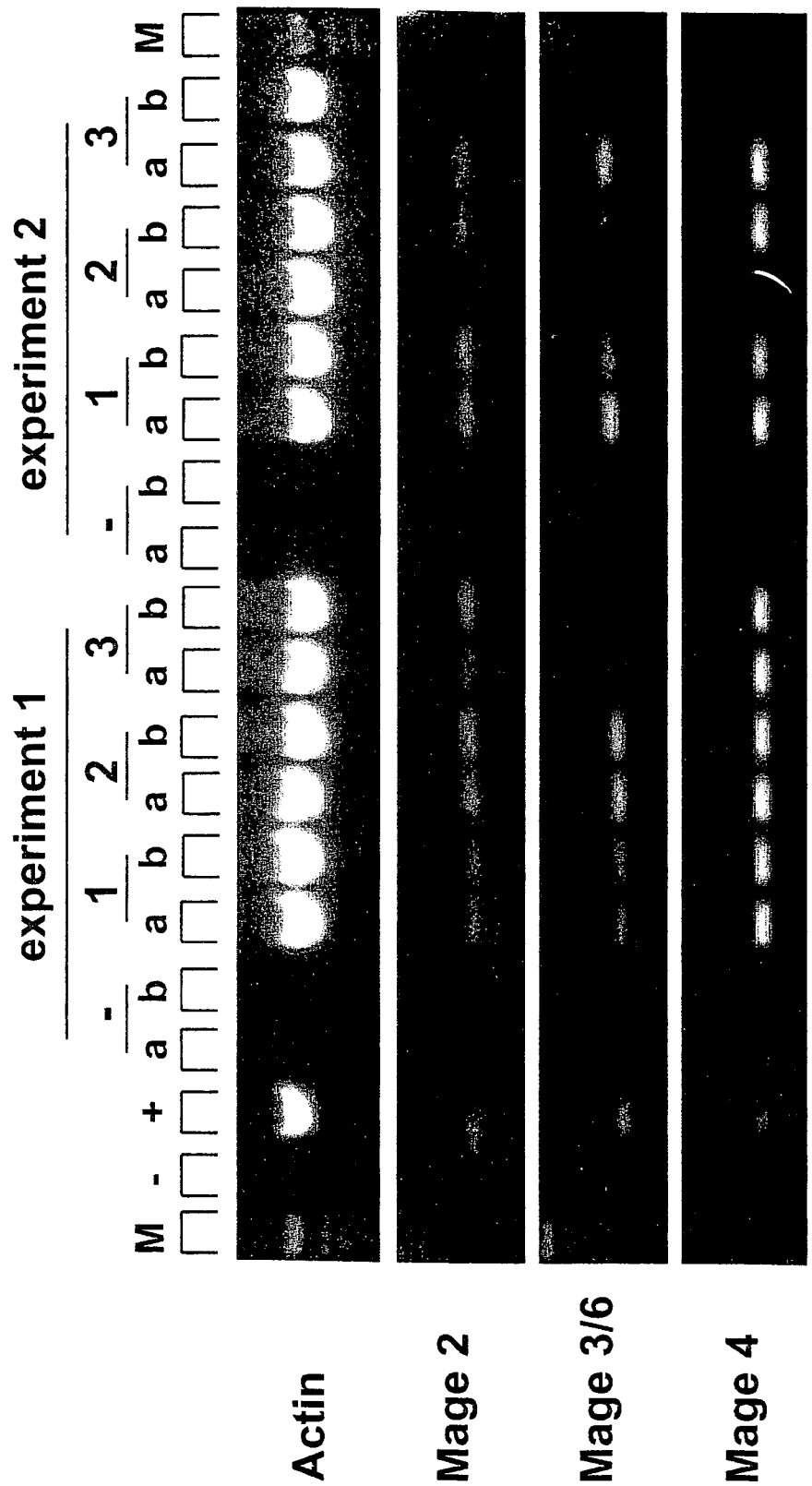
FIG. 2. Gene specific PCR for β-actin and various MAGE transcripts using unamplified pooled cDNA of A431 cells as positive control (+) and amplificates of single A431 cells (lane 2–4 and 6–8) that were divided into two halves (a+b) before global PCR. Two independent experiments were performed (lane 1–4 and 5–8) with lane 1 and lane 5 being the negative controls for the global PCR.

46 genes (42%) were expressed in at least one cell and 63 (58%) were negative for all four cells. Eighteen of the 46 (39%) expressed genes were detected in all four cells whereas the remaining 29 (61%) were found to be heterogeneously expressed. To evaluate whether this heterogeneity was due to intercellular variation or is an artifact of the technique, it was tested whether disparity is also observed with the cDNA of a single A431 cell that was split for two separate PCR amplifications. In a first experiment, gene-specific PCRs with the globally amplified PCR products obtained from 50% of single cell cDNA (FIG. 2) were performed. For comparison, cDNA isolated from a pool of 500.000 A431 cells were diluted to such an extent that the intensity of the β-actin band was similar to that obtained with 50% of the single cell cDNA. After 32 cycles and with a cDNA amount corresponding to about 10.000 cells, the β-actin signal of the pool control and 50% of the single cell cDNA reached the plateau phase of amplification. As shown in FIG. 2, the variation between two cDNA halves of the same cell was very low. In two independent experiments, each half (a+b) from six A431 cells yielded β-actin bands of similar intensity.

In order to test the reliability of the global amplification of the cDNA, a second gene sequence-specific PCR amplification was perfomed. As the efficiency of gene-specific PCR amplification is known to be primer sequence-dependent, the amplification of MAGE transcripts was tested, which are very demanding with respect to primer design (Kufer, WO98/46788 (1998); Serrano, Int. J. Cancer 83, 664–669 (1999)). The level of MAGE expression determined by sequence specific PCR was consistently lower than that of beta-actin. The relative abundance of MAGE transcripts in split single cell samples after global PCR amplification of the cDNA (FIG. 2, lanes 2–4 and 6–8) was comparable to that of the control sample from unamplified cDNA from pooled cells (FIG. 2, +). In 4 out of 6 cases, the results were identical for both halves of the cDNA. The lack of any MAGE transcript in cell half 7a and 8b most likely indicates an unequal distribution of the cDNAs between the two halves.

The observed sequence-independent amplification is characteristic of the poly-dC primer, which contains fifteen cytosine residues and therefore introduces primer binding sites with equally high CG-content. The experimental conditions suited for such a primer, i.e. high annealing temperature (65° C.) in the presence of 3% denaturing formamide, lead, to a remarkable reproducibility and did not introduce major quantitative changes to the single cell transcriptome.

Amplificates from split single cell cDNAs and, as control, cDNA from 5,000 pooled cells were labeled and hybridized to a cDNA array representing 193 different genes. Most transcripts could be detected with both halves of the single cell amplificates (Tab. 3).

Table 3: Gene expression patterns of single cells split in two pols of cDNA prior to global PCR compared to pooled cDNA of 5000 cells.

TABLE 3

| | 1.1 | 1.2 | + | | 2.1 | 2.2 | + |
|---|---|---|---|---|---|---|---|
| GFP | | | | GFP | | | |
| pBS | | | | pBS | | | |
| ACTB | ■ | ■ | ■ | ACTB | ■ | ■ | ■ |
| GHPDH | ■ | ■ | ■ | GHPDH | ■ | ■ | ■ |
| KRT10 | ■ | ■ | ■ | TUBA | ■ | ■ | ■ |
| KRT13 | ■ | ■ | ■ | PLD1 | ■ | ■ | ■ |
| KRT18 | ■ | ■ | ■ | rfx-1 | ■ | ■ | |
| KRT19 | ■ | ■ | ■ | ELF3 | ■ | ■ | |
| BSG (I) | ■ | ■ | ■ | EEF1A1 | ■ | ■ | ■ |
| BSG (II) | ■ | ■ | ■ | M4S1 (III) | ■ | ■ | ■ |
| UB | ■ | ■ | ■ | M4S1 (I) | ■ | ■ | ■ |
| EEF1A1 | ■ | ■ | ■ | MAGEA4(I) | ■ | ■ | ■ |
| MAGEA4(I) | ■ | ■ | ■ | UB | ■ | ■ | ■ |
| ITGB4 | ■ | ■ | ■ | CLDN7 | ■ | ■ | ■ |
| TUBA | ■ | ■ | ■ | KRT7 | ■ | ■ | ▨ |
| PLD1 | ■ | ■ | ■ | KRT10 | ■ | ■ | ■ |
| ITGB1 | ■ | ■ | ■ | KRT13 | ■ | ■ | ■ |
| TK1 | ■ | ■ | ▨ | KRT18 | ■ | ■ | ■ |
| CCND1 | ■ | ■ | ▨ | KRT19 | ■ | ■ | ■ |
| ELF3 | ■ | ■ | ■ | PLAU | ■ | ■ | ▨ |
| KRT7 | ■ | ■ | ▨ | CTSD | ■ | ■ | ■ |
| TIMP1 | ■ | ■ | ■ | ICAM | ■ | ■ | ■ |
| CLDN7 | ■ | ▨ | ■ | PHLDA1 | ■ | ■ | |
| PLAU | ■ | ▨ | ▨ | CCND1 | ■ | ■ | ▨ |
| CTSD | ■ | ■ | ■ | PTMA | ■ | ■ | ■ |
| CTSB | ■ | ■ | ■ | VEGF | ■ | ■ | ■ |
| CTSL | ■ | ■ | ▨ | MAGEA1(I) | ■ | ■ | |
| M4S1 (I) | ■ | ■ | ■ | MAGEA4(II) | ■ | ■ | ▨ |
| M4S1 (III) | ■ | ■ | ■ | MYC | ■ | ■ | ▨ |
| PTMA | ■ | ■ | ■ | M4S1 (II) | ■ | ■ | |
| PHB | ■ | ■ | ■ | M4S1 (IV) | ■ | ■ | ▨ |
| TP53(I) | ■ | ■ | ■ | TGFA | ■ | ■ | |
| TP53 (II) | ■ | ■ | ■ | CSTB | ■ | ▨ | ▨ |
| ICAM | ■ | ■ | ■ | TP53(I) | ■ | ▨ | ■ |
| CD44 | ■ | ■ | ■ | MYC(III) | ■ | ▨ | ▨ |
| CSTA | ■ | ■ | ■ | TMP21 | ■ | ▨ | |
| IGFR2 | ■ | ▨ | ■ | ADAM10 | ■ | ▨ | ▨ |
| ADAM17 | ■ | ■ | ▨ | ING1 | ■ | ▨ | ▨ |
| CSTB | ■ | ■ | ▨ | CSTA | ■ | ■ | |
| ERBB2 | ■ | ■ | ▨ | MAGEA12(I) | ▨ | ■ | |
| MAGEA4(II) | ■ | ■ | ▨ | MAGEA1(II) | ▨ | ■ | |
| MYC(III) | ■ | ■ | ▨ | TEK | ▨ | ▨ | ▨ |
| CDKN1B | ■ | ■ | ▨ | CTSL | ▨ | ▨ | ■ |
| TEK | ■ | ▨ | ▨ | CD44 | ▨ | ▨ | ■ |
| API4 | ■ | ▨ | ▨ | KRT8 | ▨ | ▨ | |
| CDKN1A | ■ | ■ | | MAGEA12(II) | ▨ | ▨ | |
| MAGEA1 | ■ | ■ | | | | | |
| THBS1 | ■ | ■ | | | | | |

TABLE 3-continued

| Gene | 1.1 | 1.2 | Gene | +  | 2.1 | 2.2 |
|---|---|---|---|---|---|---|
| TNFAIP3 | ■ | ■ | PLAUR | ■ | | |
| MAGEA12 | ■ | ▦ | API4 | ■ | | ▦ |
| MAGEA1 | ■ | | MMP3 | ■ | | |
| KRT8 | ▦ | ■ | ITGA5 | ■ | | |
| TMP21 | ▦ | ▦ | CLDN1 | ▦ | | |
| | | | CLDN3 | ▦ | | |
| | | | MT1-MMP | ▦ | | |
| | | | CD45II | ▦ | | |
| VEGF | ■ | ■ | | | | |
| MFGE8 | ■ | ■ | | | | |
| ITGB5 | ■ | ▦ | BSG (I) | ■ | ■ | |
| p68 | ■ | ▦ | BSG (II) | ■ | ■ | |
| PLAUR | ■ | ▦ | PTK2 | ■ | ■ | |
| KIAA169 | ■ | ▦ | ADAM21 | ■ | | |
| CD24 | ■ | ▦ | ADAM9 | ■ | ▦ | |
| MYC (I) | ■ | ▦ | ADAM15 | ■ | | |
| CALM1 | ■ | ▦ | p68 | ■ | ▦ | |
| CDH3 | ■ | | TIMP1 | ■ | ■ | |
| PHLDA1 | ■ | | CDKN1B | ■ | ▦ | |
| MAT8 | ■ | | VIM | ▦ | | |
| ZNF217 | ■ | | CD24 | ▦ | ▦ | |
| PTK2 | ▦ | ▦ | KIA169 | ▦ | | |
| ADAM10 | ▦ | ▦ | ERBB2 | ▦ | ▦ | |
| ADAM9 | ▦ | ▦ | | | | |
| CD40 | ▦ | ▦ | | | | |
| CLDN1 | ▦ | | | | | |
| CLDN3 | ▦ | | CTSB | ■ | | |
| PAI2 | ▦ | | ITGB1 | ■ | | |
| MAGEA2(II) | ▦ | | ITGB4 | ■ | | |
| BTG3 | ▦ | | IGFR2 | ■ | | |
| Decoy-R3 | ▦ | | PHB | ■ | | |
| MAGEA12(II) | ▦ | | TP53(IV) | ■ | | |
| TGM4 | ▦ | | MFGE8 | ■ | | |
| ITGA5 | ▦ | | RARRES3 | ■ | | |
| | | | ITGB5 | ▦ | | |
| | | | CALM1 | ▦ | | |
| RARRES3 | ■ | ■ | TK1 | ▦ | | |
| TRAF4 | ■ | | BAG1 | ▦ | | |
| MTI-MMP | ■ | ▦ | BCL2L1 | ▦ | | |
| MLN64 TRAF4 | ■ | ▦ | MLN64 TRAF4 | ▦ | | |
| EPHA2 | ■ | ▦ | Auto-Ag | ▦ | | |
| TGFB | ▦ | | EPHA2 | ▦ | | |
| | | | EFNA1 | ▦ | | |
| | | | AXL | ▦ | | |
| M4S1 (IV) | ▦ | | TGFBR2 | ▦ | | |
| CSTB | ▦ | | ABCC1 | ▦ | | |
| ING1 | ▦ | | TNFRSF5 | ▦ | | |
| AXL | ▦ | | ADAM17 | ▦ | | |
| EFNA1 | ▦ | | MT1-MMP | ▦ | | |
| Auto-Ag | ▦ | | | | | |
| TGFBR2 | ▦ | | | | | |
| ABCC1 | ▦ | | | | | |
| BAG1 | ▦ | | | | | |
| BCL2L1 | ▦ | | | | | |

The cDNAs of two single cells were split prior to PCR amplification and compared to a cDNA pool derived from 5000 cells. All cDNAs were amplified by global PCR and analyzed by hybridization to a cDNA array. The gene expression profiles of the corresponding halves (1.1 and 1.2; 2.1 and 2.2) are juxtaposed to the cell pool (+). The genes are listed according signal strength (the darker, the stronger) and detection in both halves of the same cell. The filter used was Generation 5, genes and protein names are listed below (for preparation of said Generation 5 filter, see herein above (Generation 4 filter)).

Generation 5 Filter:

| Protein | HUGO |
|---|---|
| A20 | TNFAIP3 |
| a4-Int | ITGA4 |
| a5-Int | ITGA5 |
| a6-Int | ITGA6 |
| ADAM10 | ADAM10 |
| ADAM15 | ADAM15 |
| ADAM21 | ADAM21 |
| ADAM9 | ADAM9 |
| Auto-Ag | SHGC-74292 |
| av-Int | ITGAV |
| Axl | AXL |
| b1-Int | ITGB1 |
| b2-Int | ITGB2 |
| b3-Int | ITGB3 |
| b4-Int | ITGB4 |
| b5-Int | ITGB5 |
| B61 | EFNA1 |
| b7-Int | ITG7 |
| BA46 | MFGE8 |
| BAG1 | BAG1 |
| b-Aktin | ACTB |
| b-Casein | CSN2 |
| Bcl-2 | BCL2 |
| Bcl-xl | BCL2L1 |
| b-micro | MSMB |
| BTG-3/ANA | BTG3 |
| Calmodulin | CALM1 |
| Cathepsin B | CTSB |
| Cathepsin D | CTSD |
| Cathepsin L | CTSL |
| CD16 | FCGR3A |
| CD24 | CD24 |
| CD33 | CD33 |
| CD34 | CD34 |
| CD37 | CD37 |
| CD38 | CD38 |
| CD40 | TNFRSF5 |
| CD44 | CD44 |
| CD45 | PTPRC |
| CD83 | CD83 |
| CEA | CEA |
| CK10 | KRT10 |
| CK13 | KRT13 |
| CK18 | KRT18 |
| CK19 | KRT19 |
| CK7 | KRT7 |
| CK8 | KRT8 |
| Claud1 | CLDN1 |
| Claud3 | CLDN3 |
| Claud7 | CLDN7 |
| c-myc | MYCBP |
| Cyclin D1 | CCND1 |
| Cystatin A | CSTA |
| Cystatin B | CSTB |
| Decoy-R2 | TNFRSF10D |
| Decoy-R3 | TNFRSF6B |
| DEP-1 | PTPRJ |
| DP-1 | DSP |
| E2F6 | E2F6 |
| E-Cad | CDH1 |
| Eck | EPHA2 |
| EF1a | EEF1A1 |
| EGP1 | M4S1 |
| Emmprin | BSG |
| EPC-1 | PEDF |
| erbB2 | ERBB2 |
| Ese1b/ELF3 | ELF3 |
| Fak | PTK2 |
| FGFR1 | FGFR1 |
| FGFRII | FGFR2 |
| Gadd45 | GADD45A |
| GAPDH | GHPDH |
| Gas1 | GAS1 |
| Gas6 | GAS6 |
| GFP | |

-continued

| Protein | HUGO |
| --- | --- |
| hEST | TERT |
| Hevin | HEVIN |
| HTK | TK1 |
| ICAM | ICAM |
| IGF RI | IGFR1 |
| IGF RII | IGFR2 |
| Kappa | IGKC |
| Ki67 | MKI67 |
| KIA169 | |
| Lambda | IGLC1 |
| lot1/hZAC | Hs.75825 |
| Mage1 | MAGEA1 |
| mage12 | MAGEA12 |
| Mage2f | MAGEA2 |
| Mage4 | MAGEA4 |
| MAT8 | PLML |
| Mdr-1 | ABCB1 |
| MLN62 | TRAF4 |
| MLN64 TRAF4 | |
| mrp-1 | ABCC1 |
| MT1-MMP | MT1-MMP |
| Muc 18 | MCAM |
| N-Cad | CDH2 |
| Nck | NCK1 |
| p15 | CDKN2B |
| p16 | CDKN2A |
| p21 | CDKN1A |
| p27 | CDKN1B |
| p33 | ING1 |
| p53III | TP53 (III) |
| p53IV | TP53 (IV) |
| p57 | CDKN1C |
| p68 | |
| PAI-2 | PAI2 |
| pBS | |
| P-Cad | CDH3 |
| Phospholipase | PLD1 |
| Phrip | PHLDA1 |
| PIP | PIP |
| Prohibitin | PHB |
| Prost.Spec.Homeo. | Hs.73189 |
| Prost.Spec.Transglu | TGM4 |
| Prost.Spec.Uro. | UPK3 |
| Prothym alpha | PTMA |
| PSA | KLK3 |
| PTHrP | |
| PTP-μ | PTPRM |
| RB | RB1 |
| rfx-1 | RFX1 |
| Slap | SLA |
| Stromelysin 1 | MMP3 |
| Survivin | API4 |
| TACE | ADAM17 |
| TCR | TCRA |
| TGF-alpha | TGFA |
| TGF-beta | TGFB1 |
| TGFB-RI | TGFBR1 |
| TGFB-RII | TGFBR2 |
| TIE-2/Tek | TEK |
| TIG3 | RARRES3 |
| Timp1 | TIMP1 |
| TMP21 | TMP21 |
| TSP-1 | THBS1 |
| Tubulin-a | TUBA |
| Ubiquitin | UB |
| uPA | PLAU |
| uPA-R | PLAUR |
| VEGF | VEGF |
| Vimentin | VIM |
| VLDLR | VLDLR |
| ZNF217 | ZNF217 |
| | Hs.46452 |

A total of 148 signals were obtained for the four cDNA halves. Of these, 95 (64%) were found in the corresponding halves, whereas 53 (36%) were found in only one half. Out of the 53 single positive signals 46 (87%) represented very low-abundant transcripts, with 26 (49%) not detectable and 20 (37%) only weakly expressed in the control of pooled cells. Seven genes (AXL, BAG1, BCL2L1, SHGC-74292, B61, TGFBR2 and ABCC1) were exclusively detected in the pooled sample, though with a rather weak signal. In contrast, 33 genes were only found in the half-cell experiments but not in the control. The signal intensity of the both halves was quite similar, with 55% and 76% of the signals having the same strength in the corresponding halves. Signals that were not identical in two corresponding halves may arise from of a non-random distribution of cDNA fragments prior to PCR. Particularly transcripts present in low (<10) copy number may be subject to such a distribution effect which, however, may not be obtained if samples are not split.

EXAMPLE III

Combined Transcriptome and Genome Analysis from Single Cells

A method of CGH (comparative genomic hybridization) analysis of single cells (SCOMP) was recently described (Klein, Proc. Natl. Acad. Sci. USA, 96, 4494–4499 (1999)). Using this method, a tumor cell can unambiguously be identified by its chromosomal aberrations. It was therefore attempted to isolate both genomic DNA and mRNA from the same cell. Isolated single cells were lysed in 10 μl lysis buffer (Dynal) and tubes rotated for 30 min. to capture mRNA. 10 μl cDNA wash buffer-1 (50 mM Tris-HCl, pH 8,3, 75 mM KCl, 3 mM $MgCl_2$, 10 mM DTT, supplemented with 0.5% containing 0.5% Igepal (Sigma)) was added and mRNA bound to the beads washed in cDNA wash buffer-2 (50 mM Tris-HCl, pH 8,3, 75 mM KCl, 3 mM $MgCl_2$, 10 mM DTT, supplemented with 0.5% Tween-20 (Sigma)), transferred to a fresh tube and washed again in cDNA wash buffer-1 to remove any traces of LiDS and genomic DNA. mRNA was reverse transcribed with Superscript II Reverse Transcriptase (Gibco BRL) using the buffers supplied by the manufacturer supplemented with 500 μM dNTP, 0.25% Igepal, 30 μM Cfl5c8 primer (SEQ ID NO:9) (5'-$(CCC)_5$ GTC TAG A $(N)_8$-3') and 15 μM CFL5cT (SEQ ID NO:10) (5'-(CCC)5 GTC TAG ATT $(TTT)_4$ TVN, at 44° C. for 45 min. Samples were rotated during the reaction to avoid sedimentation of the beads. Primers used and mentioned in FIGS. 1c and d were Cfl5cN6 (SEQ ID NO:8) (5'-$(CCC)_5$ GTC TAG A $(N)_6$-3') and FL4N6 (SEQ ID NO:6) 5'-TTT CTC CTT AAT GTC ACA GAT CTC GAG GAT TTC $(N)_6$-3'). cDNA remained linked to the paramagnetic beads via the mRNA and washed once in the tailing wash buffer (50 mM $KH_2PO_4$, pH 7.0, 1 mM DTT, 0.25% Igepal). Beads were resuspended in tailing buffer (10 mM $KH_2PO_4$, pH 7.0, 4 mM $MgCl_2$, 0.1 mM DTT, 200 μM GTP) and cDNA-mRNA hybrids were denatured at 94° C. for 4 mm, chilled on ice, 10 U TdT (MBI-Fermentas) added and incubated at 37° C. for 60 mm or 37° C., 60 mm and 22° C. over night. After inactivation of the tailing enzyme (70° C., 5 mm), PCR-Mix I was added consisting of 4 μl of buffer 1 (Roche, Taq long template), 3% deionized formamide (Sigma) in a volume of 35 μl. The probes were heated at 78° C. in the PCR cycler (Perkin Elmer 2400), PCR Mix II, containing dNTPs at a final concentration of 350 μM, CP2 primer (SEQ ID NO:14) (5'-TCA-GAA-TTC-ATG-CCC-CCC-CCC-CCC-CCC-3', final concentration 1.2 μM) and 5 Units of the DNA Poly-Mix was added, (Roche, Taq Long Template) in a volume of 5 μl for a hot start procedure. Forty cycles were run at 94° C., 15 sec, 65° C., 30° C., 68° C., 2 mm for the first 20 cycles and a 10 sec-elongation of the extension time each cycle for the remaining 20 cycles, and a final extension step at 68° C., 7 mm. PCR primers used in FIG. 1c were CP3 (SEQ ID NO:15) (5'-GCT GAA GTG GCG AAT TCC GAT GCC $(C)_{12}$-3') and FL4 (SEQ ID NO:16) (5'-CTC CTT AAT GTC ACA GAT CTC GAG GAT TTC-3').

The supernatants from the cell lysis and all washing steps (cDNA wash buffer 1 and 2) of the mRNA isolation were collected (total volume 60 µl). After transfer to a silanised tube the genomic DNA was ethanol precipitated overnight at −20° C. in the presence of 20 µg glycogen (Roche). All subsequent steps were performed as published (Klein, (1999), loc. cit.).

Figure 3:
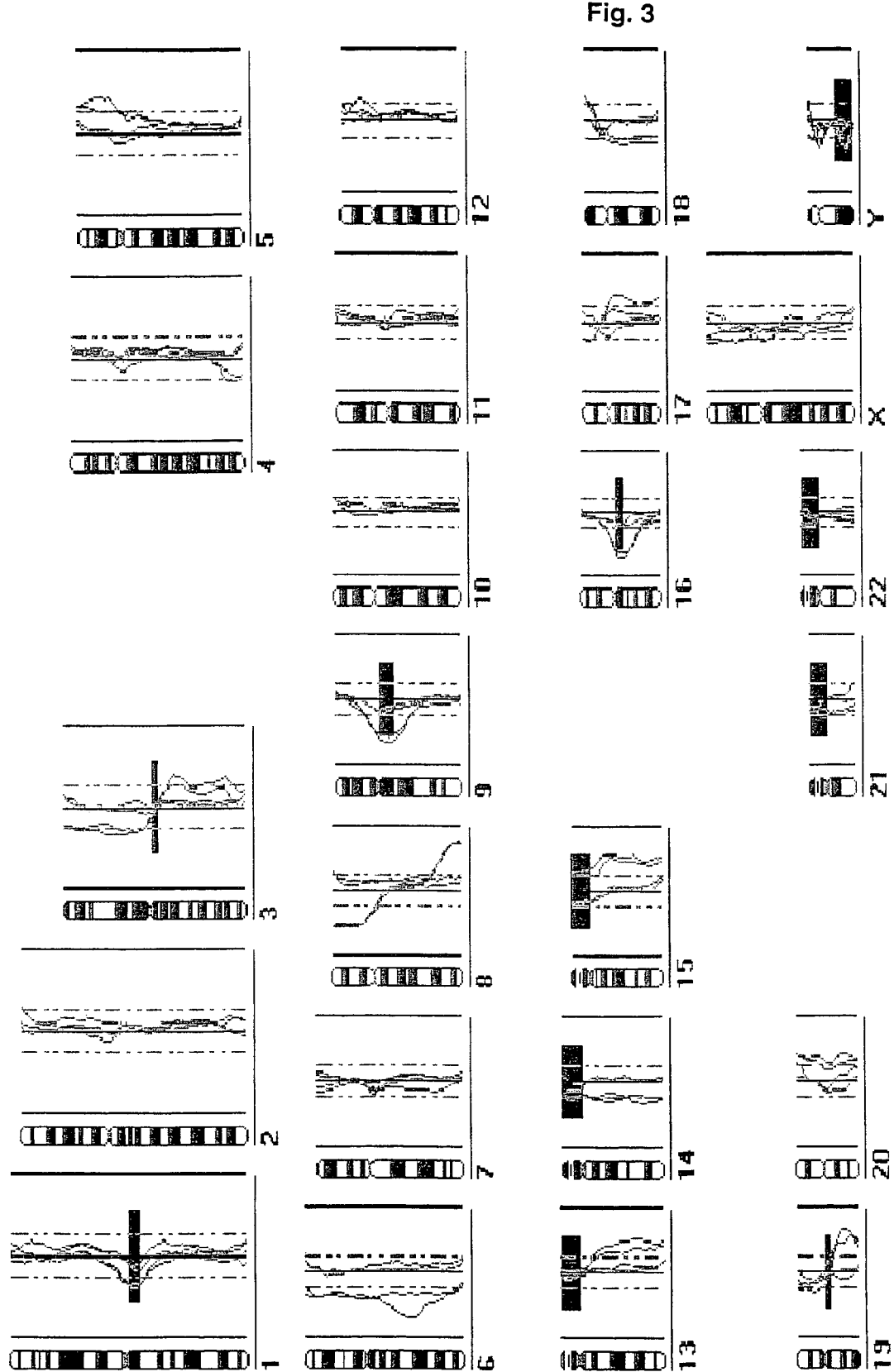
FIG. 3. CGH profiles of two normal leukocytes (red) and two MCF-7 breast cancer cells (blue) of which the genomic DNA was isolated from the supernatant after mRNA isolation. The chromosomal ratios of the normal cells are within the dashed lines, giving the threshold for significance, whereas the profiles of the cancer cells are similar with regard to their chromosomal deletions and amplifications.

A major concern was incomplete precipitation of genomic DNA eventually leading to losses of DNA as seen with chromosome deletions in cancerous cells. However, experiments with cells of a defined karyotype clearly showed that either the cellular DNA was totally lost (30% of cases) or completely precipitated (70%) (data not shown). The complete recovery of genomic DNA may be due to the fact that interphase chromosomes are extensively interwoven so that either all or none is precipitated. The loss of all DNA is probably introduced by the change of reaction tubes during the separation of genomic DNA and mRNA. The karyotypes of two normal and two MCF-7 breast cancer cells whose DNA had been precipitated are shown in FIG. 3. The profiles of the two normal cells showed no significant deviation from the midline while the multiple genomic aberrations of the two MCF-F7 cells were almost identical. Hence, malignant EpCAM-positive cells can be unambiguously distinguished by their genomic phenotype from normal EpCAM-positive cells in the bone marrow. This is of particular importance since EpCAM-expression is insufficient proof for the (malignant) identity of tumor cell(s) in bone marrow samples. It has to be noted that healthy donors also showed 0.5–5% "3 3B1O-C9-positive cells (3B10-C9, Prof. Judy Johnson, Institute for Immunology, Munich) is a high affinity mAb against EPCAM) when determined by immunofluorescence.

EXAMPLE IV

Activity-related Gene Expression in Three Micrometastatic Cells

Single tumor cells were isolated from three patients with different tumors and disease stages. The first patient (C) had a 10-year history of cervical carcinoma and presented with a suspicious finding on chest x-ray. In the second patient (L), an adenocarcinoma of the lung had recently been diagnosed which was post-operatively staged as pT2, N3, M0. The bone marrow sample was obtained during the anesthesia prior to the operation. The third sample was aspirated from the pelvic crest of a 31-year old breast cancer patient (B) whose disease was in the stage pT1a, pN1a (1/18), M0. Because of a local relapse, the histological G3 grading, and finding of one cytokeratin-positive cell in the bone marrow, this patient received high-dose chemotherapy (HD). The bone marrow sample was taken one month after completion of HD. SCOMP was performed with all three cells and showed multiple chromosomal aberrations verifying the cancerous origin of cells (Tab. 4).

TABLE 4

Genomic aberrations of 3B10-C9-positive cells isolated from bone marrow of a three patients with cervical carcinoma (C), lung cancer (L) and breast cancer (B).

| Cell | 1p | 1q | 2p | 2q | 3p | 3q | 4p | 4q | 5p |
|---|---|---|---|---|---|---|---|---|---|
| C |  | G |  |  |  | G |  |  |  |
| L | L | G |  |  | L |  |  | L | G |
| B |  |  |  | G |  |  |  | G |  |

| Cell | 5q | 6p | 6q | 7p | 7q | 8p | 8q | 9p | 9q |
|---|---|---|---|---|---|---|---|---|---|
| C | G/L |  |  |  |  |  |  |  | L |
| L | L | G | G | G | G | L | G | L |  |
| B |  |  |  |  |  |  |  | L | L |

| Cell | 10p | 10q | 11p | 11q | 12p | 12q | 13p | 14q | 15q |
|---|---|---|---|---|---|---|---|---|---|
| C | G |  |  |  |  | L |  | L |  |
| L | L |  | L | G |  |  | L |  | L |
| B |  |  | L | L | G | G |  | G |  |

| Cell | 16p | 16q | 17p | 17q | 18p | 18q | 19p | 19q | 20p |
|---|---|---|---|---|---|---|---|---|---|
| C |  | L |  |  | G |  |  |  | L |
| L | L | G | L | L |  |  |  |  |  |
| B |  |  |  |  |  |  |  |  |  |

| Cell | 20q | 21p | 21q | 22p | 22q | Xp | Xq | Y |
|---|---|---|---|---|---|---|---|---|
| C | L |  |  |  | L |  |  |  |
| L |  |  | G |  |  | G | G |  |
| B |  |  |  |  |  | G | G |  |

Summary of the CGH-data obtained from the three micrometastatic cells. Losses (L) and gains (G) on the small (p) and long (q) arm of each chromosome are given for each cell.

Figure 4:
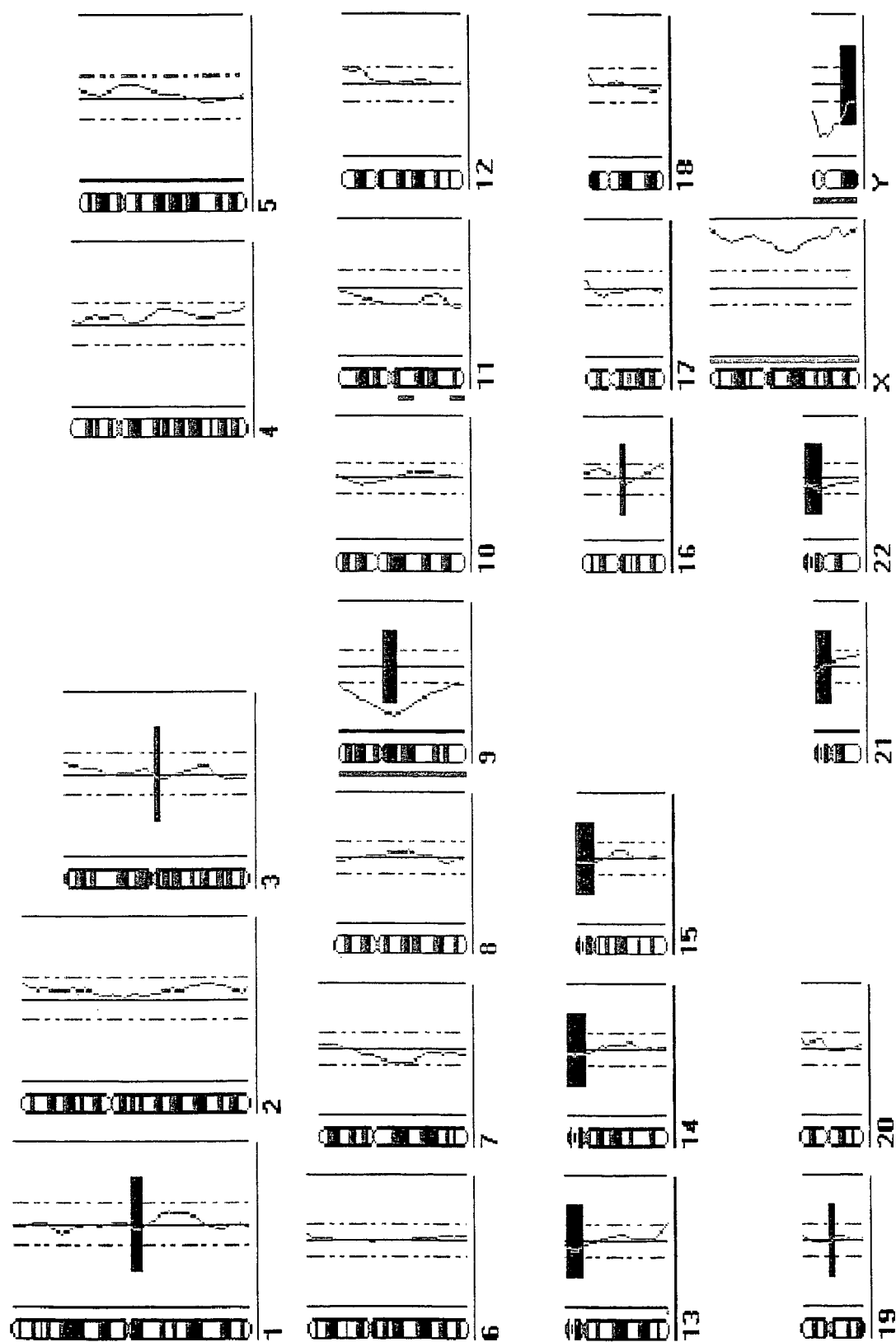
FIG. 4. CGH profile of cell B derived from a breast cancer patient with very small primary tumor (stage T1a). Chromosomal deletions are marked with a red bar left of and chromosomal gains with a green bar right of the chromosome symbol.

The cell from patient B, who had the least advanced disease, showed the lowest extent of chromosomal changes (FIG. 4).

mRNA was isolated from all three cells and samples generated for SCAGE as described above. As control, the procedure was performed without the addition of a cell. cDNA amplificates were hybridized to Clontech Cancer 1.2 filters and to newly generated arrays (Axxima A6, Martinsreid) comprising a total of 1,300 genes.

Non-radioactiv hybridization to nylon filters was carried out as follows:

15 ng of the different PCR-amplified and subcloned cDNA fragments were spotted on positively charged nylon filters by Axxima A G, Martinsried. Filters were pre-hybridized overnight in the presence of 50 µg/ml E. coli and 50 µg/ml pBS DNA in 6 ml Dig-easy Hyb buffer (Roche Biochemicals). 9 µg of labeled PCR products from single cells were mixed with 100 µg herring sperm, 300 µg E. coli genomic DNA and 300 µg, denatured for 5 min at 94° C., added to 6 ml Dig-easy hybridization buffer and hybridized for 36 hours. Stringency washes were performed according to the Roche digoxigenin hybridization protocol adding two final stringency washes in 0.1×SSC+0.1% SDS for 15 min at 68° C. Detection of filter bound probes was performed according to the Digoxigenin detection system protocol supplied with the kit (Roche).

Only three genes had to be excluded from analysis because a signal was obtained in at least one of the negative controls. These genes were the VHL-binding protein, caspase 10, TGF-β and hemoglobin α. The number of positive signals ranged from 5.3% (70/1313), 7.0% (92/

Figure 5:
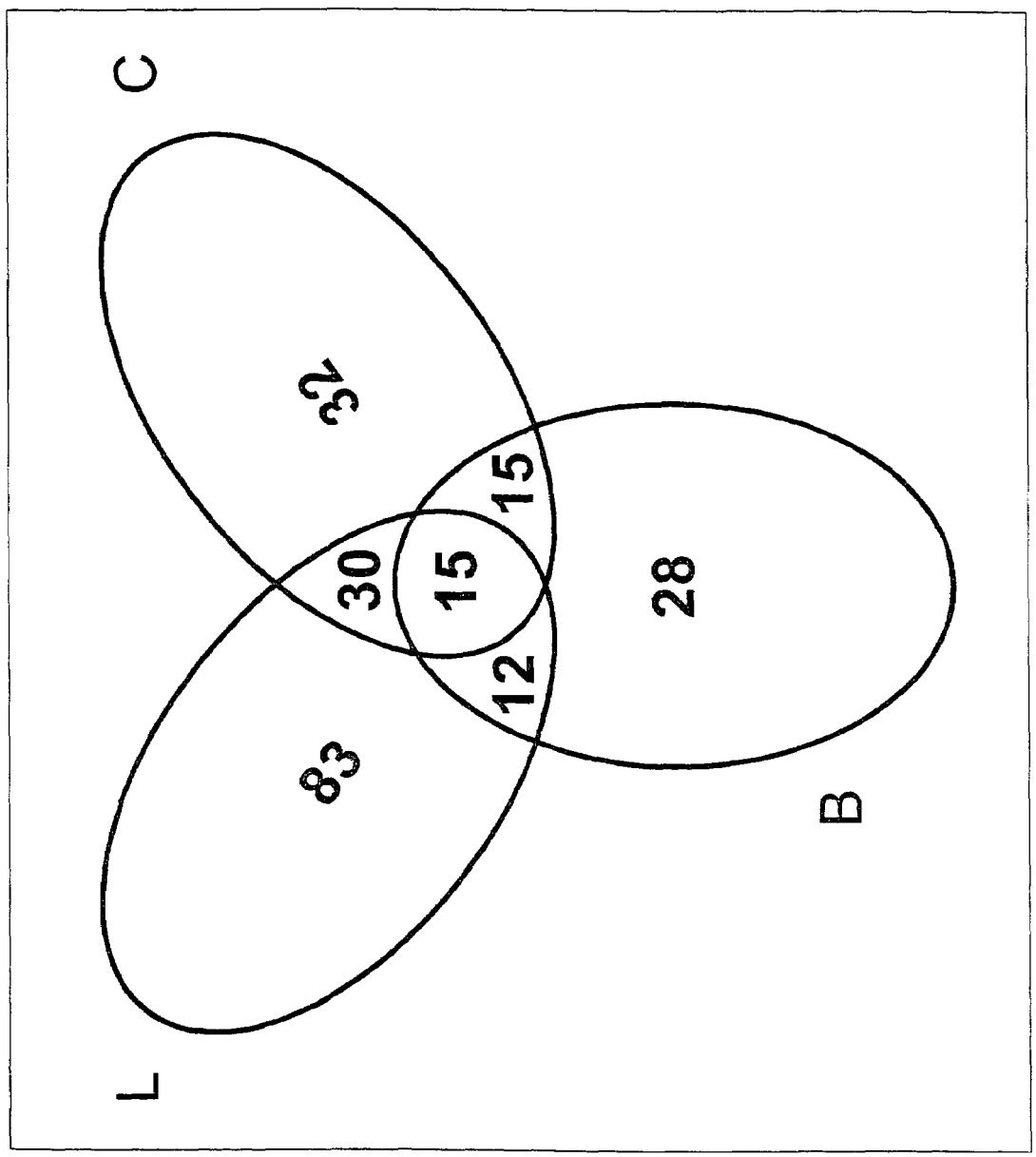
FIG. 5. Diagram illustrating the common and differentially expressed genes of cell B, C and L.

1313) to 11.8% (155/1313) for cells from patients B, C, and L respectively. These numbers were considerably lower than those from single in vitro-grown carcinoma cells where signals were obtained with 10–20% of genes (data not shown). All three tumor cells expressed genes known to play a role in regulation of proliferation, replication or growth arrest (FIG. 5; Tab. 5).

TABLE 5

Upregulated genes implied in cell cycle status in cells C, L and B.

| Role in cell cycle | C | B | L |
|---|---|---|---|
| Positive regulators | RFC3 | RFC3 | RFC3 |
| | LIG1 | LIG1 | |
| | STK12 | STK12 | |
| | P2G4 | P2G4 | |
| | RFC2 | RFC2 | |
| | ADPRT | ADPRT | |
| | S100A4 | S100A4 | |
| | CCNA (cyclin A) | CDC25 | |
| | MKI67 (Ki-67) | VRK2 | |
| | CENPF | DYRK4 | |
| | D123 | PRIM1 | |
| | PIN1 | PRKDC (DNA-PK) | |
| | EB1 | CHD3 | |
| | CDC27HS | | |
| | CALM1 | | |
| | UBL1 | | |
| | TOP2A | | |
| | HMGIY | | |
| | HDAC3 | | |
| | RBBP4 | | |
| Negative regulators | | CDKN1A (P21) | CDKN1A (P21) |
| | | ING1 | ING1 |
| | | DDIT1 (GADD45) | CDKN2A (P16) |

Cells C and B expressed several positive regulators of the cell cycle, while only B and L expressed cell cycle inhibitors.

Cell C expressed the highest number of genes important for cell cycle progression, including cyclin A (CCNA), EB1, RC2, P2G4, PIN1, RBBP4 and CENPF. As most of these genes are tightly transcriptionally regulated and their mRNAs are rapidly degraded as cell division progresses, their expression not only indicates that cell C was engaged in cycling but can be faithfully captured in this activity by SCAGE.

Cell B expressed a number of genes important for replication as well as cell cycle inhibition. The pattern of transcripts suggests that the cell was in a state of DNA repair. The coexpression of GADD45 (DDIT1) and p21 (CDKN1A) are indicative for growth arrest (Smith, Science, 266, 1376–1380 (1994)). Likewise, the expression of positive cell cycle regulators such as DNA-PK, RFC2, LIG1, ADPRT and PRIM1 has been implicated in DNA repair (Lindahl, Science, 286, 1897–1905 (1999); Barnes, Cell, 69, 495–503 (1992), Mossi, Eur. J. Biochem., 254, 209–216 (1998); Lee, Mol. Cell Biol. 17, 1425–1433 (1997)). As this cell survived an alkalyting, genotoxic high dose chemotherapy its expression profile may be interpreted as if re-entry into cell cycle was obviated. This interpretation is supported by the expression of pro-apoptotic genes such as caspase-6 and BAD that were only found with this cell. Execution of apoptosis in this cell may however be counteracted by expression of survivin (API4) (FIG. 5; Tab. 5).

Figure 6:
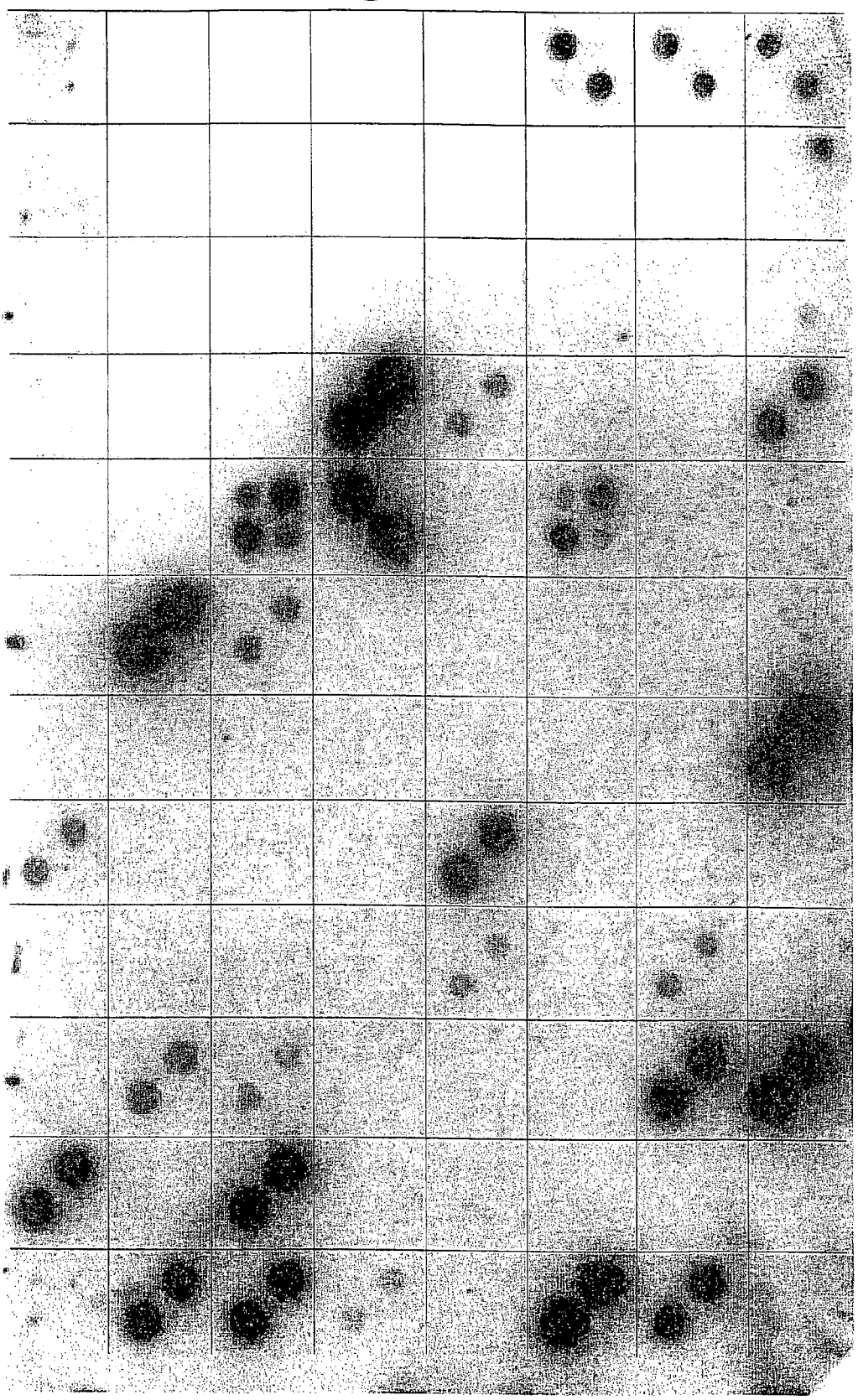
FIG. 6. Hybridisation of cell L (left) and the matrix of positions and names of immobilized cDNAs. Genes were spotted in duplicates in diagonal direction, with the blue gene symbols oriented from upper left to lower right and the red gene symbols oriented from upper right to lower left.

The transcriptome obtained from cell L showed traits compatible with its engagement in dissemination and EMT. While gene expression of cell L did not resemble that of a cycling or DNA-repairing cell (see above) its 84 differentially expressed genes are mostly involved in cytoskeletal reorganization, cell adhesion and extracellular proteolytic activity (Tab. 6; FIG. 6).

TABLE 6

Upregulated genes in cell L indicative for an Invasive phenotype.

| cytoskeletal organization | Adhesion | proteolytic activity |
|---|---|---|
| Cytokeratin 2 | Integrin alpha 3 | Cathepsin B |
| Cytokeratin 6 | Integrin alpha v | Cathepsin D |
| Cytokeratin 7 | Integrin beta 2 | Cathepsin L |
| Cytokeratin 8 | Integrin beta 3 | MMP7 |
| Cytokeratin 10 | Integrin beta 7 | MT1-MMP |
| Cytokeratin 13, 15, 17 | | MT2-MMP |
| Cytokeratin 18 | Cytohesin 1 | uPA |
| Cytokeratin 19 | Focal adhesion kinase | uPA-R |
| Vimentin | Desmoglein 2 | ADAM 8 |
| Beta-actin | E-cadherin | ADAM 15 |
| | CD9 | ADAM 17 |
| RhoA | | Bikunin |
| RhoB | | |
| Rho-GDI2 | | Cystatin 2 |
| A-raf | | EMMPRIN |
| RAP-1A | | |
| Cdc42 | | |
| Rac1 | | |
| P160 ROCK | | |
| Ste20-like kinase | | |
| Beta-catenin | | |

The present study analyzed for the first time cellular activities of individual tumor cells derived from the bone marrow of cancer patients. Cell C was derived from a cervical carcinoma patient who presented with lung metastasis after a ten-year latent period. This cell was found in proliferation. Cell B was from bone marrow of a breast cancer patient with a rather small primary cancer who had received high dose chemotherapy because of the apparent aggressiveness of her tumor. This cell showed relatively few and discrete genomic changes, a finding that is of particular interest with regard to the genomic changes required for dissemination. Moreover, this cell must have survived four cycles of a regular chemotherapy consisting of Epirubicin and Taxol in addition to a high-dose chemotherapy regimen involving alkylating agents. The obtained expression profile is diagnostic for growth arrest and ongoing DNA repair.

Most informative with respect to the process of dissemination was the transcriptome of cell L. Detected in a bronchial cancer patient without clinically manifest metastasis, this cell expressed many genes encoding proteins involved in active migration and invasion. Most of the activation cascade of the uPA system was found expressed, consisting of the cathepsin B, D, L, the uPA receptor and uPA itself. Likewise, genes involved in organizing filopodia, lamellipodia and stress fibers, the Rho family members RhoA and B, Rac1, Cdc42 and p160 rock, and genes encoding several adhesion molecules were upregulated in this cell. Its cytoskeleton seemed to undergo remodeling as shown by expression of many cytokeratins and vimentin, a marker for EMT.

It is noteworthy that the number of transcripts in single cells isolated from cultured cell lines was considerably lower than that from patient-derived tumor cells. This difference may speak for a tighter in vivo control of transcription that may become more relaxed when cells are grown in cell culture, e.g., by increased DNA demethylation. Expression analysis of ex-vivo specimen might therefore be much more informative than studies on cell lines. The minimal number of cells that has been used for cDNA array analysis so far was in the range of 1,000 cells (Luo (1999), loc. cit.). The sensitivity of the array hybridization might be further increased by longer immobilized cDNA fragments (fragment length on Clontech arrays is about 200 bp), and the amount of information obtained by using glass chips with higher density and complexity. Although the present study analyzed only 1,300 genes, one has to consider that expression of only nine proteins has thus far been reported for micrometastatic cells. These proteins are ErbB2, transferrin receptor, MHC class I, EpCAM, ICAM-1, plakoglobin, Ki-67, p120 and uPA-receptor/CD87 (Pantel, J. Natl. Canc. Inst. 91, 1113–1124 (1999)).

The here described method has potential for the study of gene expression by rare cells in many other fields (as shown hereinbelow; for example, in the investigation of human restenotic tissue). For instance, the investigation of spatially and temporally regulated gene expression in embryogenesis and the analysis of stem cells and differentiated cells in adult tissues could be performed. Single cell analysis would greatly advance the understanding of a typical proliferation, metaplasia, pre-neoplastic lesions and carcinomata in situ.

A synopsis of genomic aberrations and the expression profiles of the same cell may reveal the contingencies of different genotypes and phenotypes within a tumor cell population.

High-dose chemotherapy, surgery, and anti-angiogenic therapy approaches can target rapidly dividing cells and large tumor masses but are ineffective in the elimination of remnant cells leading to minimal residual disease. Adjuvant therapies, like antibody-based approaches Riethmuller, J. Clin. Oncol., 16, 1788–1794 (1998), are still based on protein targets identified on the primary tumor. The here shown approach provides now an opportunity to discover targets for minimal residual disease by analyzing the micrometastatic cells directly.

EXAMPLE V

Aberrant Gene Expression in Human Restenotic Tissue

The above described method was furthermore employed to detect differentially expressed genes in human restenotic tissue.

A high rate of restenosis is significantly limiting the success of percutaneous transluminal coronary angioplasty with subsequent stent implantation as a frequent treatment of coronary atherosclerotic disease. Although several cellular and molecular mechanisms have been identified in the development of in-stent restenosis, specific targets for an effective therapeutic prevention of restenosis are still scarce. In this study differentially expressed genes in microscopic atherectomy specimen from human in-stent restenosis were identified. Immunohistochemistry showed that the restenotic material consisted mainly of smooth muscle cells (SMC) with rare infiltrates of mononuclear cells. cDNA samples prepared from restenotic specimen (n=10) and, as control, from intima and media of healthy muscular arteries (n=10) were amplified using a novel polymerase chain reaction protocol and hybridized to cDNA arrays for the identification of differentially expressed genes. Expression of desmin and mammary-derived growth inhibitor was downregulated, whereas expression of FK506-binding protein 12 (FKBP12), thrombospondin-1, prostaglandin G/H synthase-1, and the 70-kDa heat shock protein B was found to be upregulated with high statistical significance in human neointima. Using immunohistochemistry, FKBP12, a negative regulator of TGF-β signaling, was also upregulated at the protein level in neointima providing a rationale for the therapeutic effect of the FKBP12 ligand rapamycin in the treatment of a porcine restenosis model.

To gain further insight into transcriptional and signaling events governing smooth muscle cell migration, proliferation and synthesis of extracellular matrix, differential gene expression screening was employed using cDNA array technology with probes generated from microscopic specimen of human restenotic tissue. The power of this technology is the ability to simultaneously study in one sample the expression of thousands of genes (Kurian, (1999) *J Pathol* 187:267–271). A previous hurdle of using this method was the need for micrograms of mRNA or cRNA from samples usually composed of $10^6$–$10^7$ cells. Here, the novel technology, as described hereinabove, was employed. This allowed the generation of representative cDNA amplificates from a single cell or a low number of cells in quantities sufficient for comprehensive cDNA array hybridization.

10 specimen of each neointimal and quiescent media for the expression of 2,435 genes of known function. While the expression of house-keeping genes was largely comparable between normal and restenotic tissue close to 10 percent of studied genes showed an increased or decreased level of expression. In the present study, it was focused on selected genes that have previously been associated with restenosis. Desmin and mammary-derived growth factor inhibitor (MDGI) expression was selectively downregulated while the expression of prostaglandin G/H synthase-1 (COX-1), thrombospondin-1 (TSP-1), heat-shock protein-70 B (hsp70B) and FK506-binding protein 12 (FKBP12) was found to be upregulated in human neointima hyperplasia. These findings were all confirmed by gene-specific PCR. To study the significance of increased gene expression in neointima, it was investigated whether increased mRNA levels find their reflection in an increased protein level. As exemplified with FKBP12 using immunohistochemistry, it was indeed found a robust overexpression of this regulator of TGF-β signaling in restenotic tissue. This study shows that cDNA array technology can be used to reliably identify differentially expressed genes in healthy and diseased human tissue even if only very small amounts of material are available.

The in-stent restenosis study group consisted of 13 patients who underwent separate atherectomy procedures by Helix cutter device artherectomy (X-sizer, Endicor) within the renarrowed stent between 4–23 month after primary stent implantation. All patients gave informed consent to the procedure and received 15,000 units heparin before the intervention followed by intravenous heparin infusion, 1,000 units/h for the first 12 h after sheat removal as standard therapy. All patients received aspirin, 500 mg intravenously, before catherisation, and postinterventional antithrombotic therapy consisted of ticlopidine (250 mg bds) and aspirin (100 mg bds) throughout the study.

Sample Preparation was Carried Out as Follows:

Atherectomy specimen were immediately frozen in liquid nitrogen after debulking of the lesion, and kept in liquid nitrogen until mRNA preparation was performed as described. For histology and immunhistochemistry of the in-stent restenotic tissue from coronary arteries (n=3), the samples were fixed in 4% paraformaldehyd and embedded in paraffin as described.

The control group consisted of 5 specimen of muscular arteries of the gastrointestinal tract from five different patients and 5 specimen from coronary arteries from three different patients who underwent heart transplantation. The control specimen were immediately frozen in liquid nitrogen. Prior to mRNA preparation, media and intima of the control arteries were prepared and examined for atherosclerotic changes by immunhistochemistry. If there were no atherosclerotic changes of the vessel morphology, the specimen (approx. 1×1 mm) were used as healthy control samples and mRNA and cDNA preparation was performed as described.

For immunohistochemistry of FKBP12, neointima specimen of carotid restenotic arteries (n=2) were obtained by atherectomy and immediately frozen in liquid nitrogen after removal. Three 3 μm serial frozen sections of the samples were mounted onto DAKO ChemMate™ Capillary Gap Microscope slides (100 μm).

mRNA Preparation and amplified cDNA was carried out as follows:

Specimen of quiescent vessels or in-stent restenotic tissue were quick-frozen and kept in liquid nitrogen until mRNA preparation and cDNA synthesis was performed. Frozen tissue was ground in liquid nitrogen and the frozen powder dissolved in Lysis/Binding buffer (100 mM Tris-HCl, pH 7.5, 500 mM LiCl, 10 mM EDTA, pH 8.0, 1% LiDS, 5 mM dithiothreitol (DTT)) and homogenized until complete lysis was obtained. The lysate was centrifuged for 5 mm at 10,000 g at 4° to remove cell debris. mRNA was prepared using the Dynbeads® mRNA Direct Kit™ (Dynal, Germany) following the manufacture's recommendation. Briefly, lysate was added to 50 μL of pre-washed Dynabeads Oligo $(dT)_{25}$ per sample and mRNA was annealed by rotating on a mixer for 30 min at 4° C. Supernatant was removed and Dynabeads Oligo $(dT)_{25}$/mRNA complex was washed twice with washing buffer containing Igepal (50 mM Tris-HCl, pH 8.0, 75 mM KCl, 10 mM DTT, 025% Igepal), and once with washing buffer containing Tween-20 (50 mM Tris-HCl, pH 8.0, 75 mM KCl, 10 mM DTT, 0.5% Tween-20).

cDNA was amplified by PCR using the procedure as described hereinabove. First-strand cDNA synthesis was performed as solid-phase cDNA synthesis. Random priming with hexanucleotide primers was used for reverse transcription reaction. mRNAs were each reversely transcribed in a 20 μL reaction volume containing 1× First Strand Buffer (Gibco), 0.01 M DTT (Gibco), 0.25% Igepal, 50 μM CFL5c-Primer (SEQ ID NO:8) [5'-$(CCC)_5$ GTC TAG A $(NNN)_2$-3'], 0.5 mM dNTPs each (MBI Fermentas) and 200 U Superscript II (Gibco), and incubated at 44° C. for 45 mm. A subsequent tailing reaction was performed in a reaction volume of 10 μL containing 4 mM $MgCl_2$, 0.1 mM DTT, 0.2 mM dGTP, 10 mM $KH_{12}PO_{14}$ and 10 U of terminal deoxynucleotide transferase (MBI Fermentas). The mixture was incubated for 24 mm at 37° C.

cDNA was amplified by PCR in a reaction volume of 50 μL containing 1× buffer 1 (Expand™ Long Template PCR Kit, Boehringer Mannheim), 3% deionized formamide, 1,2 μM CP2-Primer (SEQ ID NO:14) [5'-TCA GAA TTC ATG $(CCC)_5$-3'], 350 μM dNTP and 4.5 U DNA-Polymerase-Mix (Expand™ Long Template PCR Kit, Roche Diagnostics, Mannhein). PCR reaction was performed for 20 cycles with the following cycle parameters: 94° C. for 15 sec, 65° C. for 0:30 mm 68° C. for 2 mm; for another 20 cycles with: 94° C. for 15 sec, 65° C. for 30 sec, 68° C. for 2:30+0:10/cycle mm; 68° C. 7 mm; 4° C. forever.

25 ng of each cDNA was labeled with Digoxigenin-11-dUTP (Dig-dUTP) (Roche Diagnostics) during PCR. PCR was performed in a 50 μL reaction with 1× Puffer 1, 120 μM CP2 primer, 3% deionized formamide, 300 μM dTTP, 350 μM dATP, 350 μM dGTP, 350 μM dCTP, 50 μM Dig-dUTP, 4.5 U DNA-Polymerase-Mix. Cycle parameters were: one cycle: 94° C. for 2 mm; 15 cycles: 94° C. for 15 sec, 63° C. for 15 sec, 68° C. for 2 mm; 10 cycles: 94° C. for 15 sec, 68° C. for 3 min+5 sec/cycle; one cycle: 68° C., 7 min, 4° C. forever.

Hybridization of Clontech cDNA Arrays with dUTP-labeled cDNA Probes was carried out as follows:

cDNA arrays were prehybridized in DigEASYHyb solution (Roche Diagnostics) containing 50 mg/L DNAseI (Roche Diagnostics) digested genomic E. coli DNA, 50 mg/L pBluescript plasmid DNA and 15 mg/L herring sperm DNA (Life Technologies) for 12 h at 44° C. to reduce background by blocking non-specific nucleic acid-binding sites on the membrane. Hybridization solution was hybridized to commercially available cDNA arrays with selected genes relevant for cancer, cardiovascular and stress response (Clontech). Each cDNA template was denatured and added to the prehybridization solution at a concentration of 5 μg/ml Dig-dUTP-labeled cDNA. Hybridization was performed for 48 hours at 44° C.

Blots were subsequently rinsed once in 2×SSC/0.1% SDS and once in 1×SSC/0.1% SDS at 68° C. followed by washing for 15 min once in 0.5×SSC/0.1% SDS and twice for 30 min in 0.1×SSC/0.1% SDS at 68° C. For detection of Dig-labeled cDNA hybridized to the array, the Dig Luminescent Detection Kit (Boehringer, Mannheim) was used as described in the user manual. For detection of the chemiluminescence signal, arrays were exposed to chemiluminescence films for 30 min at room temperature. Quantification of array data was performed by scanning of the films and analysis with array vision software (Imaging Research Inc., St. Catharines, Canada). Background was subtracted and signals were normalized to the nine housekeeping genes present on each filter, whereby the average of the housekeeping gene expression signals was set to 1 and the background set to 0. In a pilot study, six clones enriched in one of the two probes were further analyzed by RT-PCR.

Results of the experimental studies are reported as mean expression values of the ten examined specimen of the study or control group. Differences between the two patient groups were analyzed by Wilcoxon-test (SPSS version 8.0). A p-value less than 0.03 was regarded as significant.

A selection of differential hybridization signals were confirmed by PCR using gene-specific primers. PCR reactions were performed using 2.5 ng of each cDNA in 25 μl reaction containing 1×PCR buffer (Sigma), 200 μM dNTPs, 0.1 μM of each primer and 0.75 U Taq Polymerase (Sigma). The following primers were used: desmin, (SEQ ID NO: 17) 5'-ACG ATT CCC TGA TGA GGC AG-3' and (SEQ ID NO:18) 5'-CCA TCT TCA CGT TGA GCA GG-3'; thrombospondin-1, (SEQ ID NO:19) 5'-CTG AGA CGC CAT CTG TAG GCG GTG -3' and (SEQ ID NO:20) 5'-GTC TTT GGC TAC CAG TCC AGC AGC-5'; mammary-derived growth inhibitor, (SEQ ID NO:21) 5'-AAG AGA CCA CAC TTG TGC GG-3' and (SEQ ID NO:22) 5'-AAT GTG GTG CTG AGT CGA GG-5'; prostaglandin G/H synthase-1, (SEQ ID NO:23) 5'-CGG TGT CCA GTT CCA ATA CC-3' and (SEQ ID NO:24) 5'-CCC CAT AGT CCA CCA ACA TG-3'; FKBP12, (SEQ ID NO:25) 5'-ATG CCA CTC TCG TCT TCG AT-3' and (SEQ ID NO:26) 5'-GGA ACA TCA GGA AAA GCT CC-3'; heat shock protein 70B, (SEQ ID NO:27) 5'-TAC AAG GCT GAG GAT GAG GC-3' and (SEQ ID NO:28) 5'-CTT CCC GAC ACT TGT CTT GC-3', and β-actin, (SEQ ID NO:29) 5'-CTA CGT CGC CCT GGA CTT CGA GC-5' and (SEQ ID NO:30) 5'-GAT GGA GCC GCC GAT CCA CAC GG-3'. PCR products were subjected to electrophoresis on a 2% agarose gel containing ethidium bromide (0.5 µg/ml agarose solution) in TAE buffer (20 mM Tris/HCl, 10 mM acetic acid, 1 mM EDTA).

Immunohistochemistry was carried out as follows:

Immunohistochemistry for cell typing was performed on paraffin-embedded sections of three neointima specimen from coronary in-stent restenosis, and for detection of FKBP12, on frozen sections of four neointima specimen from carotid restenosis. Three µm serial sections were mounted onto DAKO ChemMate™ Capillary Gap Microscope slides (100 µm) baked at 65° C. overnight, deparaffinized and dehydrated according to standard protocols. For antigen retrieval, specimens were boiled 4 min in a pressure cooker in citrate buffer (10 mM, pH 6.0). Endogenous peroxidase was blocked by 1% $H_2O_2$/methanol for 15 minutes. Unspecific binding of the primary antibody was reduced by preincubation of the slides with 4% dried skim milk in Antibody Diluent (DAKO, Denmark). Immunostaining was performed by the streptavidin-peroxidase technique using the ChemMate Detection Kit HRP/Red Rabbit/Mouse (DAKO, Denmark) according to the manufacturer's description. The procedures were carried out in a DAKO TechMate™ 500 Plus automated staining system. Primary antibodies against smooth muscle actin (M0635, DAKO, Denmark; 1:300), CD3 (A0452, DAKO, Denmark; 1:80), MAC387 (E026, Camon, Germany; 1:20) and FKBP12 (SA-218, Biomol, Germany, 1:20) were diluted in Antibody Diluent and incubated for 1 h at room temperature. After nuclear counterstaining with hematoxylin, the slides were dehydrated and coverslipped with Pertex (Medite, Germany).

For FKBP12 immunhistochemistry, 3 µm frozen, serial sections of the neointima specimen from carotid restnosis were mounted onto DAKO ChemMate™ Capillary Gap Microscope slides (100 µm).

The following results were obtained:

(a) The Cellular Composition of Debulked In-stent Restenotic Material

Representative samples obtained from x-sizer treatment of a neointimal hyperplasia were analyzed by immunhistochemistry in order to determine its cellular composition. The restenotic tissue analyzed was removed by x-sizer debulking from coronary arteries more than two month after PTCA and stent implantation. The amount of tissue generated by this procedure was very low containing an estimated 300–10000 cells. FIG. 7A shows an E.-van-Giesson staining of a section cut from a small sample of debulked restenotic material. With this staining procedure, collagen fibers stain red, fibrin stains yellow and cytoplasm of smooth muscle cells stains dark-yellow-brown. The majority of the volume of debulked material was composed of loose extracellular matrix-like collagen fibers stained in light red. Yellow fibrin staining was barely detectable. Cells with spindle-shaped nuclei and a yellow/brown-stained cytoplasm were frequent. Their identity as smooth muscle cells and their high abundance in restenotic material was supported by immunostaining with an antibody against smooth muscle α-actin (FIG. 7B). There, the staining pattern of a section from an entire specimen as used for gene expression analysis is shown. As described below, such samples also gave raise to a strong smooth muscle-specific α-actin mRNA signal (see FIG. 8). These results support findings from previous studies (Komatsu, (1998), *Circulation* 98:224–233; Strauss (1992), *J. Am. Coll. Cardiol.* 20:1465–1473; Kearney (1997), *Circulation* 95:1998–2002) demonstrating that the main cell type found in neointima is derived from smooth muscle cells. As described in the literature, mononuclear infiltrates in some areas of debulked restenotic tissue specimen could also be identified (data not shown). These infiltrates consisted mainly of macrophages and to a lesser degree of t-lymphocytes. No b-lymphocytes were detectable in the restenotic tissue by using an antibody against CD20 for immunhistochemical staining (data not shown).

(b) Expression of Specific Genes in Microscopic Human Tissue Samples

Figure 8:
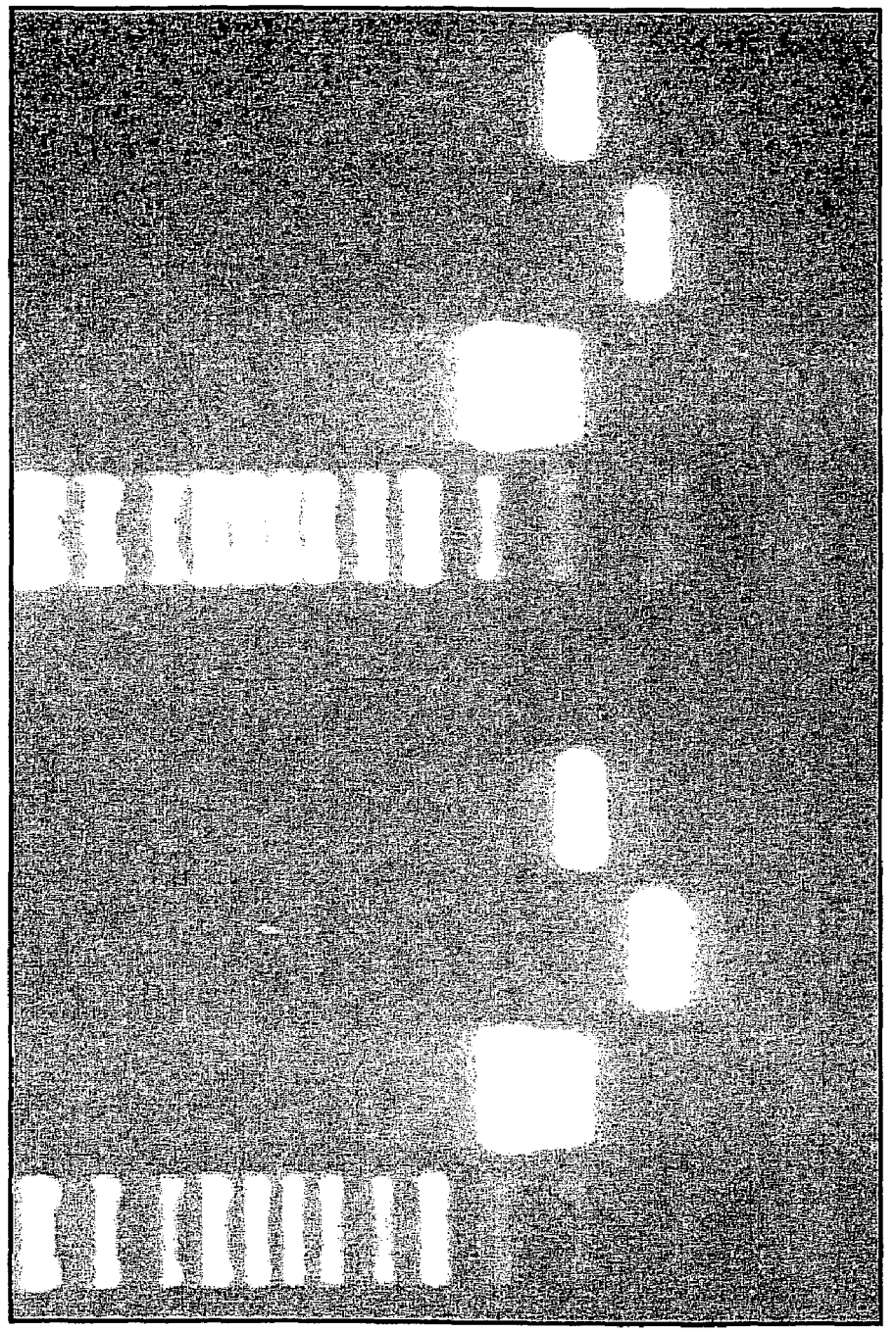
FIG. 8: PCR with gene-specific primer for β-actin (lanes 1), EF-α (lanes 2) and α-actin (lanes 3) as a control for successful PCR amplification of the first strand cDNA generated from microscopic tissue specimen. Shown is one representative from each study group (right panel: patient B; left panel: control donor b). The position of three size markers (M) is shown.

In order to optimally preserve the in situ mRNA levels, restenotic and control specimen were immediately frozen after harvest in liquid nitrogen and carefully lyzed as described hereinabove. After PCR amplification of the synthesized cDNA the amount of the amplified cDNA was measured by a dot blot assay and found to be between 200–300 ng/µl. The quality of every amplified cDNA sample was tested by gene-specific PCR using primers detecting cDNAs for β-actin, smooth muscle cell α-actin and the ubiquitous elongation factor EF-1α. FIG. 8 shows a representative result with material from patient B and control media from donor b. In both specimen, PCR signals of the correct size from house-keeping genes β-actin and EF-1α were detectable in equivalent amounts (compare lanes 1 and 2 with lanes 4 and 5). Additionally, α-actin signals as marker for smooth muscle cells was obtained from each specimen (lanes 3 and 6). These results show that mRNA preparation, cDNA synthesis and PCR amplification of cDNA is feasible with microscopic human restenosis samples.

(c) Comparative Gene Expression Profiling Using Microscopic Human Tissue Samples To identify differentially expressed mRNAs in restenotic versus healthy specimen, the cDNAs was labeled during PCR amplification with digoxigenin-labeled dUTP as described hereinabove. This label allows for a highly sensitive, chemiluminescence-based detection of hybridization signals of cDNA arrays on photographic films. The nylon filters with cDNA arrays were prehybridized with DNAseI-digested genomic *E. coli* DNA and with DNAseI-digested pBluescript plasmid DNA. This procedure was employed to maximally reduce non-specific DNA binding to the array. Each labeled probe was hybridized to three different commercial cDNA arrays which allowed for the expression analysis of a total of 2,435 known genes. FIG. 9 shows a representative hybridization pattern obtained with one array using probes prepared from restenotic tissue of patient B (panel A) and media of donor b (panel B). Consistent with the gene-specific analysis shown in FIG. 8, comparable hybridization signals were obtained with the positive control of human genomic cDNA spotted on the right and bottom lanes of the array and with cDNA spots of various housekeeping genes (see for instance, spots D). If a biological specimen was omitted from cDNA synthesis and PCR amplification reactions almost no hybridization signals were obtained (FIG. 9, panel C), showing that hybridization signals were almost exclusively derived from added samples and not from DNA contaminations in reagents or materials used.

Figure 10:
FIG. 10: Transcription profiles of microscopic samples from human in-stent neointima and control vessels. Each column represents a gene expression analysis of a single specimen for 53 selected genes. An arrow indicated genes that show significant up- or downregulation in neointima versus control. Eight highly expressed housekeeping genes are shown on the bottom. One grey value corresponds to a signal intensity as shown at the bottom of the figure.
Figure 10:

Visual inspection of the hybridization patterns readily identified a number of signals that are different between healthy and diseased tissue (for instance signals A, B and C in FIGS. 9A and B). Samples from restenotic tissues consistently gave more signals than control tissues. Hybridization signals obtained from the use of three different cDNA arrays with 10 restenosis patient samples and 10 normal media samples were quantitated by densitometric analysis of photographic films and the data electronically compiled and further analyzed for statistics. Expression levels for 53 out of 2,435 genes is shown in FIG. 10 whereby one grey value corresponds to the signal intensity as shown in the figure legend. A considerable variation of gene expression is evident for most genes shown which may reflect genetic and physiological differences of patients and donors. For further analysis and verification by gene-specific PCR, only genes were considered that showed a differential expression with a statistical difference of at least p=0.03 by the Wilcoxon Test. Six such genes are highlighted in the list (FIG. 10). A total of 224 genes out of 2435 known genes was found to be differentially regulated in neointima with high statistical significance. Their comprehensive in-depth analysis will be published elsewhere. Indicative for a comparable sample quality, eight housekeeping genes showed very similar hybridization signal intensities with all 20 samples (FIG. 10, bottom).

(d) Validation of cDNA Array Data by Gene-specific PCR

Out of the list depicted in FIG. 10, six differentially regulated genes and one housekeeping gene were selected for validation of hybridization signals through PCR using gene-specific primers. All PCR signals obtained had the predicted size. In support of an equal quality of samples, the β-actin signal (bottom) showed a very similar intensity with all 20 samples. By comparing gene-specific PCR signals (FIG. 11) with hybridization signals obtained from cDNA arrays (FIG. 11) it was found that 135 out of 140 signals matched with respect to intensity. This corresponds to a 96% fidelity of hybridization signals from cDNA arrays showing that the here employed gene expression profiling approach is comparable with respect to quality and sensitivity to gene-specific PCR.

(e) Aberrant Gene Expression in Human Restenotic Tissue

Figure 11:
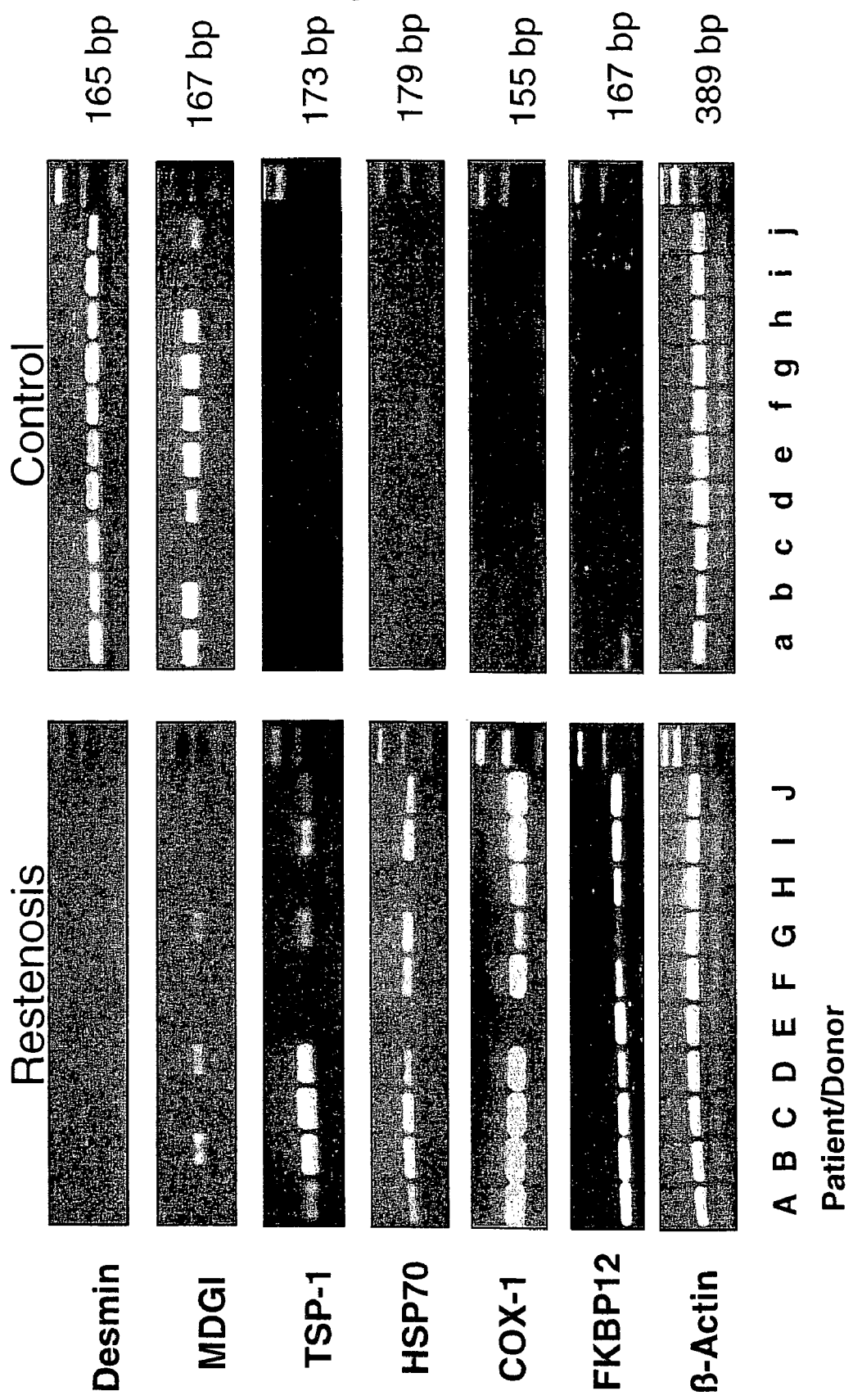
FIG. 11: Verification of differentially expressed mRNAs from cDNA arrays by gene-specific PCR. The size of the expected PCR fragment is indicated on the right.

Desmin, a mesenchymal marker, was found strongly expressed in the control media, whereas only weak signals were found in the restenotic specimen (FIGS. 10 and 11). Desmin is a marker for SMCs that is highly expressed in quiescent, differentiated SMCs. Its expression is reduced in de-differentiated, proliferating SMCs, e.g., in SMCs of atherosclerotic plaques (Ueda (1991), *Circulation* 83:1327–1332). Downregulation of desmin in restenotic tissue implies that the spindle-shaped cells in the restenotic material are de-differentiated, proliferating SMCs. Inversely, TSP-1, an extracellular matrix protein, that is important in TGF-β activation and SMC migration and proliferation (Yehualaeshet (1999), *Am J Pathol* 155:841–851; Scott (1988), *Biochem. Biophys. Res. Commun.* 150:278–286), is markedly upregulated in the majority of neointimal specimen versus the control samples. The COX-1, stress-induced hsp70B and the ubiquitously expressed FKBP12 genes were significantly upregulated in almost all neointimal hyperplasia and barely, if at all, expressed in control specimen (FIGS. 10 and 11). The tumor suppressor MDGI was strongly expressed in quiescent smooth muscle whereas little expression was found in a few neointima hyperplasia samples. None of the restenotic lesions expressed desmin (0/0) compared to 100% of controls (10/10), only 30% (3/10) of the neointimal specimen expressed MDGI very slightly, whereas it was highly expressed in 8/10 (80%) of the controls. Otherwise, TSP-1 (7/10), COX-1 (9/10), hsp70B (8/10) and FKBP12 (10/10) were significantly upregulated in neointimal versus control specimen (TSP-1 [0/10], hsp70B [0/10], COX-1 [0/10], FKBP12 [1/10]).

(f) FKBP12 Protein Expression is Upregulated in Human Restenotic Tissue

Figure 12:
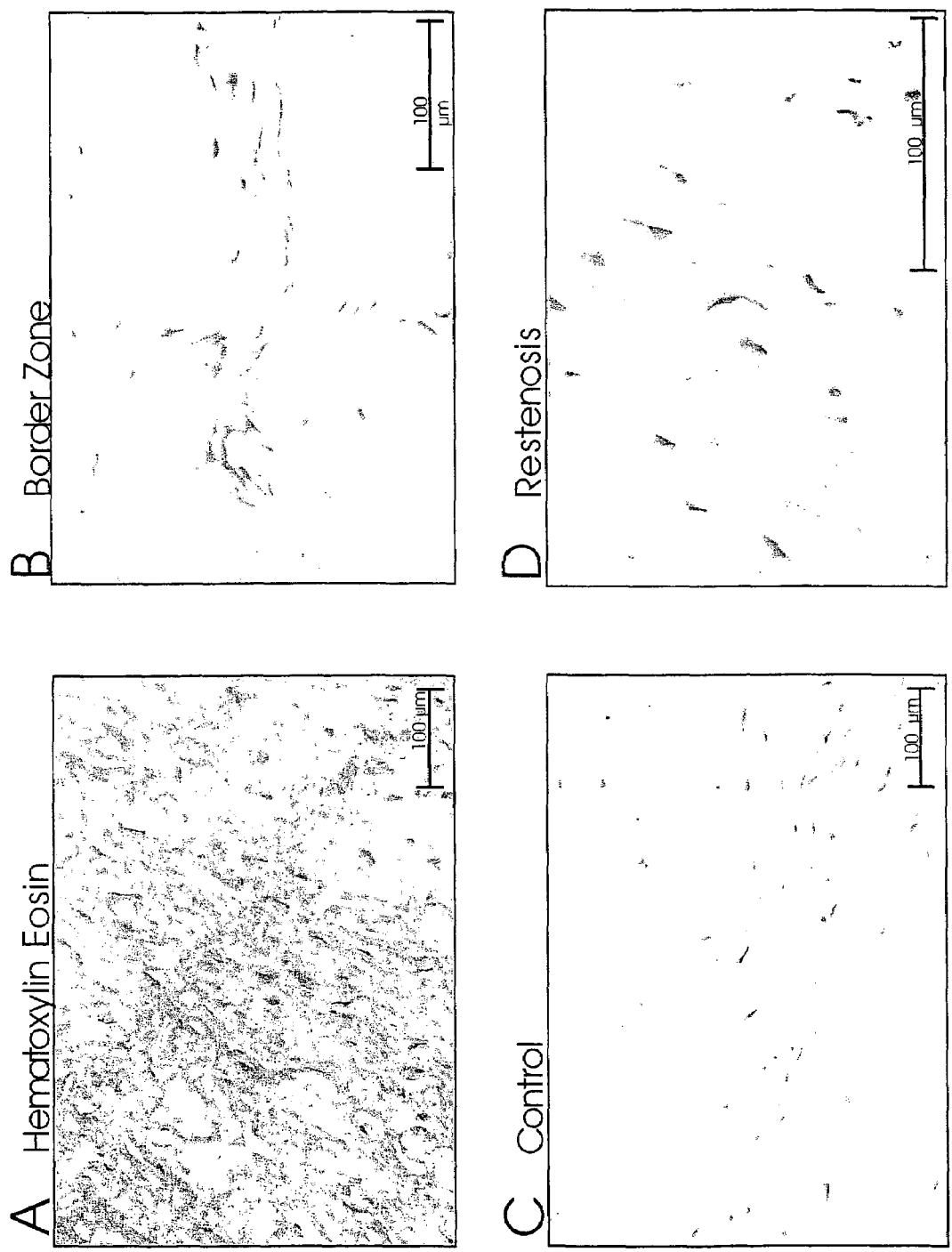
FIG. 12: Immunhistochemical staining of neointima from carotid artery restenosis for the FKBP12 protein. The experiment shown is a representative of three independent experiments. The bars represents a distance of 100 µm. Panel A shows a hematoxylin eosin staining, panel B–D shows staining for FKBP12 of the border zone between healthy media and neointima (panel B), of healthy control media (panel C) and neointimal tissue (panel D).

Upregulation of mRNA levels does not stringently indicate an increased level of protein. Among the genes that were found to be upregulated in human neointima, FKBP12 is particularly interesting since it is a regulator of TGF-β signaling and target for the drugs FK506 and rapamycin. A therapeutic effect of rapamycin in rodent models (Gallo (1999), Circulation 99:2164–2170) of restenosis is poorly understood but may be related to changes in the expression level of FKBP12. Using an antibody specific for FKBP12, human restenotic tissue from carotid restenosis (n=3) was analyzed and control tissue (n=3) for the expression of the protein. As shown in FIG. 12, an increase in FKBP12 protein in the cytoplasm of SMCs from restenotic lesions as identified by their spindle-shaped nuclei was detected (FIGS. 12B and D). Whereas no FKBP12 was detectable in control SMCs of healthy media (FIG. 12C), a distinct staining in SMCs of neointima was found (FIG. 12D). Interestingly, especially smooth muscle cells lying in the border zone between neointima and healthy media of restenotic vessels expressed high levels of the FKBP12 protein (FIG. 11B).

EXAMPLE VI

Characterization of the Transcriptome of Human Restenotic Tissue

The expression of 2,435 genes of known function (see Example V) was investigated in atherectomy specimen of 10 patients with in-stent restenosis, blood cells of 10 patients, normal coronary artery specimen of 11 donors, and cultured human coronary artery smooth muscle cells. 224 genes that were differentially expressed with high statistical significance (p<0.03) between neointima and control tissue which could be grouped as follows: (1) genes only expressed in neointima; (2) genes expressed in both neointima and proliferating smooth muscle cells; (3) genes expressed in both neointima and blood samples; and (4) genes expressed in control tissue but barely in neointima. The transcriptome of human neointima showed significant changes related to proliferation, apoptosis, inflammation, cytoskeletal reorganization and tissue remodeling. Furthermore, in neointima 32 upregulated genes were identified that are related to interferon-γ signaling.

In the present study, 10 specimen of neointimal and 11 specimen of quiescent intima/media for the expression of 2,435 human genes of known function were analyzed. While the expression of housekeeping genes was largely comparable between normal and restenotic tissue, an impressive number of genes (n=224) showed an increased or decreased level of expression. The gene expression pattern in neointima showed the anticipated proliferative response with induction of genes mainly expressed in G1/S phase, changes of the smooth muscle phenotype from contractile to synthetic SMCs and changes in synthesis of extracellular matrix proteins. Additionally, a pro-inflammatory expression pattern characterized by the presence of markers for macrophages and T lymphocytes and by the expression of numerous genes with known functions in the cellular response to IFN-γ were observed. The IRF-1 protein, a pivotal transcription factor in IFN-γ signaling, was found overexpressed in SMCs of human neointima.

The clinical characteristics of the patients of the study group of this Example are presented in Table 7.

Cell Culture was carried out as follows:

Primary human coronary artery smooth muscle cells (CASMCs) were obtained from CellSystems (St. Kathrinen, Germany) and were grown in Smooth Muscle Cell Growth Medium (CellSystems, St. Kathrinen, Germany) containing 5% fetal calf serum (CellSystems, St. Kathrinen, Germany) at 37° C. in a humidified atmosphere of 5% $CO_2$. CASMCs were used in experiments between passages 2 and 4. For cDNA synthesis of proliferating CASMCs were washed three times with ice-cold phosphate-buffered saline and

TABLE 7

Clinical Data of 13 Patients

| Patient | Age, y | Sex | Indication for Stent | Stent Site | Interval/ Stent/ Poststent Restenosis | Interval Stent/ Debulking | Smoker | Hyper- cholester- olemia | Arterial Hyper- tension | Diabetes mellitus | Multivessel disease | familial risk |
|---|---|---|---|---|---|---|---|---|---|---|---|---|
| 1 | 77 | m | AMI | RCA | 5 m | 11 m | − | + | + | + | + | − |
| 2 | 62 | m | SAP | LAD | 6 m | 19 m | − | + | + | − | − | + |
| 3 | 57 | m | ISAP | ACVB 7 | 4 m | 10 m | + | − | + | + | + | − |
| 4 | 68 | m | failed Bypass | ACVB 14 | 4 m | 4 m | − | + | + | − | + | − |
| 5 | 80 | m | AMI | LAD | 7 m | 7 m | − | + | + | − | + | − |
| 6 | 67 | m | Restenosis | RCA | 12 m | 23 m | − | + | + | − | + | − |
| 7 | 44 | f | Restenosis after PTCA | RCA | 3 m | 8 m | − | + | 7 | − | − | − |
| 8 | 75 | m | Restenosis after PTCA | RCA | 6 m | 6 m | − | + | − | − | + | − |
| 9 | 86 | m | Restenosis after PTCA | RCA | 5 m | 5 m | − | + | + | − | − | − |
| 10 | 44 | m | Restenosis after PTCA | LAD | 6 m | 6 m | + | + | + | − | − | + |
| 11 | 76 | m | AMI | LAD | 6 m | 6 m | − | + | + | − | − | − |
| 12 | 46 | m | Restenosis after PTCA | LAD | 5 m | 5 m | − | + | + | − | − | + |
| 13 | 69 | m | Restenosis after PTCA | LAD | 4 m | 16 m | − | + | + | − | + | − |

All atherectomy specimen were immediately frozen in liquid nitrogen after debulking of the lesion, and kept in liquid nitrogen until mRNA preparation was performed as described above.

The control group consisted of 5 specimen of muscular arteries of the intestine from five patients and 6 specimen from coronary arteries from three patients who underwent heart transplantation. The control specimen were immediately frozen in liquid nitrogen. Prior to mRNA preparation, media and intima of the arteries were prepared. A small piece of the specimen (approx. 1 $mm^3$) was immediately lysed, whereas the rest was histologically examined for atherosclerotic changes. If there were no atherosclerotic changes of vessel morphology detectable, the specimen were used as "healthy" control samples and mRNA and cDNA preparation was performed as described.

The neointimal tissue of carotid (n=3) and femoralis (n=3) arteries was generated by atherectomy within the restenosis and immediately frozen after removal in liquid nitrogen. For histologic evaluation and immunohistochemistry of the in-stent restenotic tissue from coronary arteries (n=3) and of the neointima of restenotic peripheral arteries (n=6), the samples were fixed in 4% paraformaldehyd and embedded in paraffin as described.

Blood samples were obtained immediately after revascularization of the restenotic vessel. Eight ml blood samples were collected into 35 ml of TriReagent Blood (MBI Fermentas, Germany) and subsequently frozen at −80° C. until RNA preparation was performed as described in the manufacture's protocol. 1 μg of total RNA of blood cells were dissolved in 1000 μL Lysis/Binding buffer and mRNA and cDNA synthesis was prepared as described above.

$1×10^4$ cells were subsequently lysed in 1000 μL Lysis/Binding puffer before mRNA was prepared as described above.

Determination of Gene Expression Patterns was carried out as follows:

Sample mRNA preparation, cDNA synthesis, PCR amplification and probe labeling, cDNA array hybridization and data analysis were performed as described hereinabove, in particular in Example V. The obtained cDNA probes were hybridized to Human 1.2, Cancer 1.2, Cardiovascular and Stress cDNA arrays (Clontech, Heidelberg, Germany) with a total of 2,435 genes of known function. There was an approximately 20% redundancy of genes among cDNA arrays. For analysis of microscopic human tissue samples down to a single cell level the here described new method of cDNA synthesis and PCR amplification was used (see Examples I to V).

Quantification of array data was performed by scanning of the films and analysis with array vision software (Imaging Research Inc., St. Catharines, Canada). Background was subtracted and signals were normalized to the nine housekeeping genes present on each filter, whereby the average of the housekeeping gene expression signals was set to 1 and the background set to 0. For the logarithmic presentation shown in FIG. 1, values were multiplied by 1000. A mean value $≧0,05$ in the average of all samples in one group was regarded as a positive signal. Differences in the mean expression level by a factor $≧2.5$-fold between the study and the control group were further statistically analyzed.

Results of the experimental analysis are given as mean expression values of the ten examined specimen of the study group or the eleven examined specimen of the control group.

Differences between the patient and donor groups were analyzed by the Wilcoxon-test (SPSS version 8.0). Genes were only considered to be differentially expressed between the two groups if their p-values in the Wilcoxon test were <0.03, and if a differential expression was observed in at least 5 out of 10 samples within one study group, while there was 0 out of 10 within the other group; or at least 7 out of 10 samples within one group, while there were maximally 3 out of 10 within the other group.

Immunhistochemistry was carried out as follows:

Immunhistochemistry was performed on paraffin-embedded sections from 3 neointima specimen from coronary in-stent restenosis, 3 neointima specimen from A. femoralis and 3 neointima specimen from carotid neointima specimen. Three μm serial sections were mounted onto DAKO ChemMate™ M Capillary Gap Microscope slides (100 μm), baked at 65° C. overnight, deparaffinized and dehydrated according to routine protocols. For antigen retrieval, specimen were boiled 4 minutes in a pressure cooker in citrate buffer (10 mMol, pH 6.0). Endogenous peroxidase was blocked by 1% $H_2O_2$/methanol for 15 minutes. Unspecific binding of the primary antibodies was reduced by preincubation of the slides with 4% dried skim milk in Antibody Diluent (DAKO, Denmark). Immunostaining was performed by the streptavidin-peroxidase technique using the Dako ChemMate Detection Kit HRP/Red Rabbit/Mouse (DAKO Denmark) according to the manufacturers description. The procedures were carried out in a DAKO TechMate™ 500 plus automated staining system. Primary antibodies against smooth muscle actin (M0635, DAKO, Denmark; 1:300), CD3 (A0452, DAKO, Denmark; 1:80), MAC387 (E026, Camon, Germany; 1:20) and IRF-1 (sc-497, Santa Cruz, U.S.A.) were diluted in Antibody Diluent and incubated for 1 h at room temperature. After nuclear counterstaining with hematoxylin, slides were dehydrated and coverslipped with Pertex (Medite, Germany).

The following results were obtained:

(a) Differential Gene Expression in Human Neointima

Figure 13:
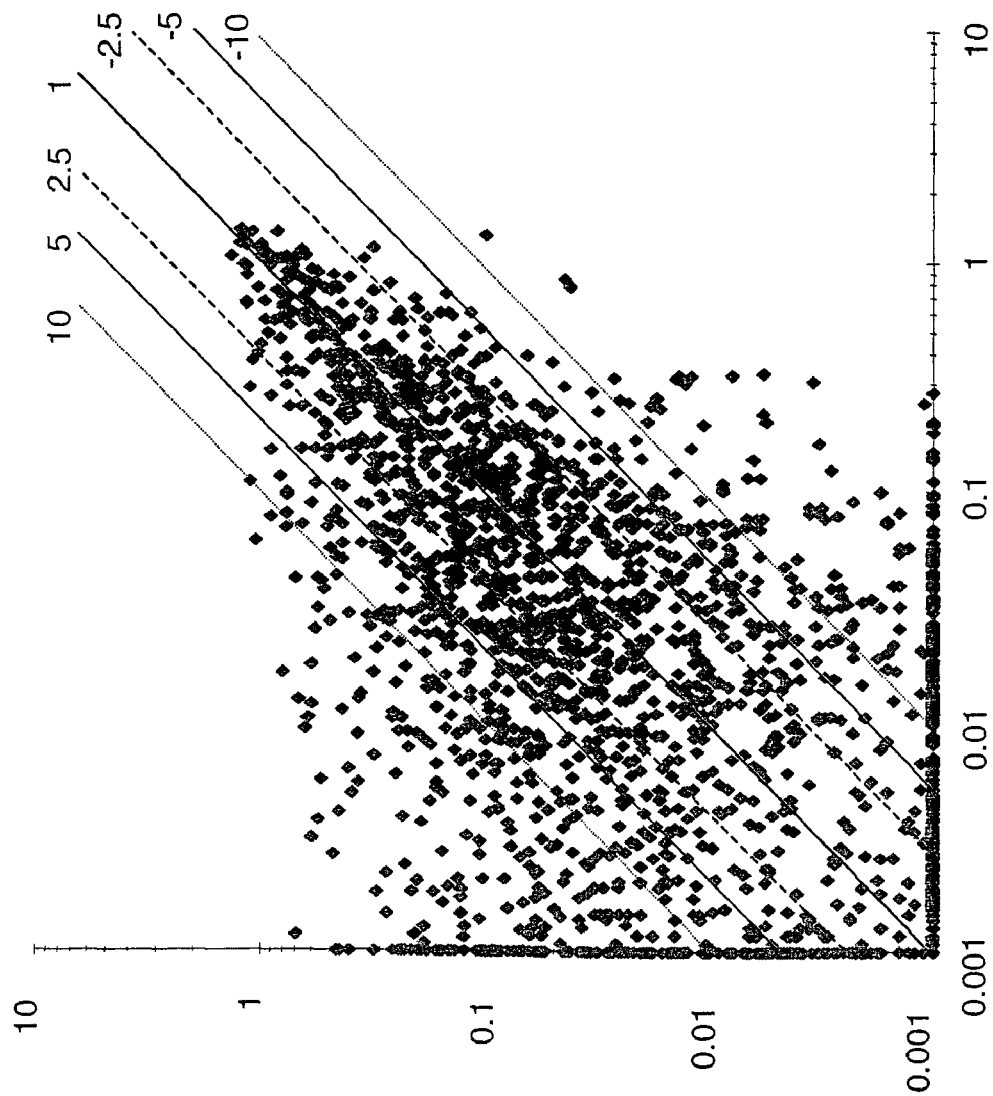
FIG. 13: cDNA array analysis of gene expression. Four Clontech Atlas microarrays, containing a total of 2435 human cDNAs, were hybridized with cDNA labeled with Dig-dUPT prepared from RNA from in-stent neointima (n=10) and from control media/intima (n=11) as described in Materials and Methods. Spots indicate the mean of the relative expression of the two examined groups. Panel A shows the expression of all examined genes in this study. Panel B shows expression of the 224 differentially expressed genes, that were more than 2.5-fold induced or reduced in neointima and showed a statistical significance p<0.03 in the Wilcoxon test. For this presentation, zero value were replaced by a value of 0.0001, as a zero value is not representable in a logarithmic scale.
Figure 13:
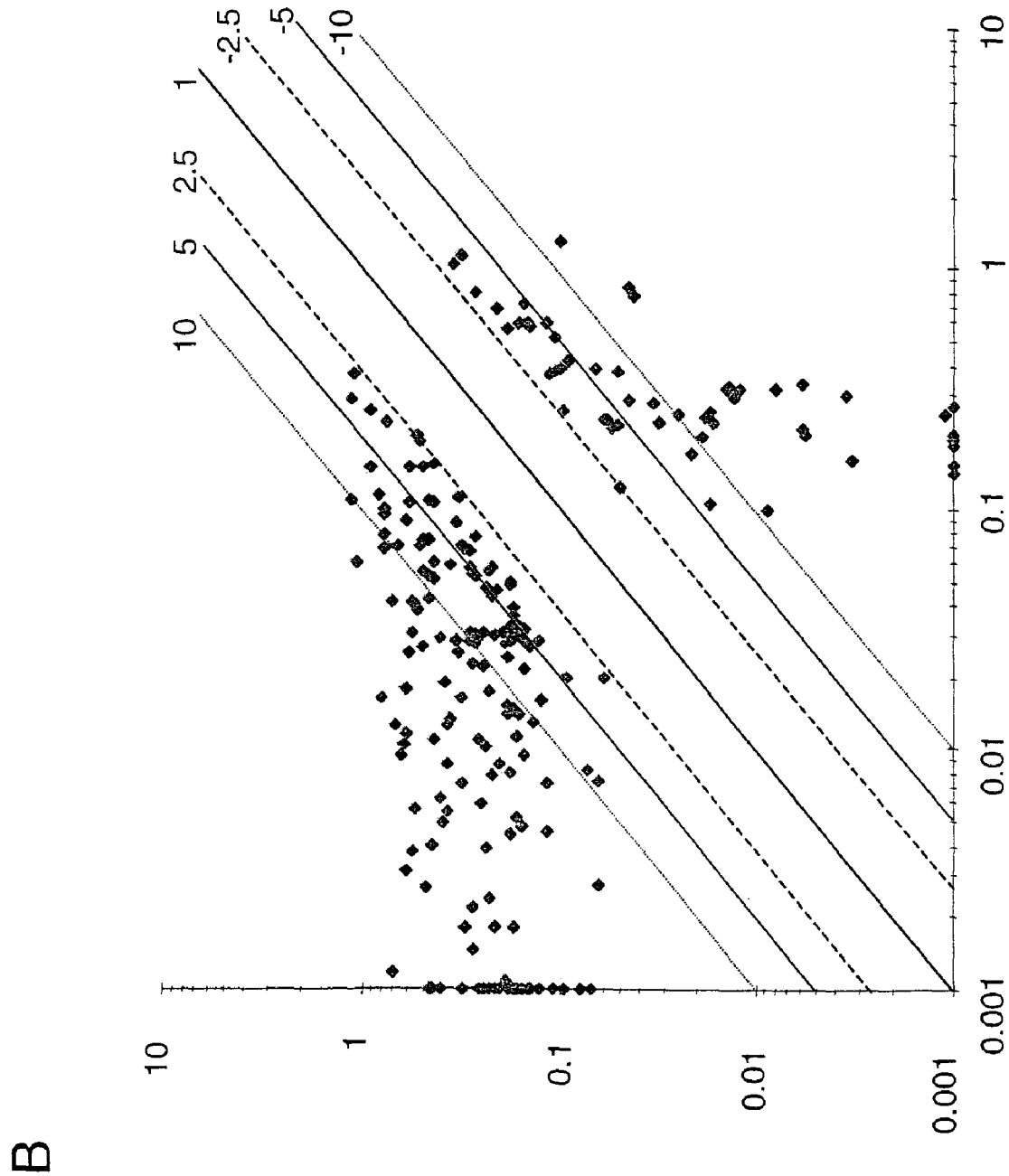

A total of 1,186 genes (48.7%) out of 2,435 yielded detectable hybridization signals on cDNA arrays with neointima and control samples over a 20-fold range of expression level (FIG. 13A) Thereof 352 genes (14.5%) appeared to be differentially expressed by a factor >2.5-fold between restenotic and control samples. However, expression levels considerably varied among individual samples (see, e.g., FIG. 15). Therefore, a statistical analysis was employed to identify those genes that are differentially expressed between study and control groups with high significance (see Methods). This way, 224 genes (9.6%) were identified that were differentially expressed by a factor of at least 2.5-fold between the restenosis study group and the control group with a significance in the Wilcoxon test of p<0.03. 167 (75%) genes thereof were found overexpressed and 56 genes (25%) underexpressed in the restenosis study group compared to the control group (FIG. 13B).

Figure 16:
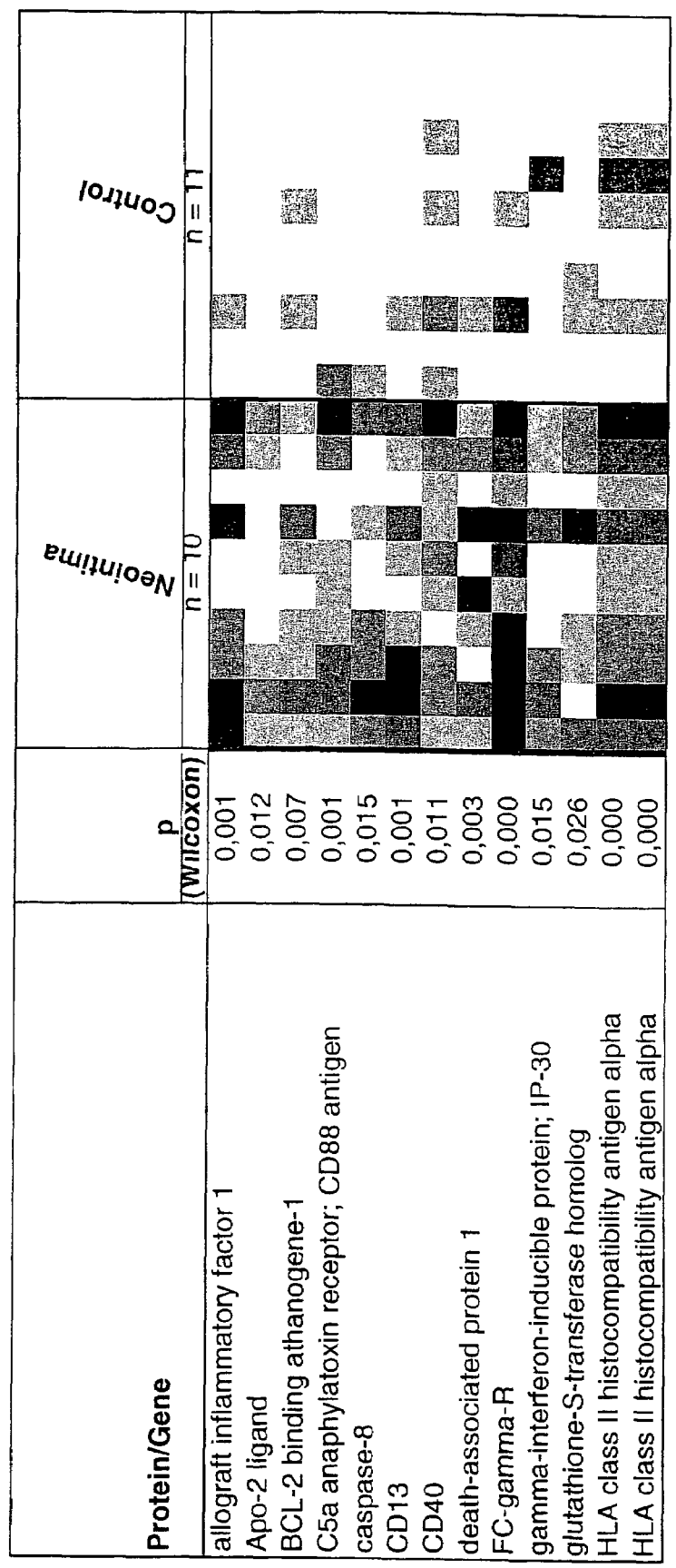
Figure 16:
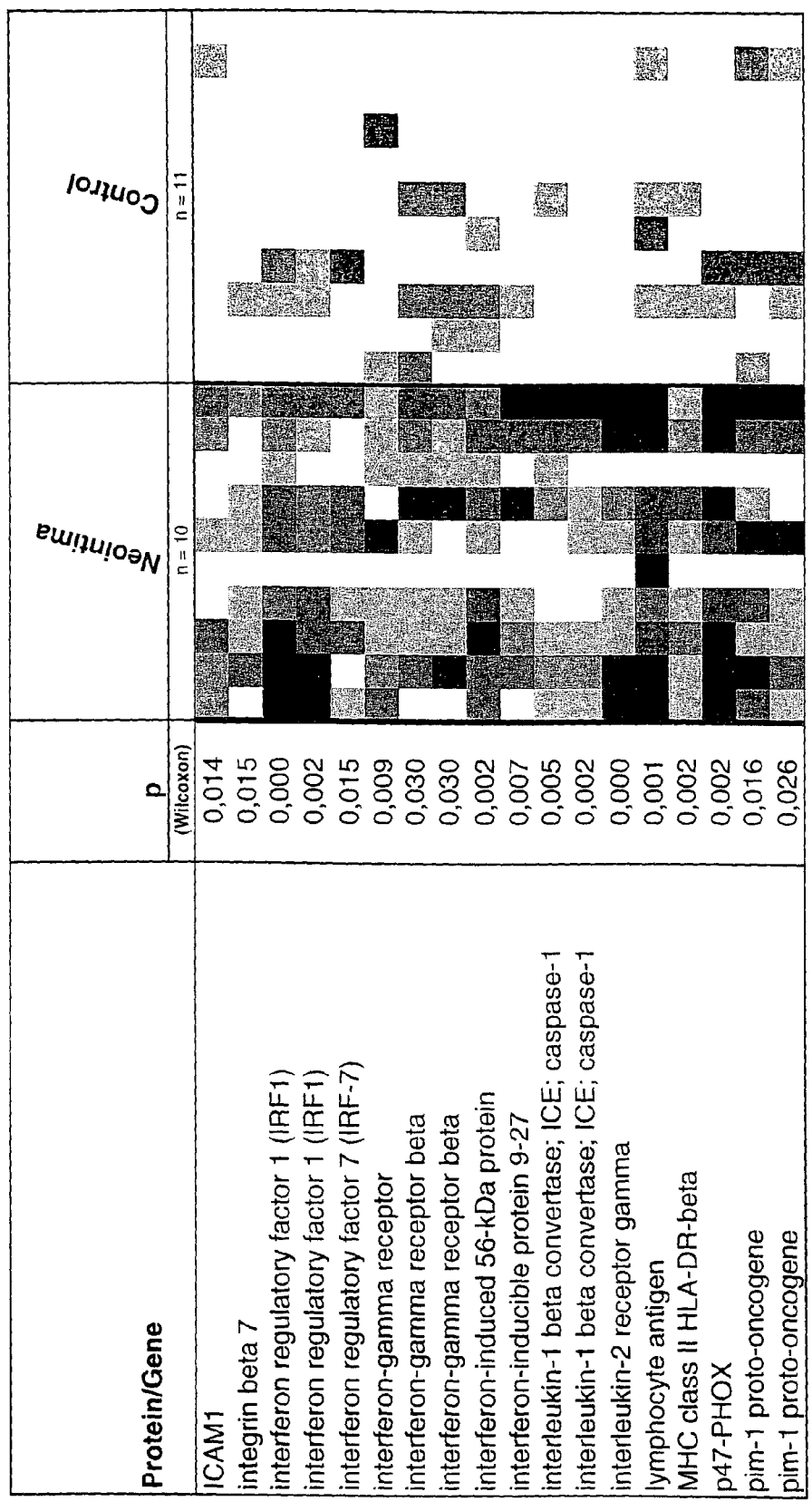
Figure 16:
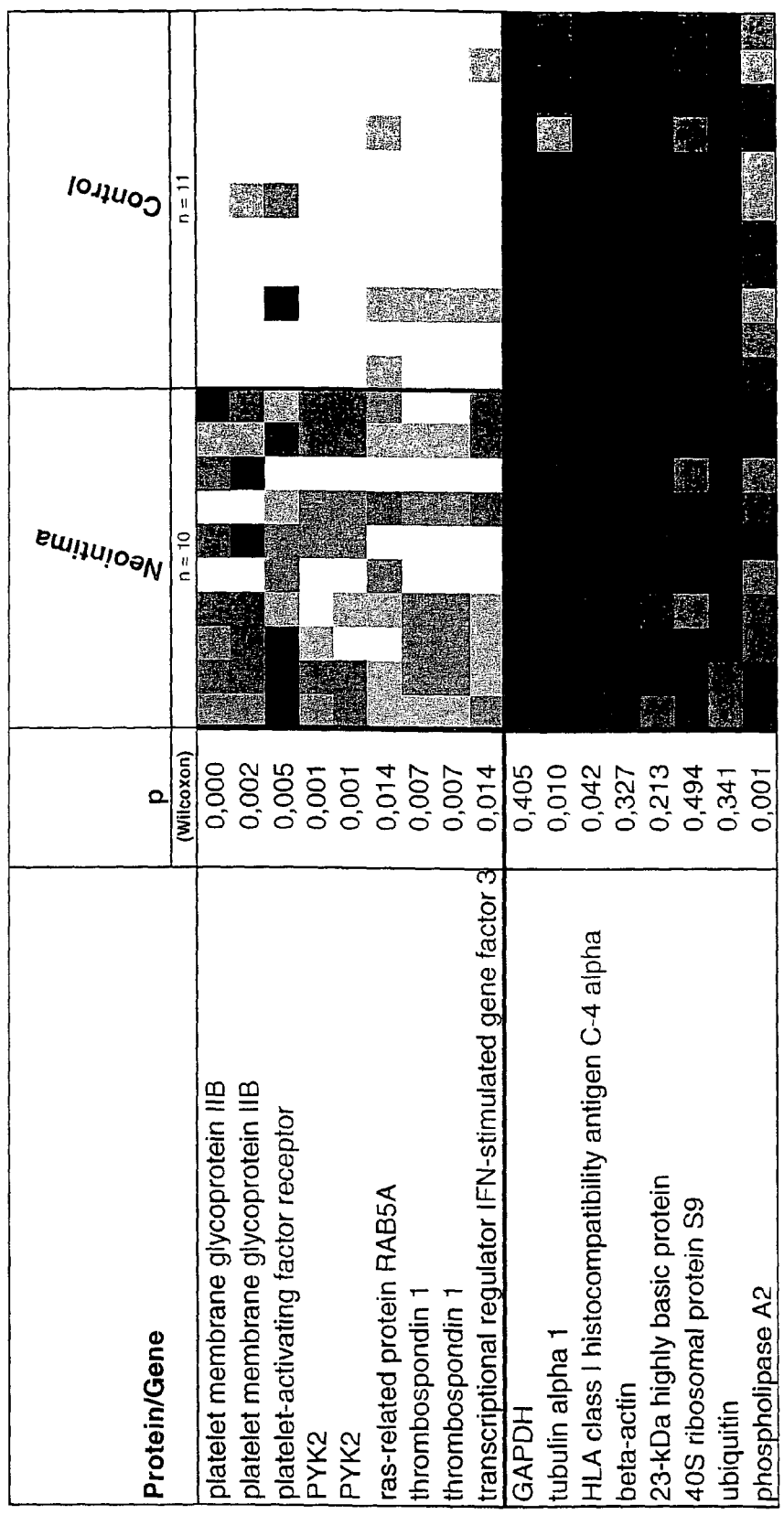

In addition to the statistical significance, the validity of expression data was supported by a 20% redundancy of cDNA elements on the four arrays used. This way, a substantial number of hybridization signals was determined in duplicate or triplicate in independent hybridization experiments. Four examples of duplicate determinations are shown in FIG. 16 (top) which all showed a high degree of reproducibility. As a further validation of hybridization signals, 38 of the differentially expressed genes were selected for PCR analysis of cDNA samples using gene-specific primers. Hybridization signals for 35 (92%) out of 38 genes could be verified by gene-specific PCR yielding signals of the predicted size and relative quantity (data not shown). These data shows that the employed cDNA array approach is comparable with respect to quality and sensitivity to gene-specific PCR. Lastly, among the 224 aberrantly expressed genes in neointima 112 have previously been described in the literature as being expressed in neointima, SMCs, fibroblasts, endothelial cells or mesenchym (FIG. 14 marked with '#').

With respect to neointima expression, the 224 aberrantly regulated genes fell into four subgroups (FIG. 14). Group I lists 62 genes that were overexpressed in neointima and not highly or detectably expressed in control vessels, CASMCs or blood cells (FIG. 14A). In group II, 43 genes are listed that are similarly expressed in neointima and CASMCs, suggesting that this gene cluster in neointima was contributed by proliferating SMCs (FIG. 14B). In group III, 62 genes are listed that are similarly expressed in neointima and blood cells, suggesting that this gene cluster was contributed to that of neointima by infiltrated blood cells (FIG. 14C). This notion is supported by the expression in group III of the largest number of genes related to inflammation in all four groups. Lastly, in group IV, 56 genes are listed that are downregulated in neointima compared to the control group (FIG. 14D). In the following, the aberrant expression of selected genes in neointima will be discussed in the context of gene function.

In summary, the following differentially expressed genes have been detected in human neointima:

| Gene Name | GenBank Accession # | SwissProt Accession # |
| --- | --- | --- |
| 80-kDa nuclear cap-binding protein | D32002 | Q09161 |
| activator 1 140-kDa subunit (A1 140-kDa subunit); replication factor C large subunit; DNA-binding protein PO-GA | L14922 | P35251 |
| activator 1 37-kDa subunit; replication factor C 37-kDa subunit (RFC37); RFC4 | M87339 | P35249 |
| adenylate kinase isoenzyme 1 (AK1); ATP-AMP transphosphorylase; myokinase | J04809 | P00568 |
| adipocyte fatty acid-binding protein 4 (FABP4; AFABP); adipocyte lipid-binding protein (ALBP) | J02874 | P15090 |
| allograft inflammatory factor 1 (AIF1); ionized calcium-binding adapter molecule 1 | U19713 | P55008 |
| alpha-1-antitrypsin precursor; alpha-1 protease inhibitor; alpha-1-antiproteinase | X02920 | P01009 |
| alpha-2-antiplasmin | D00174 | P08697 |
| alpha-2-macroglobulin precursor (alpha-2-M) | M11313 | P01023 |
| alpha-galactosidase A precursor; melibiase; alpha-D-galactoside galactohydrolase | X05790 | P06280 |
| amiloride-sensitive epithelial sodium channel beta subunit; nonvoltage-gated sodium channel 1 beta | X87159 | P51168 |

| Gene Name | GenBank Accession # | SwissProt Accession # |
|---|---|---|
| subunit (SCNEB; beta NACH); SCNN1B | | |
| angiotensinogen precursor (AGT) | K02215 | P01019 |
| apolipoprotein E precursor (APOE) | M12529 | P02649 |
| atrial natriuretic peptide receptor B precursor (ANPB; NPRB); guanylate cyclase B (GCB) | L13436 | P20594 |
| autosomal dominant polycystic kidney disease II (PKD2) | U50928 | Q13563 |
| B-cell-associated molecule CD40 | X60592 | P25942 |
| BCL-2 binding athanogene-1 (BAG-1); glucocorticoid receptor-associated protein RAP46 | S83171; Z35491 | Q99933 |
| BCL-2-related protein A1 (BCL2A1); BFL1 protein; hemopoietic-specific early response protein; GRS protein | U29680; Y09397 | Q16548; Q99524 |
| BIGH3 | M77349 | Q15582 |
| bikunin; hepatocyte growth factor activator inhibitor 2 | U78095 | O00271; O43291 |
| brain glucose transporter 3 (GTR3) | M20681 | P11169 |
| brain-specific polypeptide PEP-19; brain-specific antigen PCP-4 | U52969 | P48539 |
| Bruton's tyrosine kinase (BTK); agammaglobulinaemia tyrosine kinase (ATK); B-cell progenitor kinase (BPK) | U10087; X58957 | Q06187 |
| C5a anaphylatoxin receptor (C5AR); CD88 antigen | M62505 | P21730 |
| cadherin 16 (CDH16); KSP-cadherin | AF016272 | P75309 |
| calcium & integrin-binding protein (CIB) | U85611 | Q99828 |
| carboxypeptidase H precursor (CPH); carboxypeptidase E (CPE); enkephalin convertase; prohormone processing carboxypeptidase | X51405 | P16870 |
| carboxypeptidase N | X14329 | P15169 |
| caspase-8 precursor (CASP8); ICE-like apoptotic protease 5 (ICE-LAP5); MORT1-associated CED-3 homolog (MACH); FADD-homologous ICE/CED-3-like protease (FADD-like ICE; FLICE); apoptotic cysteine protease MCH-5 | U60520; U58143; X98172; AF00962 | Q14790; Q15780 |
| caveolin 3 | AF043101 | P56539 |
| CBL-B | U26710 | Q13191 |
| CDC42 homolog; G25K GTP-binding protein (brain isoform + placental isoform) | M35543 + M57298 | P21181 + P25763 |
| cell surface adhesion glycoproteins LFA-1/CR3/p150,95 beta-subunit precursor; LYAM1; integrin beta 2 (ITGB2); CD18 antigen; complement receptor C3 beta subunit | M15395 | P05107; Q16418 |
| cell surface glycoprotein mac-1 alpha subunit precursor; CD11B antigen; leukocyte adhesion receptor MO1; integrin alpha M (ITGAM); neutrophil adherence receptor alpha M subunit; CR3A | J04145 | P11215 |
| cell surface glycoprotein MUC18; melanoma-associated antigen A32; CD146 antigen; melanoma adhesion molecule | M28882 | P43121 |
| C-fgr proto-oncogene (p55-FGR); SRC2 | M19722 | P09769 |
| c-fos proto-oncogene; G0S7 protein | K00650 | P01100 |
| chemokine receptor-like 2; IL8-related receptor DRY12; flow-induced endothelial G protein-coupled receptor (FEG1); G protein-coupled receptor GPR30; GPCR-BR) | AF015257 | Q99527; Q99981; O00143; Q13631 |
| clone 23815 (Soares library 1NIB from IMAGE consortium) | U90916 | none |
| coagulation factor XII | M11723 | P00748 |
| collagen 16 alpha 1 subunit precursor (COL16A1) | M92642 | Q07092 |
| collagen 18 alpha 1 subunit (COL18A1) | L22548 | P39060 |
| collagen 6 alpha 1 subunit (COL6A1) | X15880 | P12109 |
| collagen 6 alpha 2 subunit (COL6A2) | M34570 | Q13909; Q13911 |
| coronin-like protein P57 | D44497 | P31146 |
| c-src kinase (CSK); protein-tyrosine kinase cyl | X59932 | P41240 |
| cyclin-dependent kinase 4 inhibitor (CDK4I; CDKN2); p16-INK4; multiple tumor suppressor 1 (MTS1) | L27211 | P42771; Q15191 |
| cyclin-dependent kinase inhibitor 1 (CDKN1A); melanoma differentiation-associated protein 6 (MDA6); CDK-interacting protein 1 (CIP1); WAF1 | U09579; L25610 | P38936 |
| cytidine deaminase (CDA) | L27943 | P32320 |
| death-associated protein 1 (DAP1) | X76105 | P51397 |
| desmin (DES) | U59167 | P17661; Q15787 |
| DNAX activation protein 12 | AF019562 | O43914 |
| dual-specificty A-kinase anchoring protein 1 | X97335 | Q92667 |
| early growth response protein 1 (hEGR1); transcription factor ETR103; KROX24; zinc finger protein 225; AT225 | X52541; M62829 | P18146 |
| early response protein NAK1; TR3 orphan receptor | L13740 | P22736 |
| endothelial differentiation gene 1 (EDG1) | M31210; AF022137 | P21453 |
| endothelin 2 (ET2) | M65199 | P20800 |
| ephrin A receptor 4 precursor; tyrosine-protein kinase receptor sek; hek8 | L36645 | P54764 |
| epithelial discoidin domain receptor 1 precursor (EDDR1; DDR1); cell adhesion kinase (CAK); TRKE; RTK6 | | X74979 |
| estradiol 17 beta-dehydrogenase 1 | M36263 | P14061 |
| estrogen-related receptor alpha | X51416; Y00290 | P11474 |
| ets domain protein elk-3; NET; SRF accessory protein 2 (SAP2) | Z36715 | P41970 |
| extracellular superoxide dismutase precursor (EC-SOD; SOD3) | J02947 | P08294 |
| farnesyltransferase beta | L10414 | P49356 |
| FC-epsilon-receptor gamma subunit | M33195 | P30273 |

-continued

| Gene Name | GenBank Accession # | SwissProt Accession # |
|---|---|---|
| FK506-binding protein (FKBP; FKBP12); peptidyl-prolyl cis-trans isomerase (PPIASE); rotamase | M34539; M80199; M92423; J05340; X55741; M93255 | M80706; X52220 |
| fli-1 oncogene; ergB transcription factor | M93255 | Q01543 |
| FMLP-related receptor I (FMLPRII); RMLP-related receptor I (RMLPRI) | M76673 | P25089 |
| focal adhesion kinase 2 (FADK2; FAK2); cell adhesion kinase beta (CAKbeta); proline-rich tyrosine kinase 2 (PYK2) | L49207 + U43522 + U33284 | Q14289; Q16709; Q13475 |
| frizzled-related FrzB (FRITZ) + FrzB precursor + frezzled (FRE) | U91903 + U24163 + U68057 | O00181 + Q92765 + Q99686 |
| G protein-coupled receptor EDG4 | AF011466 | O43431 |
| G1/S-specific cyclin D1 (CCND1); cyclin PRAD1; bcl-1 oncogene | X59798; M64349 | P24385 |
| G1/S-specific cyclin D3 (CCND3) | M92287 | P30281 |
| gamma-interferon-inducible protein; IP-30 | J03909 | P13284 |
| GAP junction alpha-1 protein | X52947 | P17302 |
| glutathione-S-transferase (GST) homolog | U90313 | P78417 |
| glycerol kinase | L13943 | P32189 |
| G-protein-coupled receptor HM74 | D10923 | P49019 |
| granulocyte colony stimulating factor receptor precursor (GCSF-R); CD114 antigen | M59818 | Q99062 |
| granulocyte-macrophage colony-stimulating factor receptor alpha (GM-CSFR-alpha); CSW116 antigen | X17648 | P15509 |
| growth arrest & DNA-damage-inducible protein 45 beta (GADD45 beta) | AF078077 | none |
| growth arrest & DNA-damage-inducible protein 45 gamma (GADD45 gamma) | AF078078 | none |
| growth factor receptor-bound protein 2 (GRB2) isoform; GRB3-3; SH2/SH3 adaptor GRB2; ASH protein + epidermal growth factor receptor-bound protein 2 (EGFRBP-GRB2) | L29511; M96995 | P29354 |
| growth inhibitory factor; metallothionein-III (MT-III) | D13365; M93311 | P25713 |
| GTP-binding protein ras associated with diabetes (RAD1) | L24564 | P55042 |
| guanine nucleotide-binding protein G(Y) alpha 11 subunit (GNA11; GA11) | M69013 | P29992; Q14350; O15109 |
| heart fatty acid-binding protein 3 (FABP3; HFABP); muscle fatty acid-binding protein (MFABP); mammary-derived growth inhibitor (MDGI) | Y10255 | P05413; Q99957 |
| heat shock 70-kDa protein 6 (heat shock 70-kDa protein B) | X51757; M11236 | P48741 |
| heat shock cognate 71-kDa protein | Y00371 | P11142 |
| heme oxygenase 1 (HO1); HSOXYGR | X06985 | P09601 |
| high mobility group protein (HMG-I) | M23619 | P17096 |
| high-affinity interleukin-8 receptor A (IL-8R A); IL-8 receptor type 1; CDW128 | M68932 | P25024 |
| high-affinity nerve growth factor receptor precursor; trk-1 transforming tyrosine kinase protein; p140-TRKA; p68-trk-T3 oncoprotein | X03541 | P04629 |
| histone H4 | X67081 | none |
| HLA class II histocompatibility antigen alpha subunit precursor (MHC-alpha) | M31525 | P06340 |
| homeobox protein HOXB7; HOX2C; HHO.c1 | M16937 | P09629 |
| hormone-sensitive lipase | | Q05469 |
| hydroxyacyl-CoA dehydrogenase; 3-ketoacyl-CoA thiolase; enoyl-CoA hydratase beta subunit | D16481 | P55084 |
| IgG receptor FC large subunit P51 precursor (FCRN); neonatal FC receptor; IgG FC fragment receptor transporter alpha chain | U12255 | P55899 |
| IMP dehydrogenase 1 | J05272 | P20839 |
| insulin receptor precursor (INSR) | M10051; X02160 | P06213 |
| insulin-like growth factor binding protein 6 precursor (IGF-binding protein 6; IGFBP6; IBP6) | M62402 | P24592 |
| insulin-like growth factor I receptor (IGF1R) | X04434; M24599 | P08069 |
| integrin alpha 3 (ITGA3); galactoprotein B3 (GAPB3); VLA3 alpha subunit; CD49C antigen | M59911 | P26006 |
| integrin alpha 7B precursor (IGA7B) | X74295 | Q13683 |
| integrin alpha 8 (ITGA8) | L36531 | P53708 |
| integrin beta 7 precursor (ITGB7) | M62880; S80335 | P26010 |
| inter-alpha-trypsin inhibitor heavy chain H4 precursor (ITI heavy chain H4); plasma kallikrein-sensitive glycoprotein 120 (PK-120) | D38595 | Q14624 |
| intercellular adhesion molecule 2 precursor (ICAM2); CD102 antigen | X15606 | P13598 |
| intercellular adhesion molecule 3 precursor (ICAM3); CDW50 antigen; ICAM-R | X69711; X69819 | P32942 |
| intercellular adhesion molecule-1 precursor (ICAM1); major group rhinovirus receptor; CD54 antigen | J03132 | P05362 |
| interferon regulatory factor 1 (IRF1) | X14454 | P10914 |
| interferon regulatory factor 7 (IRF-7) | U73036 | Q92985 |
| interferon-gamma (IFN-gamma) receptor beta subunit precursor; IFN-gamma accessory factor 1 (AF1); IFN-gamma transducer 1 (IFNGT1) | U05875 | P38484 |
| interferon-gamma receptor (IFNGR) | A09781 | none |
| interferon-induced 56-kDa protein (IFI-56K) | X03557 | P09914 |
| interferon-inducible protein 9–27 | J04164 | P13164 |
| interleukin-1 beta convertase precursor (IL-1BC); IL-1 beta converting enzyme (ICE); p45; caspase-1 (CASP1) | U13699; M87507; X65019 | P29466 |
| interleukin-1 receptor type II precursor (IL-1R2); IL-1R-beta | X59770 | P27930 |
| interleukin-16 (IL-16); lymphocyte chemoattractant factor (LCF) | M90391 | Q14005 |
| interleukin-2 receptor gamma subunit (IL-2R gamma; IL2RG); cytokine receptor common gamma chain precursor; p64 | D11086 | P31785 |
| interleukin-6 receptor alpha subunit precursor (IL-6R-alpha; IL6R); CD126 antigen | M20566; X12830 | P08887 |
| I-rel (RELB) | M83221 | Q01201 |
| leukocyte IgG receptor (FC-gamma-R) | J04162 | P08637 |
| lipoprotein-associated coagulation inhibitor | J03225 | P10646 |
| low affinity immunoglobulin gamma FC receptor II-A precursor (FC-gamma RII-A; FCRII-A; IgG FC | M31932 | P12318 |

| Gene Name | GenBank Accession # | SwissProt Accession # |
|---|---|---|
| receptor II-A); CD32 antigen | | |
| low-density lipoprotein receptor-related protein LR11 precursor | Y08110 | Q92673 |
| L-selectin precursor; lymph node homing receptor (LNHR); leukocyte adhesion molecule 1 (LAM1) leukocyte surface leu-8 antigen; GP90-MEL; leukocyte-endothelial cell adhesion molecule 1 (LECAM1); CD62L antigen; SELL | M25280 | P14151 |
| LUCA2; lysosomal hyaluronidase 2 (HYAL2); PH-20 homolog | U09577 | Q12891 |
| lymphocyte antigen | M81141 | Q30099 |
| lymphoid-restricted homolog of SP100 protein (LYSP100) | U36500 | Q13342 |
| lymphotoxin-beta (LT-beta; LTB); tumor necrosis factor C (TNFC) | L11015 | Q06643 |
| lysosomal acid lipase/cholesteryl ester hydrolase precursor (LAL); acid cholesteryl ester hydrolase; sterol esterase; lipase A (LIPA); cholesteryl esterase | M74775 | P38571 |
| lysosomal pro-X carboxypeptidase | L13977 | P42785 |
| macrophage colony stimulating factor I receptor precursor (CSF-1-R); fms proto-oncogene (c-fms); CD115 | X03663 | P07333 |
| macrosialin precursor | S57235 | P34810 |
| manic fringe | U94352 | O00587 |
| matrix metalloproteinase 17 (MMP17); membrane-type matrix metalloproteinase 4 (MT-MMP4) | X89576 | Q14850 |
| matrix metalloproteinase 9 (MMP9); gelatinase B; 92-kDa type IV collagenase precursor (CLG4B) | J05070; D10051 | P14780 |
| MHC class II HLA-DR-beta (DR2-DQW1/DR4 DQW3) precursor | M20430 | Q30166 |
| microsomal aminopeptidase N; myeloid plasma membrane glycoprotein CD13 | M22324 | P15144 |
| microtubule-associated protein 1B | L06237 | P46821 |
| migration inhibitory factor-related protein 14 (MRP14); calgranulin B; leukocyte L1 complex heavy subunit; S100 calcium-binding protein A9 | X06233 | P06702 |
| migration inhibitory factor-related protein 8 (MRP8); calgranulin A; leukocyte L1 complex light subunit; S100 calcium-binding protein A8; cystic fibrosis antigen (CFAG) | X06234 | P05109 |
| myeloid cell nuclear differentiation antigen (MNDA) | M81750 | P41218 |
| myotonin-protein kinase; myotonic dystrophy protein kinase (MDPK); DM-kinase (DMK) | L19268 | Q09013 |
| neurogenic locus notch protein (N) | M99437 | Q04721 |
| neurogranin (NRGN); RC3 | Y09689 | Q92686 |
| neurotrophic tyrosine kinase receptor-related 3; TKT precursor | X74764 | Q16832 |
| neutrophil cytosol factor 2; neutrophil NADPH oxidase factor 1 (NCF1); p47-PHOX; 47-kDa autosomal chronic granulomatous disease protein | M25665 | P14598 |
| neutrophil gelatinase-associated lipocalin precursor (NGAL); 25-kDa alpha-2-microglobulin-related subunit of MMP9); lipocalin 2; oncogene 24P3 | X99133 | P80188 |
| ninjurin-1 | U72661 | Q92982 |
| NKG5 protein precursor; lymphokine LAG2; T-cell activation protein 519 | X54101 | P22749 |
| NT-3 growth factor receptor precursor (NTRK3); C-trk tyrosine kinase (TRKC) | U05012 | Q16288; Q16289; Q12827 |
| nuclear receptor-related 1 | X75918 | P43354 |
| NuMA | Z11583 | Q14981 |
| osteoclast stimulating factor | U63717 | Q92882 |
| P126 (ST5) | U15131 | P78524 |
| P2X purinoceptor 1; ATP receptor P2X1 | X83688 | P51575 |
| P2X purinoceptor 5 (P2X5) | AF016709 | Q93086 |
| paxillin | U14588 | P49023 |
| PC8 precursor | U33849 | Q16549 |
| peripheral myelin protein 22 (PMP22); CD25 protein; SR13 myelin protein | D11428 | Q01453 |
| peroxisomal bifunctonal enzyme | L07077 | Q08426 |
| phenol-sulfating phenol sulfotransferase 1 (PPST1); thermostable phenol sulfotransferase (TS-PST); HAST1/HAST2; ST1A3; STP1 + PPST2; ST1A2; STP2 + monoamine-sulfating phenol sulfotransferase | U09031 + U28170 + L19956 | P50225 + P50226 + P50224 |
| phospholipase C beta 2 (PLC-beta 2; PLCB2); 1-phosphatidylinositol 4,5-bisphosphate phosphodiesterase beta 2 | M95678 | Q00722 |
| phosphoribosyl pyrophosphate synthetase subunit I | D00860 | P09329 |
| PIG7 | AF010312 | Q99732 |
| pim-1 proto-oncogene | M54915 | P11309 |
| platelet basic protein precursor (PBP); connective tissue activating peptide III (CTAP III); low-affinity platelet factor IV (LA PF4); beta thromboglobulin (beta TG); neutrophil activating peptide 2 (NAP2) | M54995; M38441 | P02775 |
| platelet endothelial cell adhesion molecule | HS78146 | P16284 |
| platelet membrane glycoprotein IIB precursor (GP2B); integrin alpha 2B (ITGA2B); CD41 antigen | M34480; J02764 | P08514 |
| platelet membrane glycoprotein IIIA precursor (GP3A); integrin beta 3 (ITGB3); CD61 antigen | J02703; M25108 | P05106; Q13413; Q16499 |
| platelet-activating factor receptor (PAFR) | D10202 | P25105 |
| platelet-derived growth factor A subunit precursor (PDGFA; PDGF-1) | X06374 | P04085 |
| PRB-binding protein E2F1; retinoblastoma-binding protein 3 (RBBP3); retinoblastoma-associated protein 1 (RBAP1); PBR3 | M96577 | Q01094; Q92768; Q13143 |
| prostaglandin G/H synthase 1 | | P23219 |
| protein-tyrosine phosphatase 1C (PTP1C); hematopoietic cell protein-tyrosine phosphatase; SH-PTP1 | X62055 | P29350 |
| prothrombin precursor; coagulation factor II | V00595 | P00734 |
| proto-oncogene tyrosine-protein kinase lck; p56-lck; lymphocyte-specific protein tyrosine kinase (LSK); T-cell-specific protein-tyrosine kinase | U07236 | P06239 |
| P-selectin precursor (SELP); granule membrane protein 140 (GMP140); PADGEM; CD62P antigen; leukocyte-endothelial cell adhesion molecule 3 (LECAM3) | M25322 | P16109 |

-continued

| Gene Name | GenBank Accession # | SwissProt Accession # |
|---|---|---|
| purine-rich single-stranded DNA-binding protein alpha (PURA) | M96684 | Q00577 |
| rab geranylgeranyl transferase alpha subunit | Y08200 | Q92696 |
| rab geranylgeranyl transferase beta subunit | Y08201 | P53611; Q92697 |
| RaIB GTP-binding protein | M35416 | P11234 |
| ras-related C3 botulinum toxin substrate 2; p21-rac2; small G protein | M64595; M29871 | P15153 |
| ras-related protein RAB5A | M28215 | P20339 |
| related to receptor tyrosine kinase (RYK) | S59184 | P34925 |
| replication protein A 70-kDa subunit (RPA70; REPA1; RF-A); single-stranded DNA-binding protein | M63488 | P27694 |
| rho GDP dissociation inihibitor 2 (RHO GDI2; RHO-GDI beta); LY-GDI; ARHGDIB; GDID4 | L20688 | P52566 |
| rho-GAP hematopoietic protein C1 (RGC1); KIAA0131 | X78817 | P98171 |
| rho-related GTP-binding protein (RHOG); ARHG | X61587 | P35238 |
| ribonuclease 6 precursor | U85625 | O00584 |
| ribosomal protein S6 kinase II alpha 1 (S6KII-alpha 1); ribosomal S6 kinase 1 (RSK1) | L07597 | Q15418 |
| S100 calcium-binding protein A1; S-100 protein alpha chain | X58079 | P23297 |
| SCGF-beta | D86586 | BAA21499 |
| SEC7 homolog B2-1 | M85169 | Q15438 |
| selectin P ligand | U02297 | Q14242; Q12775 |
| semaphorin; CD100 | U60800 | Q92854 |
| serum response factor (SRF) | J03161 | P11831 |
| SH3-binding protein 2 | AF000936 | P78314 |
| signaling inositol polyphosphate 5 phosphatase; SIP-110 | U50040 | Q13544 |
| sonic hedgehog (SHH) | L38518 | Q15465 |
| specific 116-kDa vacuolar proton pump subunit | U45285 | Q13488 |
| steroid 5-alpha reductase 1 (SRD5A1); 3-oxo-5-alpha steroid 4 dehydrogenase 1 | M32313; M68886 | P18405 |
| stromal cell derived factor 1 receptor (SDF1 receptor); fusin; CXCR4; leukocyte-derived seven transmembrane domain receptor (LESTR); LCR1 | D10924 | P30991 |
| superoxide dismutase 2 | M36693 | P04179 |
| T-cell surface glycoprotein CD3 epsilon subunit precursor; T-cell surface antigen T3/leu-4 epsilon subunit (T3E) | X03884 | P07766 |
| tenascin precursor (TN); hexabrachion (HXB); cytotactin; neuronectin; GMEM; miotendinous antigen; glioma-associated extracellular matrix antigen | X78565; M55618 | P24821; Q15567; Q14583 |
| thrombospondin 1 precursor (THBS1; TSP1) | X14787 | P07996 |
| thymidine phosphorylase precursor (TDRPase); platelet- derived endothelial cell growth factor (PDECGF); gliostatin | M63193 | P19971; Q13390 |
| TNF-related apoptosis inducing ligand (TRAIL); APO-2 ligand (APO2L) | U57059 | P50591 |
| TRAIL receptor 3; decoy receptor 1 (DCR1) | AF016267 | O14755 |
| transcription factor Spi-B | X66079 | Q01892 |
| transcriptional regulator interferon-stimulated gene factor 3 gamma subunit (ISGF3G); interferon-alpha (IFN-alpha) responsive transcription factor subunit | M87503 | Q00978 |
| transforming growth factor-beta 3 (TGF-beta3) | J03241 | P10600 |
| tuberin; tuberous sclerosis 2 protein (TSC2) | X75621 | P49815 |
| type I cytoskeletal 18 keratin; cytokeratin 18 (K18) | M26326 | P05783 |
| type II cytoskeletal 6 keratin: cytokeratin 6A (CK6A); K6A keratin (KRT6A) + CK6B; KRT6B + CK6C; KRT6C + CK6D; KRT6D + CK6E; KRT6E + CK6F; KRT6F | J00269 + L42592 + L42601 + L42610 + L42611 + L42612 | P02538 |
| tyrosine-protein kinase lyn | M16038 | P07948 |
| tyrosine-protein kinase receptor UFO precursor; axl oncogene | M76125 | P30530 |
| vascular endothelial growth factor B precursor (VEGFB) + VEGF-related factor isoform VRF186 | U48801; U43369 | P49765 |
| vav oncogene | X16316 | P15498 |
| v-erbA related protein (EAR2) | X12794 | P10588 |
| versican core protein precursor; large fibroblast proteoglycan; chondroitin sulfate proteoglycan core protein 2; glial hyaluronate-binding protein (GHAP) | U16306; X15998; U26555; D32039 | P13611 |
| vitamin K-dependent protein S | Y00692 | P07225 |

For example, it was found that 17 of the genes differentially expressed in human neointima encode transcriptional regulators. mRNA levels for 14 transcription factors were induced in neointima and 3 showed a decreased expression (FIG. 15). Some transcription factors of the former group have previously been related to proliferation and apoptosis of SMCs, such as HMG-1, E2F1, IRF-1, Fli-1, and with pro-inflammatory signaling in human neointima, such as IRF-1, IRF-7 and RelB. The following transcription factors were upregulated: E2F1, estrogen-related receptor alpha, ets domain protein elk-3, fli-1 oncogene, HMG-1, interferon regulatory factor 1, interferon regulatory factor 7, ISGF3-gamma, nuclear receptor-related 1, RELB, transcription factor Spi-B, vav oncogene, v-erbA related protein, vitamin D3 receptor; whereas the following were downregulated: homeobox protein HOXB7, early growth response protein 1, serum response factor.

Striking changes seem to take place in the expression of transcription factors of the Ets family. Whereas Spi-B, the fli-oncogene, and the Ets-repressor Elk-3 were induced in neointima, the Ets transcription factor Egr-1 was repressed (FIGS. 14 and 15).

Furthermore, a number of genes involved in controlling or mediating proliferative responses were differentially expressed between neointima and control groups. The platelet-derived growth factor (PDGF)-A and angiotensinogen genes, whose products act on SMCs as mitogens, were exclusively expressed in neointima (FIG. 14). Angiotensin is known to be upregulated by insulin and to induce the expression of PDGF-A in SMCs. As a sign of ongoing proliferation, several genes known to be expressed with the G1/S transition of the cell cycle were found to be upregulated in neointima. Those include transcription factor E2F1, 70-kDa replication protein A, oncogene product Pim-1 and geranylgeranyl transferase. In addition, upregulation of the cell-cycle regulated histone H4, which is expressed in the G/S1 and S-phase of the cell cycle indicating ongoing proliferation in human neointima, was observed.

Reprogramming of cell growth in neointima evidently led to induction of several genes in neointima encoding proteins with functions in different signal transduction pathways, including the cell surface receptors EDG-1, EDG-4, insulin receptor and P2X purinoceptor 5, and other signaling proteins like the ribosomal protein S6 kinase II alpha 1, farnesyltransferase, phospholipase C beta 2, growth factor receptor-bound protein 2, and the small G proteins CDC42, RhoG, p21-Rac2 and RalB. The enzyme farnesyltransferase catalyzes the essential post-translational lipidation of Ras and several other signal transducing G proteins. G proteins, like p21-Rac2, CDC42 and RhoG play pivotal roles in signal transduction pathways leading to cell migration and cell proliferation. Likewise, agonist-stimulated 1,4,5-triphosphate (IP3) production by phospholipase C beta 2 in smooth muscle requires G protein activation and activated Rac and Cdc42 associate with PI 3 kinase that plays an important role in the activation of the p70 S6 kinase. The p70 S6 kinase (p70S6K) is an important regulator of cell cycle progression to enter G1 phase and to proceed to S phase in response to growth factors and mitogens. It is involved in multiple growth factor related signal transduction pathways that are known to play pivotal roles in neointima formation, like angiotensin, endothelin and PDGF. In line with upregulation of p70 S6 kinase, significant upregulation of the FK506-binding protein (FKBP) 12 at mRNA (FIG. 14) and protein level in neointima was found.

It was observed that a number of genes encoding inhibitors of cell cycle progression were expressed in quiescent media but significantly downregulated in neointima (FIG. 14). Those included CIP1, p16-INK4, metallothionein, TGF-beta3, mammary-derived growth inhibitor, FrzB and the Gadd45 beta and gamma subunits.

Additionally, upregulation of genes in human neointima encoding proteins with pro-apoptotic function, like caspase-1, DAP-1 and APO-2 ligand, as well as upregulation of genes encoding proteins with anti-apoptotic function, like BAG-1, BCL-2-related protein A1 and the Trail receptor 3 (FIG. 14) was found.

Finally, the human neointima transcriptome showed upregulation of 32 genes related to IFN-γ signaling (FIG. 16). The IFN-γ receptor alpha was expressed in neointima, proliferating CASMCs and—to a lesser degree—in blood cells; whereas the IFN-γ receptor beta was mainly expressed in neointima specimen. Likewise, an upregulation of Pyk2 was observed.

Upregulation of the IFN-γ regulated genes for caspase-1, caspase-8 and DAP-1 was found in human neointima. However, mRNAs for the anti-apoptotic proteins BAG-1, Pim-1 (both regulated by IFN-γ) and BCL-2-related protein A1 were also upregulated in neointima versus control (FIG. 14).

Numerous genes with functions in inflammatory responses were found activated in human neointima. Pro-inflammatory gene patterns came from infiltrating inflammatory cells such as macrophages and T lymphocytes (e.g., CD11b, CD3) (FIG. 14C) or from neointimal SMCs (e.g., prostaglandin G/H synthase 1, phospholipase A2, heat shock protein 70, C5a anaphylatoxin receptor, IFN-γ receptor) (FIG. 14A and B).

The selective expression of CD40 in neointima deserves attention (FIG. 14A). CD40 is a member of the TNF receptor family that was initially described on the surface of B cells.

The following cytoskeletal, extracellular matrix and cell adhesion changes in neointima were observed:

An upregulation of connexin43 and of cytokeratin-18 in neointima as is seen in proliferating CASMC (FIG. 14B, upper panel), whereas the expression of desmin was strongly reduced in neointima (FIG. 14D, upper panel).

Whereas the transcription of different collagen subtypes and tenascin were reduced in neointima (FIG. 14D, upper panel), expression of thrombospondin-1 and versican were upregulated (FIG. 14B, upper panel).

A number of genes encoding adhesion molecules, including P-selectin, ICAM2 and cadherin 16, were found highly expressed in neointima but not in SMCs, blood cells or control vessels (FIG. 14A, upper panel). A number of other adhesion molecules were similarly expressed in neointima, cultured SMCs (FIG. 14B) and blood cells (FIG. 14C). Neointima appears to downregulate expression of certain adhesion molecules that are normally expressed in media/intima of arteries, such as integrins α7B, α3 or MUC18.

EXAMPLE VII

Upregulated Genes of the IFN-γ Signaling Pathway

As shown herein above, the expression of 2,435 genes of known function in atherectomy specimen of 10 patients with in-stent restenosis, blood cells of 10 patients, normal coronary artery specimen of 11 donors, and cultured human coronary artery smooth muscle cells was investigated and 224 genes that were differentially expressed with high statistical significance (p<0.03) between neointima and control tissue were identified. In particular, 32 upregulated genes that are related to interferon-γ signaling were identified in neointima.

The IFN-γ receptor alpha was expressed in neointima, proliferating CASMCs and—to a lesser degree—in blood cells; whereas the IFN-γ receptor beta was mainly expressed in neointima specimen.

IFN-γ signals via a high-affinity receptor containing an α- and β-receptor chain. Interstingly, TH1 cells use receptor modification to achieve an IFN-γ-resistant state (Pernis, Science 269 (1995), 245–247). The subtype-specific difference in the activation of the IFN-γ signaling pathway of type 1 and type 2 T helper cells is due to a lack of IFN-γ receptor β in type 1 T cells. Therefore, the here presented data would argue that a high affinity IFN-γ-receptor containing both chains is mainly expressed in smooth muscle cells of the neointima.

Consistent with an activation of IFN-γ signaling, upregulation of two transcription factors in neointima that are essential for IFN signalling were found: IRF-1 and ISGF3γ (p48). These transcription factors are known to be transcriptionally upregulated by IFN-γ (Der, Proc. Natl. Acad. Sci. 95 (1998), 15623–15628), and both are key players in IFN-γ signalling (Matsumoto, Biol. Chem. 380 (1999), 699–703; Kimuar, Genes Cells 1 (1996), 115–124; Kirchhoff, Nucleic Acids Res. 21 (1993), 2881–2889; Kano, Biochem. Biophys. Res. Commun. 257 (1999), 672–677). Likewise, upregulation of the tyrosine kinase Pyk2 was observed, which has been shown to play a role in the signal transduction by angiotensin in SMCs (Sabri, Circ. Res. 83 (1998), 841–851). Pyk2 is selectively activated by IFN-γ and inhibition of Pyk2 in NIH 3T3 cells results in a strong inhibition of the IFN-γ-induced activation of MAPK and STAT1 (Takaoka, EMBO J. 18 (1999), 2480–2488.

A key event in IFN-γ-induced growth inhibition and apoptosis is the induction of caspases (Dai, Blood 93 (1999), 3309–3316). It has been shown that IRF-1 induces expression of caspase-1 leading to apoptosis in vascular SMCs (Horiuchi, Hypertension 33 (1999), 162–166), and that apoptotic SMCs and macrophages colocalize with caspase-1 in atherosclerosis (Geng, Am. J. Pathol. 147 (1995), 251–266). In this studies, upregulation of the IFN-γ-regulated genes for caspase-1, caspase-8 and DAP-1 in human neointima was found. However, mRNAs for the the anti-apoptotic proteins BAG-1, Pim-1 (both regulated by IFN-γ) and BCL-2-related protein A1 were also upregulated in neointima versus control (FIG. 16), supporting the notion that proliferation and apoptosis occur simultaneously in human neointima with a preponderance of proliferation.

Coordinated regulation of genes whose products act at different steps in the neointima process was a recurring theme of our gene expression analysis. Regarding the IFN-γ pathway, not only the genes for the complete receptor, the main transcription factors, components of the signal transduction pathway (Dap-1, BAG-1, Pim-1, IFN-γ-inducible protein, IFN-inducible protein 9-27) were induced but also several target genes of the IFN-γ pathway, like CD40, CD13 and thrombospondin-1 (FIG. 16).

The IFN-γ-regulated gene cluster was expressed in the neointima specimen but some of the relevant genes, like IRF-1, were also expressed in blood samples. To identify the cell type that predominantly contributed to the IFN-γ regulated pattern, frozen sections of neointima specimen from coronary in-stent restenosis (n=3) and from restenosis of peripheral arteries (n=6) were stained with antibodies specific for IRF-1. This protein was chosen because it is an essential component of the IFN-γ signal transduction pathway (Kimura, loc. cit.) and was expressed coordinately with the other genes in the cluster (FIG. 16). Immunohistochemical analysis showed strong nuclear and cytoplasmic staining of IRF-1 in neointimal SMCs of a carotid restenosis (FIG. 17) and of coronary in-stent restenosis (FIG. 18), as identified by their spindle-shaped nuclei and by staining with the smooth muscle cell marker alpha-actin (FIG. 18). The nuclear staining of IRF-1 in in-stent restenosis (FIG. 18) indicated that the IRF-1 transcription factor is also activated. SMCs in control media of carotid arteries did not show IRF-1 staining (FIG. 17). CD3-positive cells were much less abundant in the specimen (FIG. 18) than SMCs (FIG. 18), indicating that SMCs contributed mostly to the increased IRF-1 expression in human neointima.

The presence of IFN-γ in human atherosclerotic lesions is well established (Ross, N. Engl. J. Med. 340 (1999), 115–126) although its role remains unclear. Whereas IFN-γ inhibits proliferation and induces apoptosis in SMCs in vitro (Horiuchi, loc. cit.; Warner, J. Clin. Invest 83 (1989), 1174–1182), absence of IFN-γ reduces intima hyperplasia in mouse models of atheroma and transplant arteriosclerosis (Gupta, J. Clin. Invest 99 (1997), 2752–2761; Raisanen-Sokolowski, Am. J. Pathol. 152 (1998), 359–365). In line with this observation, it was shown that IFN-γ induces arteriosclerosis in absence of leukocytes in pig and human artery tissues by their insertion into the aorta of immuno-deficient mice (Tellides, Nature 403 (2000), 207–211).

The role of infiltrating T lymphocytes in neointima of in-stent restenosis has not been examined yet. In this study it was shown that CD3-positive cells can be detected by immunobiochemists in 3 out of 4 neointima samples (see FIG. 18), and a CD3-specific hybridization signal on cDNA arrays with 7 out of 10 neointima specimen was obtained (FIG. 18). IFN-γ-related expression patterns were also observed in samples negative for CD3 as examined by either method, suggesting that the cytokine could act on neointima in a paracrine fashion over some distance with no need for massive T cell infiltration. While T cells and the pro-inflammatory cytokine IFN-γ are known to play an important role in atherosclerosis (Ross, loc. cit.), their role in the development of neointima is largely unexplored. The here provided data suggest an important role of IFN-γ in the pathophysiology of neointimal hyperplasia.

EXAMPLE VIII

Preparation of a Surrogate Cell Line

A surrogate cell line for a pathologically modified cell and/or tissue may be prepared by the following steps:

a) Definition of the Transcriptome/Gene Expression Pattern of the Diseased Tissue:

Microscopic specimen of diseased tissue may be obtained by either atherectomy, debulking, biopsy, laser dissection of diseased tissue or macroscopic surgical dissection of diseased tissue. After acquisition, microscopic specimen are immediately frozen in liquid nitrogen and kept in liquid nitrogen until mRNA preparation is performed in order to preserve the in vivo status of the samples' transcriptomes.

The cells in such samples express a particular set of genes which is reflected by the presence of distinct mRNA molecules occuring at various concentrations. The entirety of mRNA molecules and their relative amounts in a given clinical sample is referred to as the transcriptome. The transcriptome of a diseased tissue is expected to be different from that of a healthy tissue. The differences relate to the up- or downregulated expression of genes involved in causing, maintaining or indicating the diseased state of the tissue. The analysis of the transcriptome is typically limited by the number of cDNA elements a particular array carries.

mRNA preparation and amplification is carried out according to the method of the invention and described herein above.

In particular, microscopic specimen of diseased tissue are quick-frozen and kept in liquid nitrogen until mRNA preparation and cDNA synthesis is performed as described herein above. Frozen tissue is ground in liquid nitrogen and the frozen powder dissolved in Lysis buffer according to the procedure of RNA preparation. The lysate is centrifuged for 5 min at 10,000 g at 4° to remove cell debris. RNA can be prepared as total RNA or as mRNA as described ein (Schena, Science 270 (1995), 467–470), in Current Protocols, in the Clontech manual for the Atlas cDNA Expression Arrays or as described in (Spirin, Invest. Ophtalmol. Vis. Sci. 40 (1999), 3108–3115), as described in (Chee, Science 274 (1996), 610–614; Alon, Proc. Natl. Acad. Sci. 96 (1999), 6745–6750; Fidanza, Nucleosides Nucleotides 18 (1999), 1293–1295; Mahadevappa, Nat. Biotechnol. 17 (1999), 1134–1136; Lipshutz, Nat. Genet. 21 (1999), 20–24) for the Affymetrix arrays or as described by Qiagen.

cDNA preparation and labeling can be performed-as described by Clontech or Affymetrix in the user's manual for the arrays hybridization kits or as described in (Spirin, loc. cit.; Chee, loc. cit.; Alon, loc. cit.; Fidanza, loc. cit.; Mahadevappa, loc. cit.; Lipshutz, loc. cit.). Additionally, amplified cDNA can be used. Preparation of cDNA amplificates and labeling of amplificated cDNA can be performed as described herein above or by Spirin (loc. cit.).

Obtained, labeled cDNA can be employed in hybridization assays. Hybridization of labeled cDNA and data analysis can be performed under conditions as described in the user's manual from Clontech's Atlas™ cDNA Expression Arrays User Manual or in the manufacter's manual of Affymetrix or as described by (Spirin, loc. cit.; Chee, loc. cit.; Alon, loc. cit.; Fidanza, loc. cit.; Mahadevappa, loc. cit.; Lipshutz, loc. cit.).

b) Definition of the Transcriptome/Gene Expression Pattern of Control Tissue

To identify disease-specific gene expression patterns, the gene expression pattern of the diseased tissue can be compared to control material from healthy donors. In the case of atherectomy material this can be healthy media and intima of non-elastic, i.e., muscular arteries. In the case of heart muscle biopsies or kidney biopsies, healthy control tissue can be used that is collected in the course of the operation. Additionally, gene expression pattern of cells of neighbouring unaffected tissue or of infiltrating cells, like blood, cells can be analyzed. Based upon the celluar characterization of a tissue by immunohistochemical analysis using antibodies to cell marker proteins, transcriptome can be determined from cultured human cell lines of the same type. (Example: arteries stain positive for smooth muscle cells and endothelial cells; consequently transcriptomes are obtained from cultured human smooth muscle and endothelial cells).

mRNA preparation and amplification can be carried out as described herein above and in accordance with the method of the present invention. Obtained (labeled) cDNA may be employed in hybridization assays as described herein above.

c) Determination of a Relevant Set of Disease Specific Genes

To determine disease-specific gene expression patterns first the gene expression pattern of the diseased tissue should be compared to the gene expression pattern of healthy control tissue. For comparison, the mean expression value of at a sufficient number of diseased specimen (e.g., 10) and the same number of control specimen should be compared. Genes with an expression ratio >2.5-fold between the the two groups should be analyzed for their relative expression in one group: there should be >5/10 positive in one group, if there are 0/10 in the other or at least 7/10 in one group if there are maximally 3/10 positive in the other group. Additionally, these data should be analysed statistically to define genes with an $p<0.05$ with e.g. the Wilcoxon test as described in the manual of SPSS 8.0.

Genes selected based upon their significant over- or underexpression by a factor of 2.5 are refered to as aberrantly regulated in the diseased tissue, or as diseases-related genes. Disease-related genes genes are then grouped by the functions of encoded proteins. e.g. genes encoding proteins of the signalling pathway, cytokines, chemokines, hormones, their receptors, proteins specific or infiltrating cells, or proteins involved in extracellular matrix, cell adhesion, migration, cell division, cell cycle arrest. Likewise genes of unknown function, as available thorugh public EST data bases, can be identified as being disease-related.

d) Screen for a Cell Line with a Transcriptome Most Closely Resembling that of Diseased Tissue Drugs that can potentially regulate the expression of diseased genes can be discovered by screening large libraries of chemicals or biologics. In order to identify such drugs, a screening cell line must be available that faithfully reflects the transcriptome of the diseased tissue and is avaiabale in large quantaties for the performance of a comprehensive drug screen. Moreover information is needed of how the drug candidate should alter the transcriptome of the cell line that has characteristics of the transcriptome of the diseased tissue. This information is obtained from the transcriptome of the healthy control tissue. The drug should be able to re-estsblish features of a "healthy" transcriptome.

A human cell line, which is most similiar to the cellular origin of the diseased tissue, e.g, coronary artery smooth muscle cells for atherectomy, HepG2 cells for liver diseases, renal cells for kidney diseases or cardiomyoblasts for heart muscle disease should be used. Cells should be grown under standard conditions as described in the manufacter's manual like the ones from ATCC.

Transcriptome analysis/gene expression pattern analysis can be performed as described for the diseased and the control tissue and gene expression pattern should be compared to the gene expression pattern of the diseased and the healthy tissue. For generating a surrogate screening cell line, the cell line which shows a transcriptome most similar to the diseased transcriptome should be selected.

e) Adaptation of a Cell Line to Mimick Diseased Transcriptome/Gene Expression Pattern In order to generate a surrogate screening cell line for the diseased tissue, it may be necessary to adapt the transcriptome of the selected cell line to the transcriptome of the diseased tissue. This can on the one hand be achieved by incubation of the cell line with compounds such as cytokines or hormones, that had been shown to play an important role in the gene expression pattern of the diseased tissue. Likewise such compounds can be identified by transcriptome analysis of diseased tissue as exemplified with neoinitima where evidence for a role of interferon-gamma was obtained. Instead of addition of compounds with relevance for the disease, the screening cell line can be conditioned by co-culture with other cell types relevant for the pathophysiology of the disease. Such cells can for instance be inflammatory cells, like macrophages or T cells, that migrate into the diseased tissue and by released factors or cell-cellcontact contribute to the disease-specific gene expression pattern. In each case, transcriptome analysis of the surrogate line must identify the optimal addition to generate a disease-specific expression pattern.

Compounds that can be used for adapting the transcriptome of a surogate cell line to the diseased state comprise cytokines, growth factors, small molecule compounds (drugs), or peptides and peptidomimetics. Cell lines that can be used for such an adaptation comprise human monocytic cell lines, like U937, THP-1 or Monomac-6, or human T-cell lines like Jurkat.

The co-culture/treatment conditions leading in the surrogate cell line to a state closest to the diseased transcriptome are selected for drug screening.

In the following, a specific example should illustrate the preparation of a surrogate. In particular, a surrogate cell (line) for restenotic tissue is prepared by the following steps:

a) Aquisition of In-stent Restenotic Tissue

Patients

The in-stent restenosis study group consisted of 13 patients who underwent separate atherectomy procedures by X-sizer within the renarrowed stent between 4–23 month after primary stent implantation. All patients gave informed consent to the procedure and received 15,000 units heparin before the intervention followed by intravenous heparin infusion, 1,000 units/h for the first 12 h after sheat removal as standard therapy. All patients received aspirin, 500 mg intravenously, before catherisation, and postinterventional antithrombotic therapy consisted of Aticlopidine (250 mg bds) and aspirin (100 mg bds) throughout the study.

Sample Preparation

Atherectomy specimen were immediately frozen in liquid nitrogen after debulking of the lesion, and kept in liquid nitrogen until mRNA preparation was performed as described. For histology and immunhistochemistry of the in-stent restenotic tissue from coronary arteries (n=3), the samples were fixed in 4% paraformaldehyd and embedded in paraffin as described.

Morphological Characterization of Restenotic Tissue

Immunohistochemistry for cell typing was performed on paraffin-embedded sections of three neointima specimen from coronary in-stent restenosis and, for detection of FKBP12, on frozen sections of four neointima specimen from carotid restenosis. Three μm serial sections were mounted onto DAKO ChemMate™ Capillary Gap Microscope slides (100 μm) baked at 65° C. overnight, deparaffinized and dehydrated according to standard protocols. For antigen retrieval, specimens were boiled 4 min in a pressure cooker in citrate buffer (10 mM, pH 6.0). Endogenous peroxidase was blocked by 1% H2O2/methanol for 15 minutes. Unspecific binding of the primary antibody was reduced by pre-incubation of the slides with 4% dried skim milk in Antibody Diluent (DAKO, Denmark). Immunostaining was performed by the streptavidin-peroxidase technique using the ChemMate Detection Kit HRP/Red Rabbit/Mouse (DAKO, Denmark) according to the manufacturer's description. The procedures were carried out in a DAKO TechMate™ 500 Plus automated staining system. Primary antibodies against smooth muscle actin (M0635, DAKO, Denmark; 1:300), CD3 (A0452, DAKO, Denmark; 1:80), MAC387 (E026, Camon, Germany; 1:20) and FKBP12 (SA-218, Biomol, Germany, 1:20) were diluted in Antibody Diluent and incubated for 1 h at room temperature. After nuclear counterstaining with hematoxylin, the slides were dehydrated and coverslipped with Pertex (Medite, Germany).

The Cellular Composition of Debulked In-stent Restenotic Material

Representative samples obtained from x-sizer treatment of a neointimal hyperplasia were analyzed by immunhistochemistry in order to determine its cellular composition. FIG. 7A shows an E.-van-Giesson staining of a section cut from a small sample of debulked restenotic material. With this staining procedure, collagen fibers stain red, fibrin stains yellow and cytoplasm of smooth muscle cells stains dark-yellow-brown. The majority of the volume of debulked material was composed of loose extracellular matrix-like collagen fibers stained in light red. Yellow fibrin staining was barely detectable. Cells with spindle-shaped nuclei and a yellow/brown-stained cytoplasm were frequent. Their identity as smooth muscle cells and their high abundance in restenotic material was supported by immunostaining with an antibody against smooth muscle α-actin (FIG. 7B). There, the staining pattern of a section from an entire specimen as used for gene expression analysis is shown. As described below, such samples also gave raise to a strong smooth muscle-specific α-actin mRNA signal (see FIG. 8). These results support findings from previous studies (Kearney, Circulation 95 (1997), 1998–2002; Komatsu, Circulation 98 (1998), 224–233; Strauss, J. Am. Coll. Cardiol. 20 (1992), 1465–1473) demonstrating that the main cell type found in neointima is derived from smooth muscle cells. As described in the literature (Kearney, loc. cit.; Komatsu, loc. cit.; Strauss, loc. cit.) mononuclear infiltrates could also be identified in some areas of debulked restenotic tissue specimen. These infiltrates consisted mainly of macrophages and to a lesser degree of t-lymphocytes. No b-lymphocytes were detectable in the restenotic tissue by using an antibody against CD20 for immunhistochemical staining.

b) Transcriptome Analysis of Restenotic Material

Transcriptome analysis of neointima was performed using the method of mRNA amplification as described herein above.

mRNA Preparation

Microscopic specimen diseased tissue were quick-frozen and kept in liquid nitrogen until mRNA preparation and cDNA synthesis was performed. Frozen tissue is ground in liquid nitrogen and the frozen powder dissolved in Lysis/Binding buffer (100 mM Tris-HCl, pH 7.5, 500 mM LiCl, 10 mM EDTA, pH 8.0, 1% LiDS, 5 mM dithiothreitol (DTT)) and homogenized until complete lysis is obtained. The lysate is centrifuged for 5 min at 10,000 g at 4° to remove cell debris. mRNA is prepared using the Dynbeads® mRNA Direct Kit™ (Dynal, Germany) following the manufacture's recommendation. Briefly, lysate was added to 50 μL of pre-washed Dynabeads Oligo (dT)25 per sample and mRNA was annealed by rotating on a mixer for 30 min at 4° C. Supernatant was removed and Dynabeads Oligo (dT)25/mRNA complex was washed twice with washing buffer containing Igepal (50 mM Tris-HCl, pH 8.0, 75 mM KCl, 10 mM DTT, 025% Igepal), and once with washing buffer containing Tween-20 (50 mM Tris-HCl, pH 8.0, 75 mM KCl, 10 mM DTT, 0.5% Tween-20).

Preparation of Amplified cDNA cDNA is amplified by PCR using the procedure of Klein et al. (C. Klein et al.). First-strand cDNA synthesis is performed as solid-phase cDNA synthesis. Random priming with hexanucleotide primers is used for reverse transcription reaction. mRNAs are each reversely transcribed in a 20 μL reaction volume containing 1× First Strand Buffer (Gibco), 0.01 M DTT (Gibco), 0.25% Igepal, 50 μM CFL5c-Primer (SEQ ID NO:8) [5'-(CCC)5 GTC TAG A (NNN)2-3'], 0.5 mM dNTPs each (MBI Fermentas) and 200 U Superscript II (Gibco), and incubate at 44° C. for 45 mm. A subsequent tailing reaction is performed in a reaction volume of 10 μL containing 4 mM MgCl2, 0.1 mM DTT, 0.2 mM dGTP, 10 mM KH2PO4 and 10 U of terminal deoxynucleotide transferase (MBI Fermentas). The mixture is incubated for 24 mm at 37° C.

cDNA is amplified by PCR in a reaction volume of 50 μL containing 1× buffer 1 (Expand™ Long Template PCR Kit, Boehringer Mannheim), 3% deionized formamide, 120 μM CP2-Primer (SEQ ID NO:14) [5'-TCA GAA TTC ATG (CCC)5-3'], 350 μM dNTP and 4.5 U DNA-Polymerase-Mix (Expand™ Long Template PCR Kit, Roche Diagnostics, Manuhein). PCR reaction is performed for 20 cycles with the following cycle parameters: 94° C. for 15 sec, 65° C. for 0:30 min, 68° C. for 2 min; for another 20 cycles with: 94° C. for 15 sec, 65° C. for 30 sec, 68° C. for 2:30+0:10/cycle min; 68° C. 7 min; 4° C. forever.

Expression of Specific Genes in Microscopic Human Tissue Samples

In order to optimally preserve the in situ mRNA levels, restenotic and control specimen were immediately frozen after harvest in liquid nitrogen and carefully lyzed as described in Materials and Methods. After PCR amplification of the synthesized cDNA the amount of the amplified cDNA was measured by a dot blot assay and found to be between 200–300 ng/μl. The quality of every amplified cDNA sample was tested by gene-specific PCR using primers detecting cDNAs for β-actin, smooth muscle cell α-actin and the ubiquitous elongation factor EF-1α. FIG. 8 shows a representative result with material from patient B and control media from donor b. In both specimen, PCR signals of the correct size from house-keeping genes β-actin and EF-1α were detectable in equivalent amounts (compare lanes 1 and 2 with lanes 4 and 5). Additionally, α-actin signals as marker for smooth muscle cells was obatined from each specimen (lanes 3 and 6). These results show that mRNA prepraration, cDNA synthesis and PCR amplification of cDNA is feasible with microscopic human restenosis samples.

Dig-dUTP Lab ling of cDNA Probes 25 ng of each cDNA is labeled with Digoxigenin-11-dUTP (Dig-dUTP) (Roche Diagnostics) during PCR. PCR is performed in a 50 μL reaction with 1× Puffer 1, 120 μM CP2 primer, 3% deionized formamide, 300 μM dTTP, 350 μM dATP, 350 μM dGTP, 350 μM dCTP, 50 μM Dig-dUTP, 4.5 U DNA-Polymerase-Mix. Cycle parameters are: one cycle: 94° C. for 2 min; 15 cycles: 94° C. for 15 sec, 63° C. for 15 sec, 68° C. for 2 min; 10 cycles: 94° C. for 15 sec, 68° C. for 3 min+5 sec/cycle; one cycle: 68° C., 7 min, 4° C. forever.

Hybridization of Clontech cDNA Arrays with dUTP-labeled cDNA Probes cDNA arrays are prehybridized in DigEASYHyb solution (Roche Diagnostics) containing 50 mg/L DNAseI (Roche Diagnostics) digested genomic E. coli DNA, 50 mg/L pBluescript plasmid DNA and 15 mg/L herring sperm DNA (Life Technologies) for 12 h at 44° C. to reduce background by blocking non-specific nucleic acid-binding sites on the membrane. Hybridization solution is hybridized to commercially available cDNA arrays with selected genes relevant for cancer, cardiovascular and stress response (Clontech). Each cDNA template is denatured and added to the prehybridization solution at a concentration of 5 μg/ml Dig-dUTP-labeled cDNA. Hybridization was performed for 48 hours at 44° C.

Blots are subsequently rinsed once in 2×SSC/0.1% SDS and once in 1×SSC/0.1% SDS at 68° C. followed by washing for 15 min once in 0.5×SSC/0.1% SDS and twice for 30 min in 0.1×SSC/0.1% SDS at 68° C. For detection of Dig-labeled cDNA hybridized to the array, the Dig Luminescent Detection Kit (Boehringer, Mannheim) was used as described in the user manual. For detection of the chemiluminescence signal, arrays are exposed to chemiluminescence films for 30 min at room temperature. Quantification of array data was performed by scanning of the films and analysis with array vision software (Imaging Research Inc., St. Catharines, Canada). Background was subtracted and signals were normalized to the nine housekeeping genes present on each filter, whereby the average of the housekeeping gene expression signals was set to 1 and the background set to 0.

Each labeled probe was hybridized to three different commercial cDNA arrays which allowed for the expression analysis of a total of 2,435 known genes. FIG. 9 shows a representative hybridization pattern obtained with one array using probes prepared from restenotic tissue of patient B (panel A) and media of donor b (panel B). Consistent with the gene-specific analysis shown in FIG. 8, comparable hybridization signals were obtained with the positive control of human genomic cDNA spotted on the right and bottom lanes of the array and with cDNA spots of various housekeeping genes (see for instance, spots D). If a biological specimen was omitted from cDNA synthesis and PCR amplification reactions almost no hybridization signals were obtained (FIG. 9, panel C), showing that hybridization signals were almost exclusively derived from added samples and not from DNA contaminations in reagents or materials used.

Data Analysis

Quantification of array data was performed by scanning of the films and analysis with array vision software (Imaging Research Inc., St. Catharines, Canada). Background was subtracted and signals were normalized to the nine housekeeping genes present on each filter, whereby the average of the housekeeping gene expression signals was set to 1 and the background set to 0. For the logarithmic presentation shown in FIGS. 13A and 13B, values were multiplied by 1000. A mean value >0,05 in the average of all samples in one group was regarded as a positive signal. Differences in the mean expression level by a factor >2.5-fold between the study and the control group were further statistically analyzed.

c) Choice of Control Tissue

As the main cellular component of neointima consists of smooth muscle cells, media and media/intima were taken of healthy coronary arteries or as coronary arteries belong to the non-elastic but muscular arteries muscular arteries as control tissue.

The control group consisted of 6 specimen from coronary arteries from three different patients who underwent heart transplantation. Additionally, 5 specimen of muscular arteries of the gastrointestinal tract from five different patients were taken as control because coronary arteries belong histologically to muscular arteries. The control specimen were immediately frozen in liquid nitrogen. Prior to mRNA preparation, media and intima of the control arteries were prepared and examined for atherosclerotic changes by immunhistochemistry. If there were no atherosclerotic changes of the vessel morphology, the specimen (approx. 1×1 mm) were used as healthy control samples and mRNA and cDNA preparation and transcriptome analysis was performed as described above for neointimal tissue.

d) Definition of the Neointima-specific Gene Expression Profile

A total of 1,186 genes (48.7%) out of 2,435 yielded detectable hybridization signals on cDNA arrays with neointima and control samples over a 20-fold range of expression level (FIG. 13A) Thereof 352 genes (14.5%) appeared to be differentially expressed by a factor >2.5-fold between restenotic and control samples. However, expression levels considerably varied among individual samples (see, e.g., FIG. 9). A statistical analysis was therefore employed in order to identify those genes that are differentially expressed between study and control groups with high significance (see herein above). This way, 224 genes (9.6%) were identified that were differentially expressed by a factor of at least 2.5-fold between the restenosis study group and the control group with a significance in the Wilcoxon test of p<0.03. 167 (75%) genes thereof were found overexpressed and 56 genes (25%) underexpressed in the restenosis study group compared to the control group (FIG. 13B).

) Choice of Surrogate Cell Line

Human neointima consists of a heterogenous cell population. It was therefore attempted to relate the differential, statistically relevant gene expression patterns found with neointima to patterns eventually contributed by peripheral blood cells of the patients and cultured human CASMCs, i.e., cells that are most frequently encountered in restenotic tissue(Komatsu, loc. cit.). With respect to neointima expression, the 224 aberrantly regulated genes fell into four subgroups (FIG. 14). Group I lists 62 genes that were overexpressed in neointima and not highly or detectably expressed in control vessels, CASMCs or blood cells (FIG. 14A). In group II, 43 genes are listed that are similarly expressed in neointima and CASMCs, suggesting that this gene cluster in neointima was contributed by proliferating SMCs (FIG. 5B). In group III, 62 genes are listed that are similarly expressed in neointima and blood cells, suggesting that this gene cluster was contributed to that of neointima by infiltrated blood cells (FIG. 14C). This notion is supported by the expression in group III of the largest number of genes related to inflammation in all four groups. Lastly, in group IV, 56 genes are listed that are downregulated in neointima compared to the control group (FIG. 14D).

Upregulation of γ-IFN-related Genes in Neointima

A surprising feature of the human neointima transcriptome was the apparently coordinate upregulation of 32 genes related to IFN-γ signaling (FIG. 16). The IFN-γ receptor alpha was expressed in neointima, proliferating CASMCs and—to a lesser degree—in blood cells; whereas the IFN-γ receptor beta was mainly expressed in neointima specimen. Consistent with an activation of IFN-γ signaling, upregulation of two transcription factors in neointima was found that are essential for IFN signalling: IRF-1 and ISGF3γ (p48) (FIGS. 14, 15, 16). These transcription factors are known to be transcriptionally upregulated by IFN-γ, and both are key players in IFN-γ signalling. Likewise, upregulation of the tyrosine kinase was observed Pyk2 (FIG. 16), which has been shown to play a role in the signal transduction by angiotensin in SMCs (Sabri, Circ. Res. 83 (1998), 841–851). Pyk2 is selectively activated by IFN-γ and inhibition of Pyk2 in NIH 3T3 cells results in a strong inhibition of the IFN-γ-induced activation of MAPK and STAT1. A key event in IFN-γ-induced growth inhibition and apoptosis is the induction of caspases (Dai, Blood 93 (1999), 3309–3316). In the here presented analysis on upregulation of the IFN-γ-regulated genes for caspase-1, caspase-8 and DAP-1 in human neointima. However, mRNAs for the the anti-apoptotic proteins BAG-1, Pim-1 (both regulated by IFN-γ) and BCL-2-related protein A1 were also upregulated in neointima versus control (FIG. 16), supporting the notion that proliferation and apoptosis occur simultaneously in human neointima with a preponderance of proliferation.

Coordinated regulation of genes whose products act at different steps in the neointima process was a recurring theme of our gene expression analysis. Regarding the IFN-γ pathway, not only the genes for the complete receptor, the main transcription factors, components of the signal transduction pathway (Dap-1, BAG-1, Pim-1, IFN-γ-inducible protein, IFN-inducible protein 9–27) were induced but also several target genes of the IFN-γ pathway, like CD40, CD13 and thrombospondin-1 (FIG. 16).

The IFN-γ-regulated gene cluster was expressed in the neointima specimen but some of the relevant genes, like IRF-1, were also expressed in blood samples. To identify the cell type that predominantly contributed to the IFN-γ regulated pattern, frozen sections of neointima specimen from coronary in-stent restenosis (n=3) and from restenosis of peripheral arteries (n=6) were stained with antibodies specific for IRF-1. This protein was chosen because it is an essential component of the IFN-γ signal transduction pathway (Kimura, Genes Cells 1 (1996), 115–124) and was expressed coordinately with the other genes in the cluster (FIG. 17). Immunohistochemical analysis showed strong nuclear and cytoplasmic staining of IRF-1 in neointimal SMCs of a carotid restenosis (FIG. 17B) and of coronary in-stent restenosis (FIG. 18C), as identified by their spindle-shaped nuclei and by staining with the smooth muscle cell marker alpha-actin (FIG. 18B). The nuclear staining of IRF-1 in in-stent restenosis (FIG. 18C) indicated that the IRF-1 transcription factor is also activated. SMCs in control media of carotid arteries did not show IRF-1 staining (FIG. 17B). CD3-positive cells were much less abundant in the specimen (FIG. 18C) than SMCs (FIG. 18D), indicating that SMCs contributed mostly to the increased IRF-1 expression in human neointima.

Definition of Culturing Conditions in Order to Adapt Transcriptome Profile to that of Restenotic Tissue: IFN-γ

To adapt the transcriptional profile of cultured human coronary artery smooth muscle cells (CASMC) (Clonetics) to that of neointima, CASMC were stimulated with IFN-g and performed transcriptome analysis as described above. CASMC were cultured as described in the manufacter's manual in growth medium until 50% confluency was reached. Afterwards cells were stimulated with 1000 U/ml IFN-γ (R&D, Germany) for 16 hours at 37° C. Cells were washed twice in PBS and RNA preparation, cDNA synthesis and amplification and transcriptome analysis was performed as described above.

As shown in FIG. 19 the neointima-specific IFN-γ gene expression pattern could be generated by incubation of CASMCs with 1000 U/ml IFN-γ.

Definition of the Transcriptome/gene Expression Pattern of Neointima after Incubation with an IFN-γ Antagonist Microscopic specimen of in-stent restenotic tissue were incubated with an antagonist for IFN-γ for different times and transcriptome analysis was performed as described. Transcriptome of treated neointima was compared to the transcriptome of untreated neointima and healthy control tissue, to measured the therapeutic effect of IFN-γ antagonists.

Definition of th Transcriptom/gene Expression Pattern of Neointima after Incubation with Rapamycin It has been shown in the literature, that rapamycin, a ligand of the intracellular protein FKBP12 inhibits migration and proliferation of smooth muscle cells and is able to reduce neointimal hyperplasia in a porcine model of restenosis. As significant upregulation of FKBP12 in the neointima specific transcriptome was found in order to evaluated the therapeutic effect of rapamycin.

As proliferating CASMC overexpress FKBP12 like neointima, this cell line can be employed as a potential surrogate cell line for neointima in respect to therapeutic effects of rapamycin. Therefore, in a first step, CASMC were incubated with 100 ng/ml rapamycin (Sigma) for 24 hours and transcriptome analysis was performed in order to monitore the therapeutic effect. Afterwards, microscopic specimen of in-stent restenotic tissue are incubated with rapamycin and transcriptome analysis was performed as described herein above. Transcriptome/gene expression pattern of rapamycin treated CASMC was compared to the transcriptome of rapamycin-treated neointima to measured the effectiveness of CASMC as a surrogate cell line for neointima. Tumorsuppressor genes and proliferation-inhibiting genes have upregulated in said CASMCs; therefore said CASMCs can be considered as an true surrogate for neointima.

EXAMPLE IX

Upregulated Protein Expression of Emmprin and Transferrin Receptor on Tumor Cells Transcriptome analysis of single micrometastatic cells derived from patients with different tumor and disease stages revealed an upregulated expression of genes involved in cell cycle regulation, cytoskeleton organization, adhesion and proteolytic activity. Enhanced mRNA expression of Emmprin was found by array hybridization in 10 of 26 micrometastatic cells from bone marrow of breast and prostate cancer patients indicating an invasive phenotype of these cells. EMMPRIN (extracellular matrix metalloproteinase inducer, CD147) is a member of the immunoglobulin superfamily that is present on the surface of tumor cells and stimulates adjacent fibroblasts to produce matrix metalloproteinases (MMPs, Guo, J. Biol. Chem. 272 (1997), 24–27 and Sameshima, Cancer Lett. 157 (2000), 177–184 and Li, J. Cell Physiol. 186 (2001), 371–379). The results were controlled by gene specific PCR revealing a similar sensitivity compared to array hybridization. Using a different Emmprin-specific probe for array hybridization, the Emmprin message was even detected in 16/26 (61%) samples. These results emphasize the sensitivity of the array design to detect the transcripts of a random primed single cell cDNA.

In order to correlate upregulation of Emmprin expression on tumor cells not only on mRNA but also on protein level, slides were prepared from bone marrow cells of cancer patients as described before (Pantel, Lancet 347 (1996), 649–653). Slides were blocked using 10% human AB serum in PBS for 20 min. From each sample one million bone marrow cells were screened for the presence of cytokeratin positive cells which is a marker for epithelial cells. A double staining procedure, employing the EMMPRIN specific antibody MEM 6/2 (Koch, Int. Immunol. 11 (1999), 777–86) and a biotin-conjugated A45B/B3 antibody reacting with several cytokeratin family members was performed. Antibody incubations were as follows: MEM 6/2, 45 min. 5 µg/ml; Z259 and APAAP complex according to the manufacturer's instructions (DAKO). Slides were washed 3×3 min. in PBS between all antibody incubations. Before the A45 B/B3-biotin F (ab)$_2$-fragment was added, an additional blocking step with 10% mouse serum in PBS was performed for 20 min. The A45 B/B3-biotin conjugate (2 µg/ml; 45 min.) was detected by streptavidin-Cy3 (1.2 µg/ml; 15 min; Jackson laboratories). After washing, FAST-BLUE (Sigma) was used as substrate for the alkaline phosphatase (10–30 min). For all slides the procedure was identically performed with isotype controls. EMMPRIN was detected on 82% of 140 cytokeratin-positive tumor cells derived from 68 patients with breast, prostate and lung cancer (Tab. 8 and FIG. 20). In only two aspirates all detected cytokeratin-positive cells (n=4) were negative for EMMPRIN.

TABLE 8

EMMPRIN (EMM) protein expression on disseminated cytokeratin-positive (CK+) tumor cells in bone marrow.

| Number of patients | number of patients with CK+ cells | Total number of CK+ cells | CK+/EMM+ cells | Number of patients with double positive cells |
|---|---|---|---|---|
| 68 | 11/68 (16%) | 140 | 115/140 (82%) | 9/11 (82%) |

Besides Emmprin also expression of transferrin receptor (CD71) on tumor cells was evaluated on protein level. Transcriptome analysis of six small biopsies derived from non-small cell lung cancers and five biopsies of control mucosa from patients with chronic obstructive pulmonary showed that signal intensity for CD71 differed greatly between normal and tumor tissue (Table 9).

TABLE 9

Signal intensities for the transferrin receptor cDNA on array hybridisation

| Tumor biopsies | | | | | | Normal Mucosa biopsies | | | | |
|---|---|---|---|---|---|---|---|---|---|---|
| Bio6 | Bio9 | Bio10 | Bio11 | Bio1G | Bio11G | Bio2 | Bio3G | Bio5G | Bio6G | Bio14 |
| 0 | 2464 | 11768 | 4012 | 0 | 5496 | 0 | 0 | 0 | 100 | 0 |

Differential expression was tested on cryosection of tumor biopsy Bio10 and a biopsy from normal mucosa (Bio6G). Unspecific binding was blocked with 10% AB serum in PBS for 20 minutes and incubation with CD71-PE (phycoerythrin) conjugated antibody (Caltag) was performed for 45 minutes. For control an anti-CD4-PE antibody was used. No staining of the CD4 antibody was observed on either tissue sample. The CD71-PE antibody selectively stained the epithelial regions of the tumor biopsy whereas the normal mucosa was negative for transferrin receptor expression (FIG. 21).

EXAMPLE X

Anti-apoptotic Effect of IFNγ on Smooth Muscle Cells

The effect of IFNγ on the survival of cultured proliferating SMCs was analyzed by flow cytometry. For this reason primary human coronary smooth muscle cells were obtained from CellSystems (Germany) and were grown in Smooth muscle cell growth medium (CellSystems) containing 5% fetal calf serum (CellSystems) at 37° C. in a humidified atmosphere of 5% $CO_2$. SMCs were used between passages 2 and 4. Treatment with 1000U/ml rh-IFNγ (R&D Systems) was performed for 16 h. For induction of cell death, SMCs were incubated at 37° C. for 1 h in HBSS containing 100 μmol/l $H_2O_2$ and 100 □mmol/l ferrous sulfate. Afterwards the cells were further cultured in freshly prepared culture medium for 8 h. Cells were labelled with FITC-labelled Annexin V (Roche Diagnostics) and propidium iodide (PI) according to the manufacturer's instructions. $10^4$ events were analyzed with a flow cytometer (Becton Dickinson).

Flow cytometric analysis revealed an anti-apoptotic effect of IFNγ on SMCs (FIG. 22). FACS analysis after double staining with PI and FITC-labeled Annexin V and showed a reduction of spontaneous apoptosis from 10% to 6% after treatment with IFNγ. The effect became more prominent after induction of apoptosis in SMCs with $H_2O_2$. Treatment with IFNγ reduced the number of apoptotic cells from 54% to 27%. These results clearly show that IFNγ exerts an anti-apoptotic effect on SMCs.

EXAMPLE XI

Inhibitory Effect of IFNγ on Neointima Formation in a Mouse Model for Restenosis To examine the vascular proliferative remodeling after carotid ligation, the mouse blood flow cessation model (Kumar, Circulation 96 (1997), 4333–4342) was used. This model is characterized by vascular proliferation of SMCs in response to ligation of the common carotid artery near bifurcation. In order to investigate the effect of an IFN-γ receptor null mutation on the development of neointima in a mouse model of restenosis IFN-γR$^{-/-}$ knockout mice were used. Adult male 129/svJ mice (N=16) and IFN-γR$^{-/-}$ mice (n=11) were anaesthetized by intraperitoneal injection of a solution of xylazine (5 mg/kg body weight) and ketamine (80 mg/kg body weight) and the left common carotid artery was ligated near bifurcation. After 4 week animals were reanaesthetized, sacrificied and fixed for 3 min by perfusion with 4% paraformaldehyde in 0.1 mol/l sodium phosphate buffer (pH 7.3,). After excision of the left carotid arteries, vessels were fixed by immersion in 70% ethanol. Carotid arteries were embedded in paraffin and serial sections (% μm thick) were cut.

Morphometric analysis was performed on v.-Giesson stained cross sections at a distance of 600 μm from the ligation site. Digitized images of the vessels were analyzed using the image analysis software SCION image 4.0.2. Media thickness was obtained as the differences in diameter between the external and internal elastic lamina, and neointima thickness as the difference between internal elastic lamina and lumen diameter. Data from morphometric analyses are reported as mean±SEM for the two groups of mice and tested by the t-test for unpaired samples. A p value <0.05 was regarded as significant. All analyses were performed with the use of the SPSS statistical package (version 8.0).

Substantial wall thickening due to media proliferation and neointima formation was observed in 16 wild-type mice at 4 weeks after ligation (FIG. 23). In 11 IFN-γR$^{-/-}$ mice medial plus neointimal thickening was significantly reduced shown as mean±SEM and analyzed by the t-test for unpaired samples. Corresponding to the reduction in proliferative responses, 11 IFN-γR$^{-/-}$ mice had a significantly larger lumen diameter of the treated carotid segment than wild-type mice (108±15 um versus 91±24 um and p=0.033).

EXAMPLE XII

Suppression Subtractive Hybridization (SSH) Analysis

SSH is a new and highly effective method for the generation of subtracted cDNA libraries. Subtractive cDNA hybridization has been a powerful approach to identify and isolate cDNAs of differentially expressed genes (Duguin Nucl. Acid. Res. 18 (1990), 2789–2792 and Hara Nucl. Acid. Res. 19 (1991), 7097–7104 and Hendrick Nature (London) 308 (1984), 149–153). In general, hybridization of cDNA from one population (tester) to an excess of mRNA (cDNA) from another population (driver) and subsequent separation of the unhybridized fraction (target) from the hybridized common sequences are performed. SSH is used to selectively amplify target cDNA fragments (differentially expressed) and simultaneously suppress nontarget DNA amplification. The method is based on suppression PCR: long inverted terminal repeats when attached to DNA fragments can selectively suppress amplification of undesirable sequences in PCR procedure. The problem of differences in mRNA abundance is overcome by a hybridization step that equalizes sequence abundance during the course of subtraction. One subtractive hybridization round is required leading to a 1000 fold enrichment for differentially expressed cDNAs (for review see Diatchenko Proc. Natl. Acad. Sci. USA 93 (1996), 6025–30 and Diatchenko Methods Enzymol. 303 (1999), 349–80).

Serveral modifications were introduced into the standard SSH protocol for differential gene expression analysis of a very small number of cells (FIG. 24). 1) mRNA amplificates generated according to the method described in this patent application had been reverse-transcribed and amplified using CP2 primers; 2) mRNA amplificates generated according to the method described in this patent application themselves form panlike structures; 3) introduction of a restriction enzyme recognition site (e.g. EcoRI) into the CP2 primer.

a) Materials and Methods

```
Oligonucleotides cDNA synthesis primer:
CP2:         5'-TCA GAA TTC ATG CCC CCC CCC CCC CCC C-3'           (SEQ ID NO: 14)

Adapters

Adapter 1 (A1)
Eco 44 I:    5'-GTA ATA CGA CTC ACT ATA GGG CTC GAG CGG CTC GCC CGG GCA GG-3'  (SEQ ID NO: 31)

Eco 12 I:    5'-AAT TCC TGC CCG-3'                                  (SEQ ID NO: 32)

Adapter 2 (A2)
Eco 43 II:   5'-TGT AGC GTG AAG ACG ACA GAA AGG TCG CGT GGT GCG GAG GGC G-3'   (SEQ ID NO: 33)

Eco 12 II:   5'-AAT TCG CCC TCC-3'                                  (SEQ ID NO: 34)

PCR Primers:

P1-30:       5'-GTA ATA CGA CTC ACT ATA GGG CTC GAG CGG-3'          (SEQ ID NO: 35)

P2-30:       5'-TGT AGC GTG AAG ACG ACA GAA AGG TCG CGT-3'          (SEQ ID NO: 36)

P1-33:       5'-GTA ATA CGA CTC ACT ATA GGG CTC GAG CGG CTC-3'      (SEQ ID NO: 37)

P2-33:       5'-TGT AGC GTG AAG ACG ACA GAA AGG TCG CGT GGT-3'      (SEQ ID NO: 38)

PN1-30:      5'-CGA CTC ACT ATA GGG CTC GAG CGG CTC GCC-3'          (SEQ ID NO: 39)

PN2-30:      5'-GTG AAG ACG ACA GAA AGG TCG CGT GGT GCG-3'          (SEQ ID NO: 40)
```

Driver Preparation

For detection of transcripts differentially expressed in micrometastatic tumor cells compared to normal bone marrow cells, driver was prepared from bone marrow samples derived from healthy donors. From three bone marrow donors, total RNA was isolated using standard protocols. RNA corresponding to 300.000 bone marrow cells was then added to 30 μl Dynal beads and the protocol of mRNA amplification was performed.

Hybridization kinetics were improved by digestion of 5 μg driver with 50 units of restriction enzyme Rsa I in a 50 μl reaction containing 0,75× buffer NEB1 (New England Biolabs) for 90 min. The sample was desalted with a Microcon 10 column (Millipore).

Tester Preparation

Eco RI digested tester was prepared in 50 μl using 50 U EcoRI. As tester a mixture of four single cells isolated from four different breast cancer patients was selected. After digestion with EcoRI the tester was diluted to a 100 ng/μl concentration in water. Subsequently, one probe was ligated to 5 μl of adapter A1 (SEQ ID NO: 31, SEQ ID NO: 32) and one to adapter A2 (SEQ ID NO: 33, SEQ ID NO: 34) (50 μM) in two independent 10 μl ligation reactions at 15° C. overnight, using 5 units of T4 DNA ligase (Roche). The ligation reaction was inactivated by addition of 2 μl 0.1 M EDTA and heating 5 min at 70° C.

Subtractive Hybridization

1 μl of driver (500 ng) was added to each of two tubes containing 2 μl of tester cDNA (about 18 ng) ligated to adapter A1 (SEQ ID NO: 31, SEQ ID NO: 32) and ligated to adapter A2 (SEQ ID NO: 33, SEQ ID NO: 34) in hybridization buffer (1 M NaCl, 50 mM Hepes, 1 mM CTAB). The solution was overlaid with mineral oil, denatured 1 min at 98° C. and then allowed to anneal for 10–14 hours at 68° C.

After the first hybridization, both samples were mixed together and about 150 ng heat-denatured driver in 1.5 μl hybridization buffer were added. The sample is allowed to hybridize for 10–14 hours. Hybridization was stopped by adding 200 μl of dilution buffer (20 mM Hepes, pH 8.3, 50 mM NaCl, 0.2 mM EDTA) and by heating for 7 min at 68° C.

PCR Amplification

Two PCR amplification reactions were carried out for each subtraction in a volume of 25 μl. First PCR was performed in Taq long template buffer 1 (Roche) with 1 μl of diluted, subtracted cDNA, 1 μl PCR primer P1–30 (SEQ ID NO: 35) (8 μM) and 1 μl primer P2–30 (SEQ ID NO: 36) (8 μM) and 0.4 mM dNTPs. Taq polymerase was added in a hot start procedure. The PCR-cycler was set to 75° C. for 7 min (filling in the ends), 27 cycles were performed (94° C., 30 sec; 66° C., 30 sec; 72° C., 1.5 min) and a final extension at 72° C. for 7 min. PCR products were diluted 10 fold in water and 1 μl was used for a secondary PCR performed according to the protocol described above, but using PCR primers PN1–30 (SEQ ID NO: 39) and PN2–30 (SEQ ID NO: 40) and 12 cycles (94° C., 30 sec.; 68° C., 30 sec; 72° C., 1.5 min). PCR products were analyzed by gel electrophoresis on a 1.5% agarose gel.

Cloning and Analysis of Subtracted cDNA

Products from secondary PCR were ligated into the pGEM-Teasy, a T/A cloning system (Promega). After selection of clones with X-Gal/IPTG/ampicilline, inserts were screened by PCR using PN1-30 (SEQ ID NO: 39) and PN2-30 (SEQ ID NO: 40) primers. Differential expression was verified by southern blot analysis of the amplified inserts using labeled tester and driver as probes. Labeling of the driver and tester samples was identical to the labeling for array analysis.

Differentially hybridizing clones were subjected to plasmid preparation using the QIAprep Spin Miniprep Kit (Qiagen) and sequenced. Nucleic acid homology search was performed using the BLAST program (NCBI).

Results

PCR amplification was performed with primer sets of different length (30 nucleotides: P1–30 (SEQ ID NO: 35), P2–30 (SEQ ID NO: 36) and 33 nucleotides: P1–33 (SEQ ID NO: 37) and P2–33 (SEQ ID NO: 38)) both leading to comparable results. Most preferable were primers consisting of 30 nucleotides (P1–30 (SEQ ID NO: 35) and P2–30 (SEQ ID NO: 36)). Smaller primers with 22 nucleotides (Clonetech) as described by Diatchenko (Proc. Natl. Acad. Sci. USA 93 (1996) did not work in PCR reaction. After subtraction, colonies were screened by PCR and the products were subjected to gel electrophoresis and blotting. Labeled tester and driver were hybridized onto the blot as shown for one example in FIG. 25. Colony #4 was identified as a transcription factor described as epithelium-specific gene (Oettgen Genomics 445, (1997) 456–457 and Oettgen Mol. Cell. Biol. 17 (1997), 4419–4433) and Oettgen Genomics 55 (1999), 358–62. This result was confirmed by PCR using the samples from which driver and tester had been prepared (FIG. 26).

The invention claimed is:

1. A method for the amplification of mRNA of a sample comprising:
   i. generating cDNA from polyadenylated RNA employing at least one primer hybridizing to said polyadenylated RNA and comprising a 5' poly(C) or a 5' poly(G) flank wherein the concentration of said at least one primer is in the range of 10 μM to 60 μM;
   ii. 3' tailing of said generated cDNA with a poly(G) tail when at least one of said primers comprises a 5' poly(C) flank or with a poly(C) tail when at least one of said primers comprises a 5' poly(G) flank; and
   iii. amplifying the tailed cDNA with a primer hybridizing to the tail(s) generated in ii. to obtain amplified cDNA; wherein said at least one primer in step i. comprises SEQ ID NO: 10.

2. The method of claim 1, wherein said primer in step iii comprises a stretch of at least 10 nucleotides capable of hybridizing with the tail(s) generated in step ii.

3. The method of claim 2, wherein said primer in step iii comprises the sequence selected from the group consisting of SEQ ID NOS: SEQ ID NO: 11, 12, 13, 14 and 15.

4. The method of claim 1, wherein said polyadenylated RNA is bound to a solid support.

5. The method of claim 4, wherein said solid support is a bead, a membrane, a filter, a well, a chip or a tube.

6. The method of claim 5, wherein said bead is a magnetic bead, a latex bead or a colloid metal bead.

7. The method of claim 5, wherein said bead comprises an oligo(dT) stretch.

8. The method of claim 1, wherein said mRNA is derived from a tissue, a low number of cells or a single cell.

9. The method of claim 8, wherein said low number of cells is in a range of $10^6$ to 2 cells.

10. The method of claim 8, wherein said tissue, cells or single cell is of plant or animal origin.

11. The method of claim 10, wherein said animal is human.

12. The method of claim 8, wherein said tissue, low number of cells or single cell is a chemically fixed tissue, chemically fixed low number of cells or chemically fixed cell.

13. The method of claim 8, wherein said tissue, low number of cells or single cell is derived from a body fluid or from solid tissue.

14. The method of claim 1, further comprising:
   iv. modifying the generated amplified cDNA of iii.

15. The method of claim 14, wherein said modification comprises the introduction of means for detection.

16. The method of claim 15, wherein said means of detection comprises the introduction of nucleotide analogues coupled to (a) chromophore(s), (a) fluorescent dye(s), (a) radio-nucleotide(s), biotin or DIG.

17. The method of claim 1, wherein the obtained amplified cDNA is bound to a solid support.

18. The method of claim 1, wherein all or individual steps are carried out in a non-cacodylate buffer.

19. The method of claim 18, wherein said non-cacodylate buffer is a phosphate buffer.

20. The method of claim 19, wherein said phosphate-buffer is a $KH_2PO_4$ buffer.

21. The method claim 1, wherein said sample is derived from a cell and/or a tissue, the genetic identity of which had been defined by comparative genomic hybridization.

22. A method for the preparation of an in vitro surrogate for at least one pathologically modified cell or tissue comprising:
   (a) amplifying mRNA of said at least one pathologically modified cell or tissue according to the method of claim 1;
   (b) assessing the quantity and, optionally, biophysical characteristics of the amplified cDNA and/or transcripts thereof, thereby determining the gene expression pattern of said pathologically modified cell(s) or tissue(s);
   (c) selecting a human CASMC cell treated with IFN-γ, the gene expression pattern of which resembles the gene expression pattern of said at least one pathologically modified cell or tissue; and
   (d) adapting the gene expression pattern of said CASMC cell to the gene expression pattern of the pathologically modified cell or tissue,
wherein said pathologically modified cell or tissue is a human restenotic cell or restenotic tissue.

23. The method of claim 22, further comprising in (b):
   i. determining the gene expression pattern of at least one control cell or control tissue; and
   ii. determining at least one gene which is differentially expressed in said pathologically modified cell or tissue and said control cell or tissue.

24. The method of claim 23, wherein said gene expression pattern of a control cell or a control tissue is determined employing the method of RNA amplification used to amplify the pathologically modified cell or tissue.

25. The method of claim 23, wherein said control cells or tissue is smooth muscle cells or media/intima of healthy coronary arteries.

26. The method of claim 22, wherein said in vitro cell is or is derived form a primary cell culture, a secondary cell culture, a tissue culture or a cell line.

27. The method of claim 26, wherein said in vitro cell is selected from the group consisting of cultured coronary artery smooth muscle cells, HepG2 cells, Jurkat cells, THP-I cells, Monomac-6-cells, U937 cells, ATCC 45505 cells, cultured cardiomyocytes, ECV 304 cells and NIH3T3 cells.

28. The method of claim 22, wherein said adaptation in step c comprises the exposure of said in vitro cell to physical and/or chemical changes.

29. The method of claim 28, wherein said physical changes comprise temperature shifts, light changes, pH-changes in ionic strength or changes in the gas phase.

30. The method of claim 28, wherein said chemical changes comprise medium exchanges, medium substitutions, medium depletions and/or medium additions.

31. The method of claim 28, wherein said chemical changes comprise the exposure to compounds selected from the group consisting of growth factors, hormones, vitamins, antibodies or fragments and/or derivatives thereof, cytokines, transcription factors, kinases, antibiotics, natural receptor ligands, non-natural receptor ligands and components of signal transduction pathways.

32. The method of claim 31, wherein said cytokine is IFN-γ or a functional derivative thereof, said natural or non-natural receptor ligand is a ligand for IFN-γ receptor, said transcription factor is IRF-1 or ISGF3-γ-(p48), said kinase is tyrosine kinase Pyk2, said components of signal transduction pathways is Dap-1, BAG-1, Pim-1 or IFN-γ-inducible protein 9–27, said growth factor is platelet growth factor AA, angiotension or fibroblast growth factor or said antibiotic is rapamycin.

33. A method for identifying differentially expressed genes in a test sample comprising:
   (a) providing a test sample and a control sample each comprising polyadenylated RNA;

(b) employing the steps of the method of claim 1 on said test and control sample; and (c) comparing the obtained amplified cDNA of said test sample with the obtained amplified cDNA of said control sample.

34. A method for identifying a drug candidate for prevention or therapy of a pathological condition or a pathological disorder comprising:

(a) contacting a sample comprising polyadenylated RNA with a drug candidate;

(b) employing the steps of the method of claim 1 on said sample; and (c) detecting the presence, the absence, the increase or the decrease of particular expressed genes in said sample, wherein the correlation of said presence, absence, increase or decrease with the presence of said drug candidate qualifies said drug candidate as a drug.

35. A method for in vitro detection of a pathological condition or a susceptibility to a pathological condition in a subject comprising:

(a) providing a sample comprising polyadenylated RNA from said subject;

(b) employing the steps of the method of claim 1 on said sample; and (c) detecting a pathological condition or a susceptibility to a pathological condition based on the presence, the absence, the increase, the decrease or the amount of (a) expressed gene(s) in said sample.

36. A method of identifying a drug candidate for prevention or therapy of a pathological condition or a pathological disorder in an in vitro surrogate comprising:

(a) contacting an in vitro surrogate for at least one pathologically modified cell or tissue produced according to the method of claim 22 with a drug candidate; and (b) detecting the presence, the absence, the increase or the decrease of particular expressed genes in said sample, wherein the correlation of said presence, absence, increase or decrease with the presence of said drug candidate qualifies said drug candidate as a drug, wherein said pathological condition or pathological disorder is restenosis and said pathologically modified cell or tissue is a human restenotic cell or restenotic tissue.

37. A method of utilizing amplified cDNA comprising:

(a) preparing amplified cDNA according to the method of claim 1, and (b) utilizing said amplified cDNA in a method selected from the group consisting of in vitro expression of proteins or polypeptides, in vivo expression of proteins or polypeptides, in vitro preparation of mRNA transcripts, in vivo preparation of mRNA transcripts, hybridization assays, interaction assays, sequence specific PCR, cDNA cloning, substractive hybridization cloning and expression cloning.

38. The method of claim 37, wherein said hybridization assay comprises the hybridization to oligonucleotide arrays, cDNA arrays, and/or PNA arrays.

39. The method of claim 37, wherein said interaction assay comprises the interaction with at least one carbohydrate, lectin, ribozyme, protein, peptide, antibody, antibody fragment, aptamer or a combination thereof.

40. A kit comprising SEQ ID NO:10.

\* \* \* \* \*